United States Patent
Schermerhorn et al.

(10) Patent No.: US 11,471,086 B2
(45) Date of Patent: *Oct. 18, 2022

(54) SYSTEMS AND METHODS FOR PERFORMING NEUROPHYSIOLOGIC MONITORING

(71) Applicant: NuVasive, Inc., San Diego, CA (US)

(72) Inventors: Richard W. Schermerhorn, San Diego, CA (US); Eric Finley, San Diego, CA (US); Adam Azzara, San Diego, CA (US); Dmitry Novikov, San Diego, CA (US); James E. Gharib, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 623 days.

This patent is subject to a terminal disclaimer.

(21) Appl. No.: 16/530,925

(22) Filed: Aug. 2, 2019

(65) Prior Publication Data
US 2019/0350473 A1 Nov. 21, 2019

Related U.S. Application Data

(63) Continuation of application No. 14/856,525, filed on Sep. 16, 2015, now Pat. No. 10,420,480.

(60) Provisional application No. 62/136,760, filed on Mar. 23, 2015, provisional application No. 62/051,141, filed on Sep. 16, 2014.

(51) Int. Cl.
*A61B 5/24* (2021.01)

(52) U.S. Cl.
CPC ..................... *A61B 5/24* (2021.01)

(58) Field of Classification Search
CPC .......... A61B 5/24; A61B 5/389; A61B 34/10; A61B 17/0206; A61B 34/25; A61B 2017/00039; A61B 2017/00115; A61B 2017/00154; A61B 5/407; A61B 5/743; A61N 1/0551

See application file for complete search history.

(56) References Cited

U.S. PATENT DOCUMENTS

| | | |
|---|---|---|
| 208,227 A | 9/1878 | Dorr |
| 972,983 A | 10/1910 | Arthur |
| 1,328,624 A | 1/1920 | Graham |
| 1,548,184 A | 8/1925 | Cameron |
| 2,704,064 A | 3/1955 | Fizzell et al. |
| 2,736,002 A | 2/1956 | Oriel |
| 2,808,826 A | 10/1957 | Reiner et al. |
| 3,364,929 A | 1/1968 | Ide et al. |
| 3,664,329 A | 5/1972 | Naylor |
| 3,682,162 A | 8/1972 | Coyler |
| 3,785,368 A | 1/1974 | McCarthy et al. |

(Continued)

OTHER PUBLICATIONS

Bednarik, et al., "The Value of Somatosensory- and Motor-Evoked Potentials in Predicting and Monitoring the Effect of Therapy in Spondylotic Cervical Myelopathy," Spine 1999, 24(15):1593-1598.

(Continued)

*Primary Examiner* — Rene T Towa
(74) *Attorney, Agent, or Firm* — Merchant & Gould P.C.

(57) ABSTRACT

The present invention relates to a system and methods generally aimed at surgery. More particularly, the present invention is directed at a system and related methods for performing surgical procedures and assessments involving the use of neurophysiology.

20 Claims, 35 Drawing Sheets

(56) References Cited

U.S. PATENT DOCUMENTS

| | | | |
|---|---|---|---|
| 3,830,226 | A | 8/1974 | Staub |
| 3,851,641 | A | 12/1974 | Toole et al. |
| 3,957,036 | A | 5/1976 | Norman |
| 4,099,519 | A | 7/1978 | Warren |
| 4,164,214 | A | 8/1979 | Stark et al. |
| 4,207,897 | A | 6/1980 | Lloyd et al. |
| 4,224,949 | A | 9/1980 | Scott et al. |
| 4,226,228 | A | 10/1980 | Shin et al. |
| 4,235,242 | A | 11/1980 | Howson et al. |
| 4,252,130 | A | 2/1981 | Le Pivert |
| 4,285,347 | A | 8/1981 | Hess |
| 4,291,705 | A | 9/1981 | Severinghaus et al. |
| 4,461,300 | A | 7/1984 | Christensen |
| 4,515,168 | A | 5/1985 | Chester et al. |
| 4,519,403 | A | 5/1985 | Dickhudt |
| 4,545,374 | A | 10/1985 | Jacobson |
| 4,561,445 | A | 12/1985 | Berke et al. |
| 4,562,832 | A | 1/1986 | Wilder et al. |
| 4,573,448 | A | 3/1986 | Kambin |
| 4,592,369 | A | 6/1986 | Davis et al. |
| 4,595,018 | A | 6/1986 | Rantala |
| 4,633,889 | A | 1/1987 | Talalla et al. |
| 4,658,835 | A | 4/1987 | Pohndorf |
| 4,744,371 | A | 5/1988 | Harris |
| 4,759,377 | A | 7/1988 | Dykstra |
| 4,784,150 | A | 11/1988 | Voorhies et al. |
| 4,807,642 | A | 2/1989 | Brown |
| 4,892,105 | A | 1/1990 | Prass |
| 4,926,865 | A | 5/1990 | Oman |
| 4,962,766 | A | 10/1990 | Herzon |
| 4,964,411 | A | 10/1990 | Johnson et al. |
| 5,007,902 | A | 4/1991 | Witt |
| 5,058,602 | A | 10/1991 | Brody |
| 5,081,990 | A | 1/1992 | Deletis |
| 5,092,344 | A | 3/1992 | Lee |
| 5,127,403 | A | 7/1992 | Brownlee |
| 5,161,533 | A | 11/1992 | Prass et al. |
| 5,196,015 | A | 3/1993 | Neubardt |
| 5,220,920 | A | 6/1993 | Gharib |
| RE34,390 | E | 9/1993 | Culver |
| 5,255,691 | A | 10/1993 | Otten |
| 5,282,468 | A | 2/1994 | Klepinski |
| 5,284,153 | A | 2/1994 | Raymond et al. |
| 5,284,154 | A | 2/1994 | Raymond et al. |
| 5,299,563 | A | 4/1994 | Seton |
| 5,312,417 | A | 5/1994 | Wilk |
| 5,313,956 | A | 5/1994 | Knutson et al. |
| 5,327,902 | A | 7/1994 | Lemmen |
| 5,333,618 | A | 8/1994 | Lekhtman et al. |
| 5,375,067 | A | 12/1994 | Berchin |
| 5,383,876 | A | 1/1995 | Nardella |
| 5,450,845 | A | 9/1995 | Axelgaard |
| 5,474,558 | A | 12/1995 | Neubardt |
| 5,480,440 | A | 1/1996 | Kambin |
| 5,482,038 | A | 1/1996 | Ruff |
| 5,484,437 | A | 1/1996 | Michelson |
| 5,540,235 | A | 7/1996 | Wilson |
| 5,549,656 | A | 8/1996 | Reiss |
| 5,560,372 | A | 10/1996 | Cory |
| 5,566,678 | A | 10/1996 | Cadwell |
| 5,579,781 | A | 12/1996 | Cooke |
| 5,593,429 | A | 1/1997 | Ruff |
| 5,599,279 | A | 2/1997 | Slotman |
| 5,601,608 | A | 2/1997 | Mouchawar |
| 5,630,813 | A | 5/1997 | Kieturakis |
| 5,671,752 | A | 9/1997 | Sinderby et al. |
| 5,707,359 | A | 1/1998 | Bufalini |
| 5,711,307 | A | 1/1998 | Smits |
| 5,728,046 | A | 3/1998 | Mayer |
| 5,741,253 | A | 4/1998 | Michelson |
| 5,758,643 | A | 6/1998 | Wong et al. |
| 5,759,159 | A | 6/1998 | Masreliez |
| 5,772,661 | A | 6/1998 | Michelson |
| 5,775,331 | A | 7/1998 | Raymond et al. |
| 5,776,144 | A | 7/1998 | Leysieffer et al. |
| 5,779,642 | A | 7/1998 | Nightengale |
| 5,785,658 | A | 7/1998 | Benaron et al. |
| 5,797,854 | A | 8/1998 | Hedgecock |
| 5,806,522 | A | 9/1998 | Katims |
| 5,807,272 | A | 9/1998 | Kun et al. |
| 5,814,073 | A | 9/1998 | Bonutti |
| 5,830,150 | A | 11/1998 | Palmer et al. |
| 5,830,151 | A | 11/1998 | Hadzic et al. |
| 5,851,191 | A | 12/1998 | Gozani et al. |
| 5,853,373 | A | 12/1998 | Griffith et al. |
| 5,860,973 | A | 1/1999 | Michelson |
| 5,862,314 | A | 1/1999 | Jeddeloh |
| 5,872,314 | A | 2/1999 | Clinton |
| 5,885,219 | A | 3/1999 | Nightengale |
| 5,888,196 | A | 3/1999 | Bonutti |
| 5,902,231 | A | 5/1999 | Foley et al. |
| 5,928,139 | A | 7/1999 | Koros et al. |
| 5,928,158 | A | 7/1999 | Aristides |
| 5,928,159 | A | 7/1999 | Eggers et al. |
| 5,935,131 | A | 8/1999 | Bonutti |
| 5,938,688 | A | 8/1999 | Schiff |
| 5,947,964 | A | 9/1999 | Eggers et al. |
| 5,976,094 | A | 11/1999 | Gozani |
| 6,004,262 | A | 12/1999 | Putz et al. |
| 6,011,985 | A | 1/2000 | Athan |
| 6,026,323 | A | 2/2000 | Skladnev et al. |
| 6,027,456 | A | 2/2000 | Feler et al. |
| 6,038,469 | A | 3/2000 | Karlsson et al. |
| 6,038,477 | A | 3/2000 | Kayyali |
| 6,050,992 | A | 4/2000 | Nichols |
| 6,074,343 | A | 6/2000 | Nathanson et al. |
| 6,104,957 | A | 8/2000 | Alo et al. |
| 6,104,960 | A | 8/2000 | Duysens et al. |
| 6,119,068 | A | 9/2000 | Kannonji |
| 6,120,503 | A | 9/2000 | Michelson |
| 6,128,576 | A | 10/2000 | Nishimoto |
| 6,132,386 | A | 10/2000 | Gozani et al. |
| 6,132,387 | A | 10/2000 | Gozani et al. |
| 6,135,965 | A | 10/2000 | Turner et al. |
| 6,139,493 | A | 10/2000 | Koros et al. |
| 6,146,335 | A | 11/2000 | Gozani |
| 6,161,047 | A | 12/2000 | King et al. |
| 6,181,961 | B1 | 1/2001 | Prass |
| 6,206,826 | B1 | 3/2001 | Mathews et al. |
| 6,224,549 | B1 | 5/2001 | Drongelen |
| 6,259,945 | B1 | 7/2001 | Epstein et al. |
| 6,266,558 | B1 | 7/2001 | Gozani et al. |
| 6,273,905 | B1 | 8/2001 | Streeter |
| 6,292,701 | B1 | 9/2001 | Prass et al. |
| 6,306,100 | B1 | 10/2001 | Prass |
| 6,312,392 | B1 | 11/2001 | Herzon |
| 6,325,764 | B1 | 12/2001 | Griffith et al. |
| 6,334,068 | B1 | 12/2001 | Hacker |
| 6,337,994 | B1 | 1/2002 | Stoianovici et al. |
| 6,393,325 | B1 | 5/2002 | Mann et al. |
| 6,407,335 | B1 | 6/2002 | Franklin-Lees et al. |
| 6,416,480 | B1 | 7/2002 | Nenov |
| 6,425,859 | B1 | 7/2002 | Foley et al. |
| 6,425,901 | B1 | 7/2002 | Zhu et al. |
| 6,451,015 | B1 | 9/2002 | Rittman et al. |
| 6,466,817 | B1 | 10/2002 | Kaula et al. |
| 6,500,128 | B2 | 12/2002 | Marino |
| 6,535,759 | B1 | 3/2003 | Epstein et al. |
| 6,564,078 | B1 | 5/2003 | Marino et al. |
| 6,579,244 | B2 | 6/2003 | Goodwin |
| 6,593,528 | B2 | 7/2003 | Franklin-Lees et al. |
| 6,719,692 | B2 | 4/2004 | Kleffner et al. |
| 6,760,616 | B2 | 7/2004 | Hoey et al. |
| 6,796,985 | B2 | 9/2004 | Bolger et al. |
| 6,819,956 | B2 | 11/2004 | DiLorenzo |
| 6,829,508 | B2 | 12/2004 | Schulman et al. |
| 6,830,051 | B1 | 12/2004 | Lesniak et al. |
| 6,849,047 | B2 | 2/2005 | Goodwin |
| 6,855,105 | B2 | 2/2005 | Jackson, III |
| 6,895,280 | B2 | 5/2005 | Meadows et al. |
| 6,902,569 | B2 | 6/2005 | Parmer et al. |
| 6,926,728 | B2 | 8/2005 | Zucherman et al. |
| 6,929,606 | B2 | 8/2005 | Ritland |
| 7,047,082 | B1 | 5/2006 | Schrom et al. |

(56) References Cited

U.S. PATENT DOCUMENTS

| | | | |
|---|---|---|---|
| 7,050,848 B2 | 5/2006 | Hoey et al. |
| 7,079,883 B2 | 7/2006 | Marino et al. |
| 7,089,059 B1 | 8/2006 | Pless |
| D533,875 S | 12/2006 | Miles et al. |
| 7,177,677 B2 | 2/2007 | Kaula et al. |
| 7,207,949 B2 | 4/2007 | Miles et al. |
| 7,216,001 B2 | 5/2007 | Hacker et al. |
| 7,255,680 B1 | 8/2007 | Gharib |
| 7,470,236 B1 | 12/2008 | Kelleher et al. |
| 7,522,953 B2 | 4/2009 | Kaula et al. |
| 7,582,058 B1 | 9/2009 | Miles et al. |
| 7,657,308 B2 | 2/2010 | Miles et al. |
| 7,664,544 B2 | 2/2010 | Miles et al. |
| 7,691,057 B2 | 4/2010 | Miles et al. |
| 7,706,843 B2 | 4/2010 | Kaplan |
| 7,819,801 B2 | 10/2010 | Miles et al. |
| 7,857,813 B2 | 12/2010 | Schmitz et al. |
| 7,878,981 B2 | 2/2011 | Strother et al. |
| 7,887,538 B2 | 2/2011 | Bleich et al. |
| 7,896,815 B2 | 3/2011 | Thrope et al. |
| 7,905,840 B2 | 3/2011 | Pimenta et al. |
| 7,938,830 B2 | 5/2011 | Saadat et al. |
| 7,963,927 B2 | 6/2011 | Kelleher et al. |
| 8,068,912 B2 | 11/2011 | Kaula et al. |
| 10,420,480 B1 | 9/2019 | Schermerhorn |
| 2001/0039949 A1 | 11/2001 | Loubser |
| 2001/0056280 A1 | 12/2001 | Underwood et al. |
| 2002/0007129 A1 | 1/2002 | Marino |
| 2002/0072686 A1 | 6/2002 | Hoey et al. |
| 2002/0123780 A1 | 9/2002 | Grill et al. |
| 2002/0134570 A1 | 9/2002 | Franklin-Lees et al. |
| 2002/0161415 A1 | 10/2002 | Cohen et al. |
| 2002/0193843 A1 | 12/2002 | Hill |
| 2003/0032966 A1 | 2/2003 | Foley et al. |
| 2003/0105503 A1 | 6/2003 | Marino |
| 2004/0158298 A1 | 8/2004 | Gliner |
| 2004/0199084 A1 | 10/2004 | Kelleher et al. |
| 2004/0203490 A1 | 10/2004 | Kaplan |
| 2004/0225228 A1 | 11/2004 | Ferree |
| 2005/0004593 A1 | 1/2005 | Simonson |
| 2005/0004623 A1 | 1/2005 | Miles et al. |
| 2005/0033380 A1 | 2/2005 | Tanner et al. |
| 2005/0075578 A1 | 4/2005 | Gharib et al. |
| 2005/0149035 A1 | 7/2005 | Pimenta et al. |
| 2005/0159785 A1 | 7/2005 | Rueter |
| 2005/0182454 A1 | 8/2005 | Gharib et al. |
| 2005/0192575 A1 | 9/2005 | Pacheco |
| 2006/0025703 A1 | 2/2006 | Miles et al. |
| 2006/0052828 A1 | 3/2006 | Kim et al. |
| 2006/0069315 A1 | 3/2006 | Miles et al. |
| 2006/0166157 A1 | 7/2006 | Rahman et al. |
| 2006/0224078 A1 | 10/2006 | Hoey et al. |
| 2007/0016097 A1 | 1/2007 | Farquhar et al. |
| 2007/0021682 A1 | 1/2007 | Gharib et al. |
| 2007/0198062 A1 | 8/2007 | Miles et al. |
| 2007/0293782 A1 | 12/2007 | Marino |
| 2008/0058606 A1 | 3/2008 | Miles et al. |
| 2008/0064976 A1 | 3/2008 | Kelleher et al. |
| 2008/0064977 A1 | 3/2008 | Kelleher et al. |
| 2008/0065178 A1 | 3/2008 | Kelleher et al. |
| 2008/0071191 A1 | 3/2008 | Kelleher et al. |
| 2008/0097164 A1 | 4/2008 | Miles et al. |
| 2008/0167574 A1 | 7/2008 | Farquhar et al. |
| 2008/0221473 A1 | 9/2008 | Calancie et al. |
| 2009/0018399 A1 | 1/2009 | Martinelli |
| 2009/0018610 A1 | 1/2009 | Gharib et al. |
| 2009/0054804 A1 | 2/2009 | Gharib et al. |
| 2009/0105604 A1 | 4/2009 | Bertagnoli et al. |
| 2009/0124860 A1 | 5/2009 | Miles et al. |
| 2009/0177112 A1 | 7/2009 | Gharib et al. |
| 2009/0192403 A1 | 7/2009 | Gharib et al. |
| 2009/0204016 A1 | 8/2009 | Gharib et al. |
| 2009/0204176 A1 | 8/2009 | Miles et al. |
| 2009/0209879 A1 | 8/2009 | Kaula et al. |
| 2009/0259108 A1 | 10/2009 | Miles et al. |
| 2010/0010367 A1 | 1/2010 | Foley et al. |
| 2010/0036384 A1 | 2/2010 | Gorek et al. |
| 2010/0069783 A1 | 3/2010 | Miles et al. |
| 2010/0076335 A1 | 3/2010 | Gharib et al. |
| 2010/0094093 A1 | 4/2010 | Miles et al. |
| 2010/0105986 A1 | 4/2010 | Miles et al. |
| 2010/0105987 A1 | 4/2010 | Miles et al. |
| 2010/0113884 A1 | 5/2010 | Miles et al. |
| 2010/0130827 A1 | 5/2010 | Pimenta et al. |
| 2010/0137690 A1 | 6/2010 | Miles et al. |
| 2010/0152603 A1 | 6/2010 | Miles et al. |
| 2010/0152604 A1 | 6/2010 | Kaula et al. |
| 2010/0160738 A1 | 6/2010 | Miles et al. |
| 2010/0174146 A1 | 7/2010 | Miles et al. |
| 2010/0174147 A1 | 7/2010 | Miles et al. |
| 2010/0174148 A1 | 7/2010 | Miles et al. |
| 2010/0249644 A1 | 9/2010 | Miles et al. |
| 2010/0273738 A1 | 10/2010 | Valcke et al. |
| 2010/0312103 A1 | 12/2010 | Gorek et al. |
| 2011/0054346 A1 | 3/2011 | Hausman |
| 2011/0105939 A1* | 5/2011 | Yong .............. A61B 5/7264 600/554 |
| 2012/0095360 A1* | 4/2012 | Runney ........... A61B 5/377 600/554 |
| 2012/0226186 A1 | 9/2012 | Baars et al. |
| 2014/0316484 A1 | 10/2014 | Edgerton et al. |

OTHER PUBLICATIONS

Calancie, et al., "'Threshold-level' multipulse transcranial electrical stimulation of motor cortex for intraoperative monitoring of spinal motor tracts: description of method and comparison to somatosensory evoked potential monitoring," J Neurosurg 1998, 88:457-470.

Calancie, et al., "Threshold-level repetitive transcranial electrical stimulation for intraoperative monitoring of central motor conduction," J Neurosurg (Spine 1) 2011, 95:161-168.

Calancie and Molano, "Alarm Criteria for Motor-Evoked Potentials," Spine 2008 33(4):406-414.

Deletis, et al., "Neurophysiological mechanisms underlying motor evoked potentials in anesthetized humans. Part 1. Recovery time of corticospinal tract direct waves elicited by pairs of transcranial electrical stimuli," Clin Neurophysiol 2001, 112:438-444.

Deletis, et al., "Neurophysiological mechanisms underlying motor evoked potentials in anesthetized humans. Part 2. Relationship between epidurally and muscle recorded MEPs in man," Clin Neurophysiol 2001, 112:445-452.

Ginsburg, et al., "Postoperative paraplegia with preserved intraoperative somatosensory evoked potentials," J Neurosurg 1985, 63:296-300.

Gokaslan, et al., "Intraoperative Monitoring of Spinal Cord Function Using Motor Evoked Potentials via Transcutaneous Epidural Electrode During Anterior Cervical Spinal Surgery," J Spinal Disord 1997, 10(4):299-303.

Kombos, et al., "Monitoring of intraoperative motor evoked potentials to increase the safety of surgery in and around the motor cortex," J Neurosurg 2001, 95:608-614.

Langeloo, et al., "A New Application of TCE-MEP: Spinal Cord Monitoring in Patients With Severe Neuromuscular Weakness Undergoing Corrective Spine Surgery," J Spinal Disord 2001, 14(5):445-448.

Langeloo, et al., "Transcranial Electrical Motor-Evoked Potential Monitoring During Surgery for Spinal Deformity," Spine 2003, 28(10) 1043-1050.

Macdonald, "Safety of Intraoperative Transcranial Electrical Stimulation Motor Evoked Potential Monitoring," J Clin Neurophys 2002, 19(5):416-429.

Osburn, et al., "TCeMEPs offer Safe, Reliable Monitoring of Spinal Cord Motor Pathway Function during Cervical Procedures Performed for Post-traumatic Spine Injury," 17th Annual Meeting of the American Society of Neurophysiological Monitoring Abstract Presentations, 2006.

(56) References Cited

OTHER PUBLICATIONS

Osburn, "A Guide to the Performance of Transcranial Electrical Motor Evoked Potentials. Part 1. Basic Concepts, Recording Parameters, Special Consideration, and Application," Am J END Technol 2006, 46:98-158.

Watanabe, et al., "Transcranial electrical stimulation through screw electrodes for intraoperative monitoring of motor evoked potentials," J Neurosurg 2004, 100:155-160.

Wiedemayer, et al., "False negative findings in intraoperative SEP monitoring: analysis of 658 neurosurgical cases and review of published reports," J Neurol Neurosurg Psychiatry 2004, 75:280-286.

Balzer, et al., "Simultaneous Somatosensory Evoked Potential and Electromyographic Recordings during Lumbosacral Decompression and Instrumentation Technique Application," Neurosurgery 1998, 42:1318-1325.

Banoczi, "Update on Anesthetic and Metabolic Effects During Intraoperative Neurophysiological Monitoring (IONM)," Am J END Technol 2005, 45:225-239.

Chawla, et al., "Somatosensory Evoked Potentials: Clinical Applications," eMedicine Neurology, 2008, http://emedicine.medscape.com/article/1139393-overview.

Dawson, et al., "Spinal Cord Monitoring. Results of the Scoliosis Research Society and the European Spinal Deformity Society Survey," Spine 1991, 16(8) Supplement: S361-S364.

Deutsch, et al., "Somatosensory evoked potential monitoring in anterior thoracic vertebrectomy," J Neurosurg (Spine2) 2000, 92:155-161.

Devlin and Schwartz, "Intraoperative Neurophysiologic Monitoring During Spinal Surgery," J Am Acad Orthop Surg 2007, 15(9):549-560.

Gunnarsson, et al., "Real-Time Continuous Intraoperative Electromyographic and Somatosensory Evoked Potential Recordings in Spinal Surgery: Correlation of Clinical and Electrophysiologic Findings in a Prospective, Consecutive Series of 213 Cases," Spine 2004, 29(6):677-684.

Jones, et al., "Two cases of quadriparesis following anterior cervical discectomy, with normal perioperative somatosensory evoked potentials," J Neurol Neurosurg Psychiatry 2003, 74:273-276.

Kamel, et al., "The Use of Somatosensory Evoked Potentials to Determine the Relationship Between Patient Positioning and Impending Upper Extremity Nerve Injury During Spine Surgery: A Retrospective analysis," International Anesthesia Research Society 2006, 102:1538-1542.

Kombos, et al., "Impact of Somatosensory Evoked Potential Monitoring on Cervical Surgery," J Clin Neurophys 2003, 20(2): 122-128.

Kraft, et al., "Somatosensory Evoked Potentials: Clinical Uses," Muscle Nerve 1998, 21:252-258.

Legatt and Soliman, "Somatosensory Evoked Potentials: General Principles," eMedicine Neurology, 2006, http://emedicine.medscape.com/article/1139906-overview.

More, et al., "Cortical Evoked Potential Monitoring During Spinal Surgery: Sensitivity, Specificity, Reliability, and Criteria for Alarm," J Spinal Disord 1988, 1(1):75-80.

Nash, et al., "Spinal Cord Monitoring During Operative Treatment of the Spine," Clin Orthop Relat Res 1977, 126:100-105.

Nuwer, et al., "Somatosensory evoked potential spinal cord monitoring reduces neurologic deficits after scoliosis surgery: results of a large multicenter survey," Electroencephalogr Clin Neurophysiol 1995, 96:6-11.

Padberg, et al., "Somatosensory- and Motor-Evoked Potential Monitoring Without a Wake-Up Test During Idiopathic Scoliosis Surgery: An Accepted Standard of Care," Spine 1998, 23(12):1392-1400.

Pelosi, et al., "Combined monitoring or motor and somatosensory evoked potentials in orthopaedic spinal surgery," Clin Neurophysiol 2002, 113:1082-1091.

Sloan and Heyer, "Anesthesia for Intraoperative Neurophysiologic Monitoring of the Spinal Cord," J Clin Neurophys 2002, 19(5):430-443.

Toleikis, "Intraoperative Monitoring Using Somatosensory Evoked Potentials," J Clin Monit Comput 2005, 19:241-258.

Wiedemayer, et al., "The impact of neurophysiological intraoperative monitoring on surgical decisions: a critical analysis of 423 cases," J Neurosurg 2002, 96:255-262.

Zornow and Drummond, "Intraoperative Somatosensory Evoked Responses Recorded During Onset of the Anterior Spinal Artery Syndrome," J Clin Monit 1989, 5:243-245.

* cited by examiner

Single Pulse Stimulation Signal

Multipulse Stimulation Signal

SYSTEMS AND METHODS FOR PERFORMING NEUROPHYSIOLOGIC MONITORING

CROSS-REFERENCE TO RELATED APPLICATIONS

This application is a continuation of U.S. patent application Ser. No. 14/856,525, filed Sep. 16, 2015, which claims the benefit of priority from commonly owned and U.S. Provisional Patent Application No. 62/051,141, entitled "Systems and Methods for Performing Neurophysiologic Monitoring During Spine Surgery," filed on Sep. 16, 2014, and U.S. Provisional Patent Application No. 62/136,760, entitled "Method for improved detection of low level SSEP signals," filed on Mar. 23, 2015, the entire contents of both which is hereby expressly incorporated by reference into this disclosure as if set forth in its entirety herein.

FIELD

The present invention relates to a system and methods generally aimed at surgery. More particularly, the present invention is directed at a system and related methods for performing neurophysiologic assessments during surgical procedures.

BACKGROUND

The spinal column is a highly complex system of bones and connective tissues that provide support for the body and protect the delicate spinal cord and nerves. The spinal column includes a series of vertebral bodies stacked one atop the other, each vertebral body including an inner or central portion of relatively weak cancellous bone and an outer portion of relatively strong cortical bone. Situated between each vertebral body is an intervertebral disc that cushions and dampens compressive forces exerted upon the spinal column. A vertebral canal containing the spinal cord is located behind the vertebral bodies.

There are many types of spinal column disorders including scoliosis (abnormal lateral curvature of the spine), excess kyphosis (abnormal forward curvature of the spine), excess lordosis (abnormal backward curvature of the spine), spondylolisthesis (forward displacement of one vertebra over another), and other disorders caused by abnormalities, disease or trauma, such as ruptured or slipped discs, degenerative disc disease, fractured vertebrae, and the like. Patients that suffer from such conditions usually experience extreme and debilitating pain as well as diminished nerve function.

Neurophysiologic monitoring has become an increasingly important adjunct to surgical procedures where neural tissue may be at risk. Spinal surgery, in particular, involves working close to delicate tissue in and surrounding the spine, which can be damaged in any number of different ways. When spinal cord monitoring is required, somatosensory evoked potential (SSEP) monitoring is often chosen. SSEP monitoring traditionally involves complex analysis and specially trained neurophysiologists are generally called upon to perform the monitoring. Even though performed by specialists, interpreting the complex waveforms in this fashion is nonetheless disadvantageously prone to human error and can be disadvantageously time consuming, adding to the duration of the operation and translating into increased healthcare costs. Even more costly is the fact that the neurophysiologist is required in addition to the actual surgeon performing the spinal operation. Past developments have attempted to solve these challenges in various ways. One such development is so-called automated or surgeon-driven SSEPs monitoring.

For some time, surgeon-driven and traditional neuromonitoring systems have co-existed and have experienced some of the same challenges in performing intraoperative neuromonitoring. One such challenge is that neurophysiologic signals are typically sub-microvolt evoked potentials that are hard to resolve in an "electrically hostile" environment such as an operating room. What is needed are systems and methods for improved SSEP data acquisition that provides meaningful data to user. According to a broad aspect of the present invention, there are provided methods and techniques to enhance, facilitate, and/or simplify the process of detecting neurophysiologic signals (e.g. SSEP signals) particularly in the presence of noise including ambient electrical activity and non-evoked biopotentials.

SUMMARY OF THE INVENTION

The present invention includes systems and methods to evaluate the health and status of the lower motor neural pathway before, during and after the establishment of an operative corridor through (or near) any of a variety of tissues having such neural structures which, if contacted or impinged, may otherwise result in neural impairment for the patient. It is expressly noted that, although described herein largely in terms of use in lateral lumbar spinal surgery, the system and methods of the present disclosure are suitable for use in any number of additional spinal surgeries including posterior, posterolateral, anterior, anterolateral lumbar spinal surgeries as well as thoracic and thoracolumbar spinal surgeries. Indeed, the invention of the present disclosure is suitable for use in any number of additional surgical procedures wherein tissue having significant neural structures must be passed through (or near) in order to establish an operative corridor.

According to another broad aspect, the present invention includes a control unit, a patient module, and a plurality of surgical accessories adapted to couple to the patient module. The control unit includes a power supply and is programmed to receive user commands, activate stimulation in a plurality of predetermined modes, process signal data according to defined algorithms, display received parameters and processed data, and monitor system status. The patient module is in communication with the control unit. The patient module is within the sterile field. The patient module includes signal conditioning circuitry, stimulator drive circuitry, and signal conditioning circuitry required to perform said stimulation in said predetermined modes. The patient module includes a processor programmed to perform a plurality of predetermined functions including at least two of neuromuscular pathway assessment, non-evoked monitoring, static pedicle integrity testing, dynamic pedicle integrity testing, nerve proximity detection, manual motor evoked potential monitoring, automatic motor evoked potential monitoring, transcutaneous nerve root testing, manual somatosensory evoked potential monitoring, automatic somatosensory evoked potential monitoring, and surgical correction planning and assessment.

According to still another broad aspect, the present invention includes a processing unit programmed to perform a plurality of predetermined functions using said instrument including at least two of neuromuscular pathway assessment, static pedicle integrity testing, dynamic pedicle integrity testing, nerve proximity detection, transcutaneous nerve root testing, non-evoked monitoring, motor evoked potential monitoring, somatosensory evoked potential monitoring, and surgical correction planning and assessment. The processing system has a pre-established profile for at least one of said predetermined functions so as to facilitate the initiation of said at least one predetermined function.

According to one aspect of the present disclosure, there is provided a hunting algorithm executable on the control unit of the neurophysiologic monitoring system (for example, the neurophysiologic monitoring system shown and described below) that finds a minimum rejection threshold that will quickly find a significant response with a minimum number of responses to provide a significant, well-resolved SSEP waveform for the surgeon without the need for highly trained personnel to be present to acquire or interpret the waveforms. It is to be appreciated while the hunting algorithm described below is described with respect to somatosensory evoked potentials, it is equally applicable to all neurophysiologic modalities, including but not limited to motor evoked potentials (MEP) and transcutaneous, transabdominal evoked potentials. It will also be appreciated that the hunting algorithm described below is applicable to not just spine procedures but any procedure in which one or more aspects of the nervous system are at risk of permanent or transient injury or damage.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems disclosed herein boast a variety of inventive features and components that warrant patent protection, both individually and in combination. The systems and methods described herein boast a variety of inventive features and components that warrant patent protection, both individually and in combination.

Figure 1:
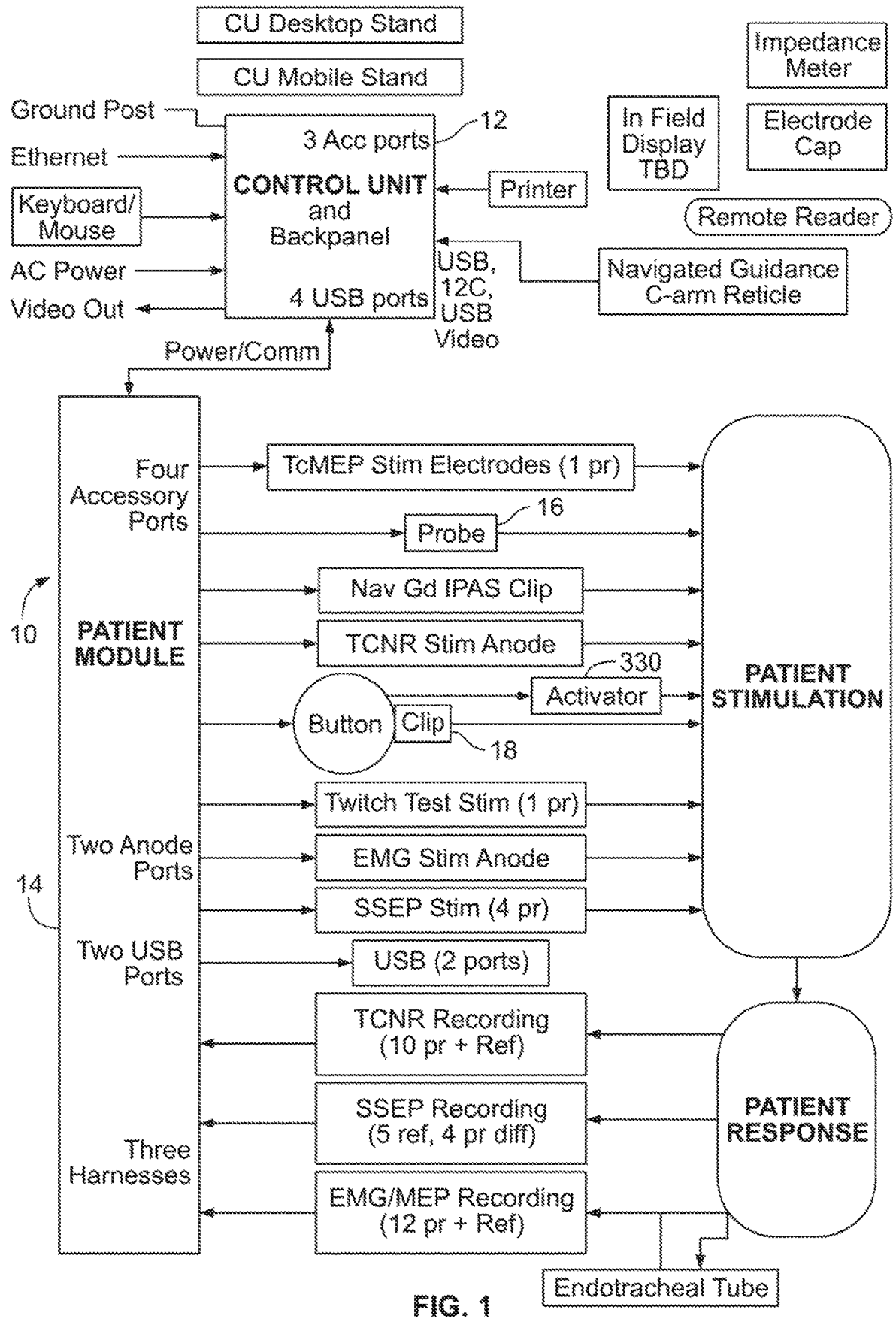
FIG. 1 is a block diagram of an example neurophysiologic monitoring system capable of conducting multiple nerve and spinal cord monitoring functions including but not necessarily limited to neuromuscular pathway, bone integrity, nerve detection, nerve pathology (evoked or free-run EMG), lower motor pathway, MEP, and SSEP assessments.
Figure 2:
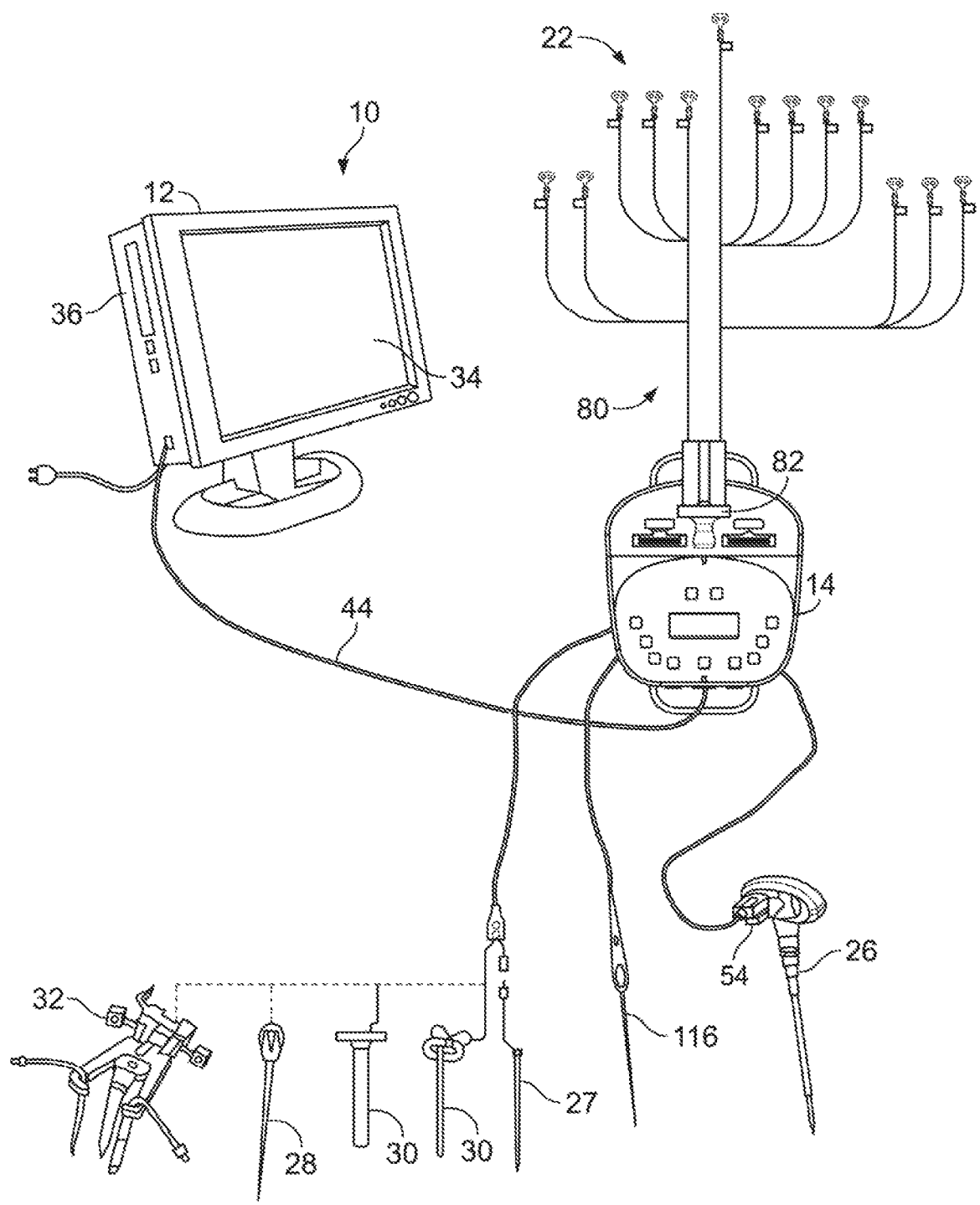
FIG. 2 is a perspective view showing examples of several components of the system of FIG. 1.

A neurophysiologic monitoring system 10 is described herein and is capable of performing a number of neurophysiological and/or guidance assessments at the direction of the surgeon (and/or other members of the surgical team). By way of example only, FIGS. 1-2 illustrate the basic components of the system 10. The system comprises a control unit 12 (including a main display 34 preferably equipped with a graphical user interface (GUI) and a processing unit 36 that collectively contain the essential processing capabilities for controlling the system 10), a patient module 14, a stimulation accessory (e.g. a stimulation probe 16, stimulation clip 18 for connection to various surgical instruments, an inline stimulation hub 20, and stimulation electrodes 22), and a plurality of recording electrodes 24 for detecting electrical potentials.

Figure 20:
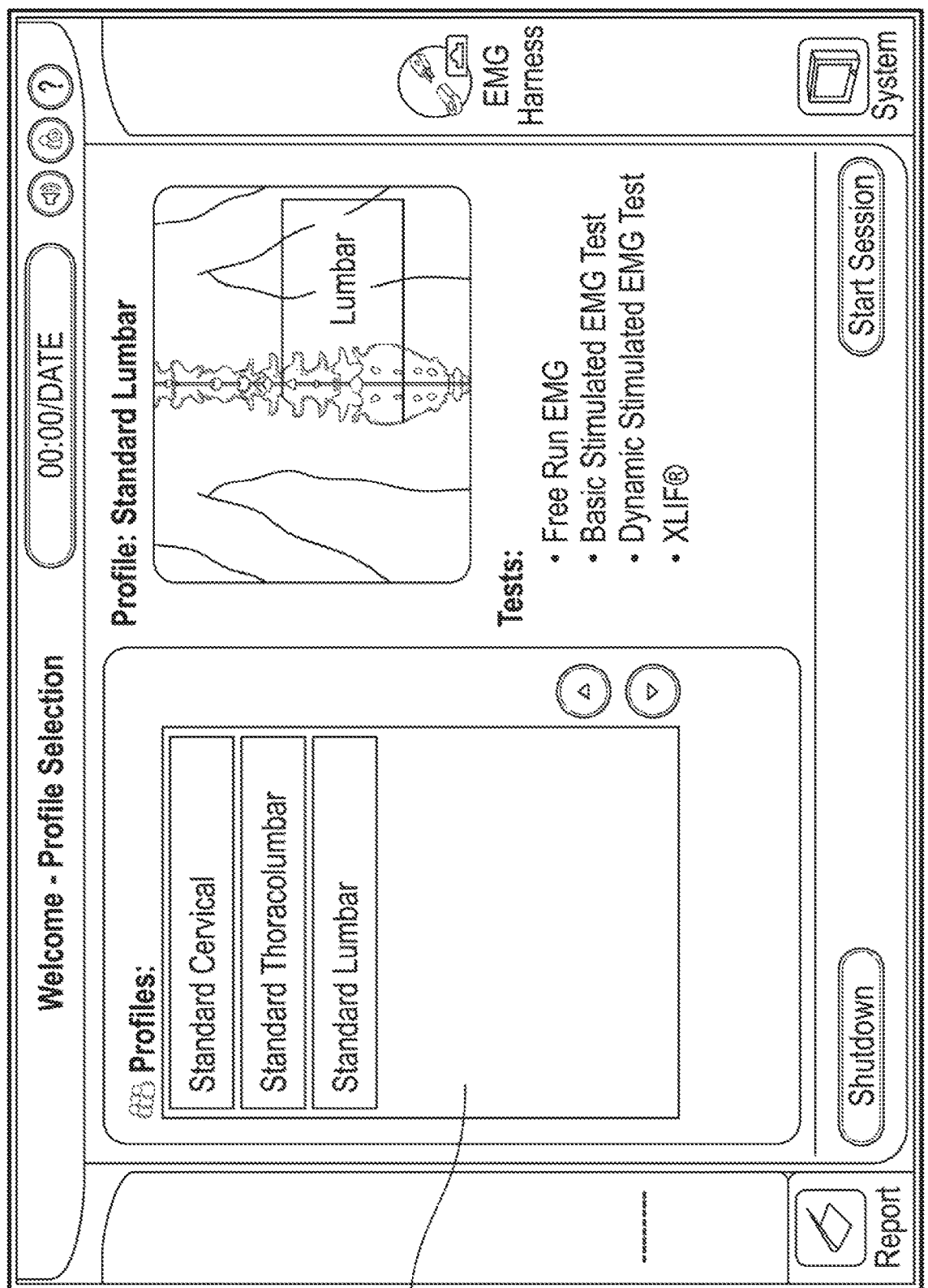
FIG. 20 is a screenshot of an example embodiment of a profile screen forming part of the system of FIG. 1.

The stimulation accessories may be in the form of various probe devices that are themselves inserted into the stimulation site, clips that attach and deliver stimulation signals to standard instruments that are used at various times throughout a procedure and surface electrodes. The stimulation clip 18 may be used to connect any of a variety of surgical instruments to the system 10, including, but not necessarily limited to a pedicle access needle 26, k-wire 27, tap 28, dilator(s) 30, tissue retractor 32, etc. One or more secondary feedback devices (e.g. secondary display 46 in FIGS. 20-21) may also be provided for additional expression of output to a user and/or receiving input from the user.

In one embodiment, the system 10 may be configured to execute any of the functional modes including, but not necessarily limited to, neuromuscular pathway assessment ("Twitch Test"), non-evoked monitoring ("Free-run EMG"), static pedicle integrity testing ("Basic Stimulated EMG"), dynamic pedicle integrity testing ("Dynamic Stimulated EMG"), nerve proximity detection ("XLIF®"), motor evoked potential monitoring ("MEP Manual" and "MEP Automatic"), transcutaneous nerve root testing ("TCNR Alert" and "TCNR Threshold"), somatosensory evoked potential monitoring ("SSEP Manual" and "SSEP Automatic"), and surgical correction planning and assessment. The system 10 may also be configured for performance in any of the lumbar, thoracolumbar, and cervical regions of the spine.

Figure 3:
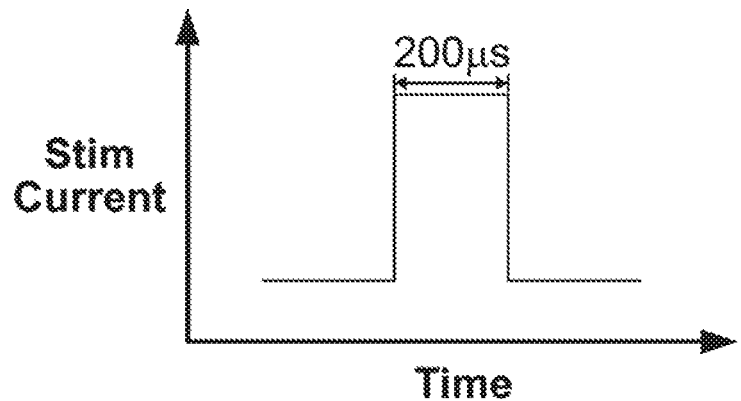
FIG. 3 is a graph illustrating a plot of a single pulse stimulation current signal capable of producing a neuromuscular response (EMG) of the type shown in FIG. 5.
Figure 4:
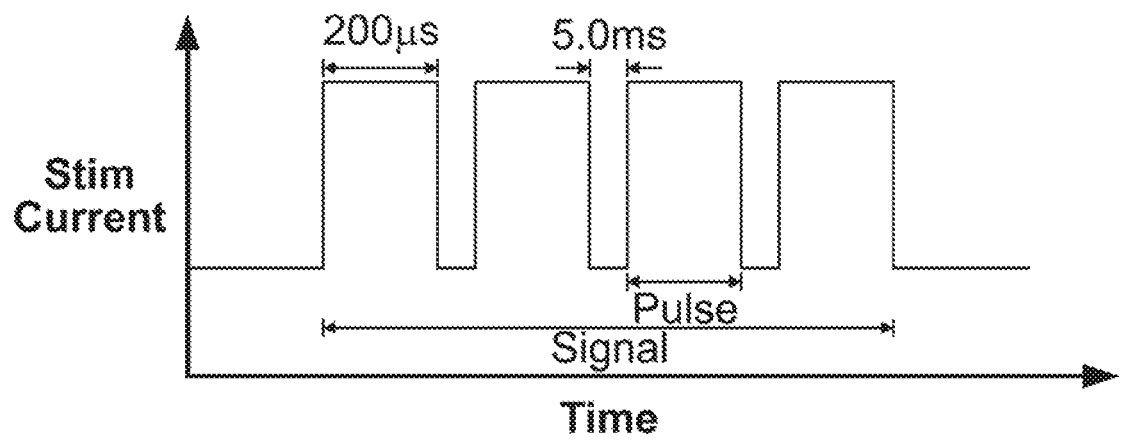
FIG. 4 is a graph illustrating [a] plot of a stimulation current signal comprising a train of pulses capable of producing a neuromuscular response (EMG) of the type shown in FIG. 5.
Figure 5:
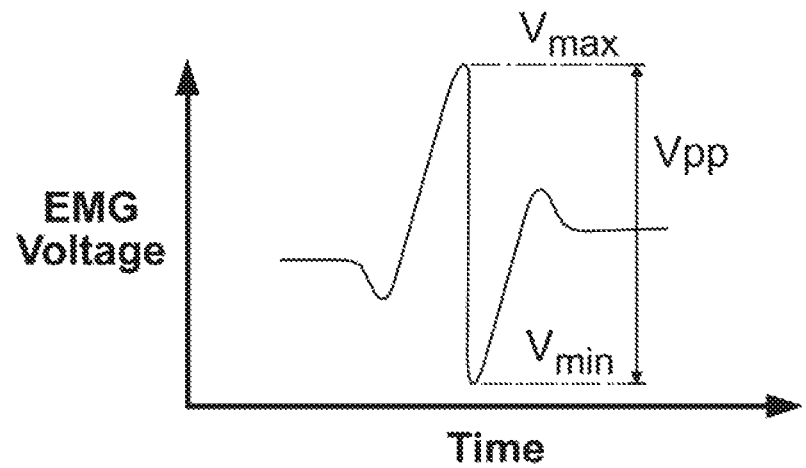
FIG. 5 is a graph illustrating a plot of the neuromuscular response of a given myotome over time based on a stimulation signal (such as shown in either Fit. 4 or FIG. 5)

The basis for performing many of these functional modes (e.g. Twitch Test, Basic Stimulated EMG, Dynamic Stimulated EMG, XILF, MEP Manual, MEP Automatic, TCNR Alert, and TCNR Threshold) is the assessment of evoked responses of the various muscles myotomes monitored by the system 10 in relation to a stimulation signal transmitted by the system 10 (via patient module 14). The assessment of the evoked responses can be any suitable means of sensing physical motion of a muscle, for example via mechanomyography (MMG) which in one embodiment entails using an accelerometer or other similar device for detecting mechanical movement of a muscle or via electromyography (EMG) which is described in detail herein. This is illustrated in FIGS. 3-5, wherein FIG. 5 illustrates the resulting EMG waveform of a monitored myotome in response to one of the example stimulation signals represented in FIG. 3 and FIG. 4. The EMG responses provide a quantitative measure of the nerve depolarization caused by the electrical stimulus. One way to characterize the EMG response is by a peak-to-peak voltage of $V_{pp}=V_{max}-V_{min}$, as shown in FIG. 5. Nerve tissues have characteristic threshold current levels ($I_{thresh}$) at which they will depolarize and result in a detectable muscle activity. Below this threshold current level, a stimulation signal will not evoke a significant EMG response. According to one embodiment, a significant EMG response may be defined as having a $V_{pp}$ of approximately 100 uV. Thus, the lowest stimulation current necessary to evoke an EMG response of the threshold voltage ($V_{thresh}$), 100 uV in this example, may be called $I_{thresh}$. The greater the degree of electrical communication between a stimulation signal and a nerve, the lower $I_{thresh}$ will be. Conversely, the lower the degree of electrical communication between a stimulation signal and a nerve, the greater $I_{thresh}$ will be. Thus determining $I_{thresh}$, and/or monitoring changes in $I_{thresh}$ over time, may provide valuable information when nerve tissues are at risk during a surgical procedure, as will be discussed in more detail below. By way of example, an excessively high $I_{thresh}$ or an increase over a previous measurement during MEP testing may indicate a problem in the spinal cord or other portion of the motor pathway inhibiting transmission (communication) of the stimulation signal to the nerve. Meanwhile, during the Basic Stimulated EMG or Dynamic Stimulated EMG modes and the XLIF mode, a low $I_{thresh}$ value may indicate a breach in the pedicle allowing the electrical signal to transmit through the pedicle, or the close proximity of a nerve to the stimulation source, respectively. Armed with the useful information conveyed by $I_{thresh}$, the surgeon may detect a problem or potential problem early and then act to avoid and/or mitigate the problem. The neurophysiology system 10 may quickly and accurately determine $I_{thresh}$ under the direction and operation of the surgeon (if desired) and convey the useful information $I_{thresh}$ contains in a simple and easily comprehensible manner for interpretation by the surgeon.

Before further addressing the various functional modes of the surgical system 10, the hardware components and features of the system 10 will be describe in further detail. The control unit 12 of the system 10, illustrated by way of example only in FIG. 6, includes a main display 34 and a processing unit 36, which collectively contain the essential processing capabilities for controlling the system 10. The main display 34 is preferably equipped with a graphical user interface (GUI) capable of graphically communicating information to the user and receiving instructions from the user. The processing unit 36 contains computer hardware and software that commands the stimulation source (e.g. patient module 14, FIGS. 7-9), receives digital and/or analog signals and other information from the patient module 14, processes EMG and SSEP response signals, and displays the processed data to the user via the display 34. The primary functions of the software within the control unit 12 include receiving user commands via the touch screen main display 34, activating stimulation in the appropriate mode (Twitch Test, Basic Stimulated EMG, Dynamic Stimulated EMG, XLIF, MEP Manual, MEP Automatic, TCNR Alert, TCNR Threshold, SSEP Manual, and SSEP Automatic), processing signal data according to defined algorithms, displaying received parameters and processed data, and monitoring system status. According to one example embodiment, the main display 34 may comprise a 15" LCD display equipped with suitable touch screen technology and the processing unit 36 may comprise a 2 GHz. The processing unit 36 shown in FIG. 6 further includes a powered USB port 38 for connection to the patient module 14, a media drive 40 (e.g. CD, CD-RW, DVD, DVD-RW, etc. . . . ), a network port, wireless network card, and a plurality of additional ports 42 (e.g. USB, IEEE 1394, infrared, etc. . . . ) for attaching additional accessories, such as for example only, navigated guidance sensors, auxiliary stimulation anodes, and external devices (e.g. printer, keyboard, mouse, etc. . . . ). Preferably, during use the control unit 12 sits near the surgical table but outside the surgical field, such as for example, on a table top or a mobile stand. It will be appreciated, however, that if properly draped and protected, the control unit 12 may be located within the surgical (sterile) field.

Figure 6:
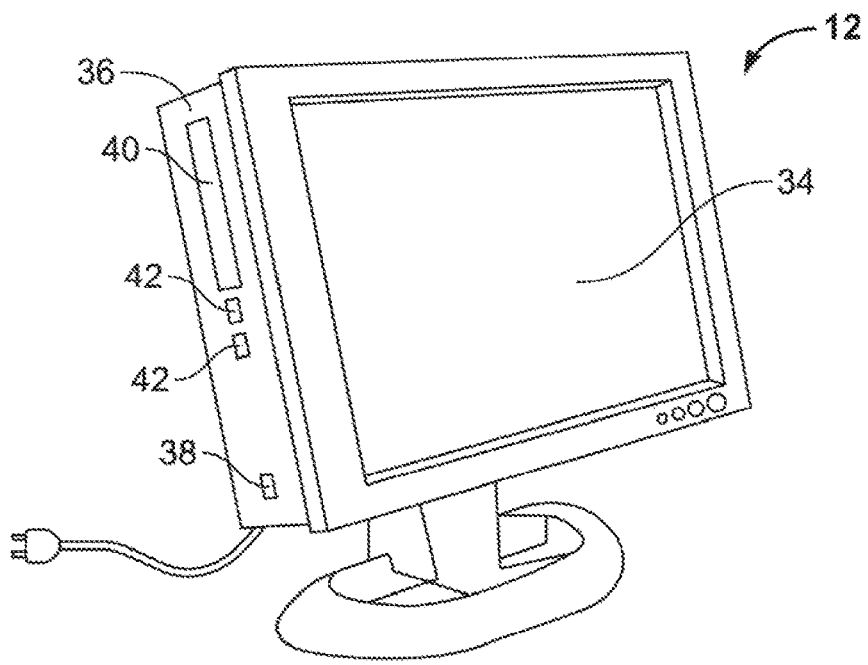
FIG. 6 is a perspective view of an example of a control unit forming part of the system of FIG. 1.

The patient module 14, shown by way of example only in FIGS. 4-6, is communicatively linked to the control unit 12. In this embodiment the patient module 14 is communicatively linked with and receives power from the control unit 12 via a USB data cable 44. However, it will be appreciated that the patient module 14 may be supplied with its own power source and other known data cables, as well as wireless technology, may be utilized to establish communication between the patient module 14 and control unit 12. The patient module 14 contains a digital communications interface to communicate with the control unit 12, as well as the electrical connections to all recording and stimulation electrodes, signal conditioning circuitry, stimulator drive and steering circuitry, and signal conditioning circuitry required to perform all of the functional modes of the system 10, including but not necessarily limited to Twitch Test, Free-run EMG, Basic Stimulated EMG, Dynamic Stimulated EMG, XLIF, MEP Manual and MEP Automatic, TCNR Alert, TCNR Threshold, SSEP Manual, and SSEP Automatic. In one example, the patient module 14 includes thirty-two recording channels and eleven stimulation channels. A display (e.g. an LCD screen) may be provided on the face of the patient module 14, and may be utilized for showing simple status readouts (for example, results of a power on test, the electrode harnesses attached, and impedance data, etc. . . . ) or more procedure related data (for example, a stimulation threshold result, current stimulation level, selected function, etc. . . . ). The patient module 14 may be positioned near the patient in the sterile field during surgery. By way of example, the patient module 14 may be attached to bed rail with the aid of a hook 48 attached to, or forming a part of, the patient module 14 casing.

Figure 7:
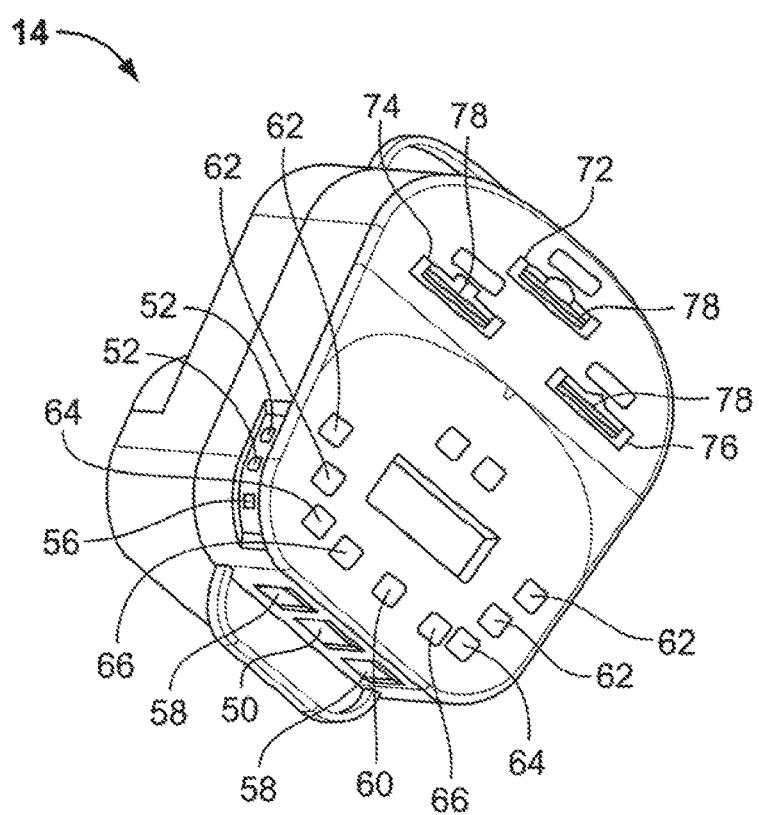
FIGS. 7-9 are perspective, top, and side views, respectively, of an example of a patient module forming part of the system of FIG. 1.
Figure 8:
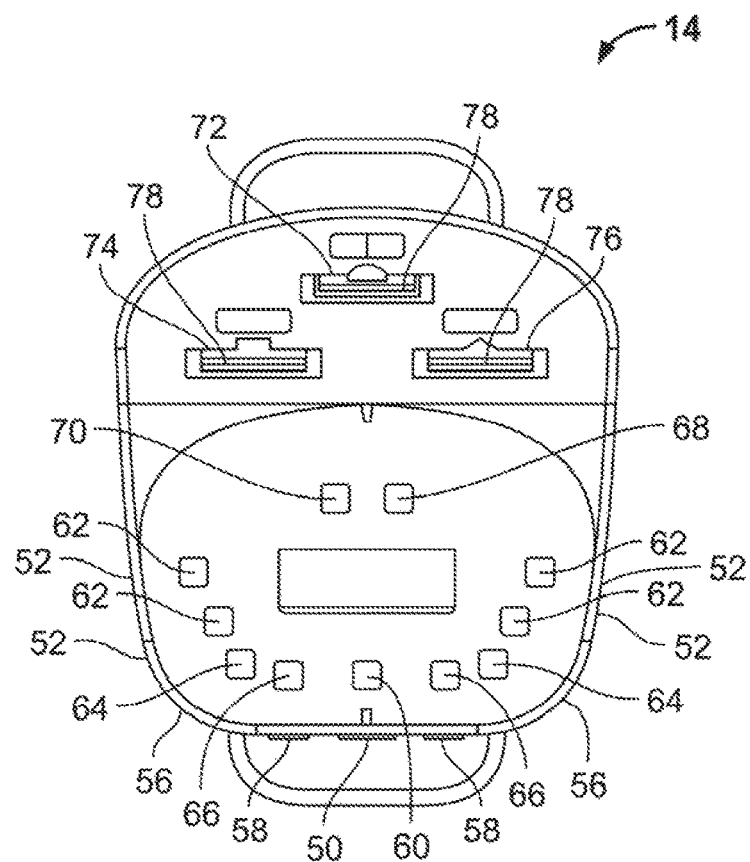
Figure 9:
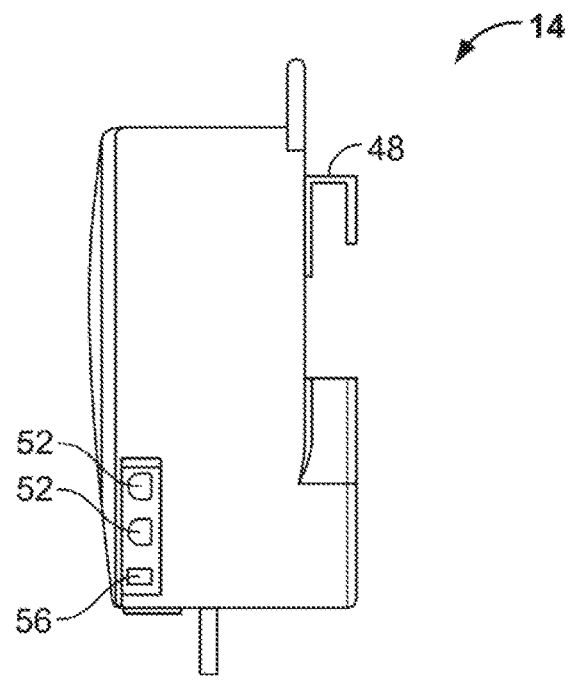

With reference to FIGS. 7-9, patient module 14 comprises a multitude of ports and indicators for connecting and verifying connections between the patient module 14 and other system components. A control unit port 50 is provided for data and power communication with the control unit 12, via USB data cable 44 as previously described. There are four accessory ports 52 provided for connecting up to the same number of surgical accessories, including, but not necessarily limited to, stimulation probe 16, stimulation clip 18, inline stimulation hub 20, and navigated guidance sensor (or tilt sensor) 54. The accessory ports 52 include a stimulation cathode and transmit digital communication signals, tri-color LED drive signals, button status signals, identification signals, and power between the patient module 14 and the attached accessory. A pair of anode ports 56, preferably comprising 2 wire DIN connectors, may be used to attach auxiliary stimulation anodes should it become desirable or necessary to do so during a procedure. A pair of USB ports 58 are connected as a USB hub to the control unit 12 and may be used to make any number of connections, such as for example only, a portable storage drive.

As soon as a device is plugged into any one of ports 50, 52, 56, or 58, the system 10 automatically performs a circuit continuity check to ensure the associated device will work properly. Each device forms a separate closed circuit with the patient module such that the devices may be checked independent of each other. If one device is not working properly the device may be identified individually while the remaining devices continue indicate their valid status. An indicator LED is provided for each port to convey the results of the continuity check to the user. Thus, according to the example embodiment of FIGS. 7-9, the patient module 14 includes one control unit indicator 60, four accessory indicators 62, two anode indicators 64, and two USB indicators 66. According to a preferred embodiment, if the system detects an incomplete circuit during the continuity check, the appropriate indicator will turn red alerting the user that the device might not work properly. On the other hand, if a complete circuit is detected, the indicator will appear green signifying that the device should work as desired. Additional indicator LEDs are provided to indicate the status of the system and the MEP stimulation. The system indicator 68 will appear green when the system is ready and red when the system is not ready. The MEP stim indicator 70 lights up when the patient module is ready to deliver and MEP stimulation signal. In one embodiment, the MEP stim indicator 68 appears yellow to indicate a ready status.

To connect the array of recording electrodes 24 and stimulation electrodes 22 utilized by the system 10, the patient module 14 also includes a plurality of electrode harness ports. In the embodiment shown, the patient module 14 includes an EMG/MEP harness port 72, SSEP harness port 74, an Auxiliary harness port 76 (for expansion and/or custom harnesses; e.g. a TCNR harness). Each harness port 72, 74, and 76 includes a shaped socket 78 that corresponds to a matching shaped connector 82 on the appropriate electrode harness 80. In addition, the system 10 may preferably employ a color code system wherein each modality (e.g. EMG, EMG/MEP, and SSEP) has a unique color associated with it. By way of example only and as shown herein, EMG monitoring (including, screw tests, detection, and nerve retractor) may be associated with the color green, MEP monitoring with the color blue, and SSEP monitoring may be associated with the color orange. Thus, each harness port 72, 74, 76 is marked with the appropriate color which will also correspond to the appropriate harness 80. Utilizing the combination of the dedicated color code and the shaped socket/connector interface simplifies the setup of the system, reduces errors, and can greatly minimize the amount of pre-operative preparation necessary. The patient module 14, and especially the configuration of quantity and layout of the various ports and indicators, has been described according to one example embodiment of the present invention. It should be appreciated, however, that the patient module 14 could be configured with any number of different arrangements without departing from the scope of the invention.

Figure 10:
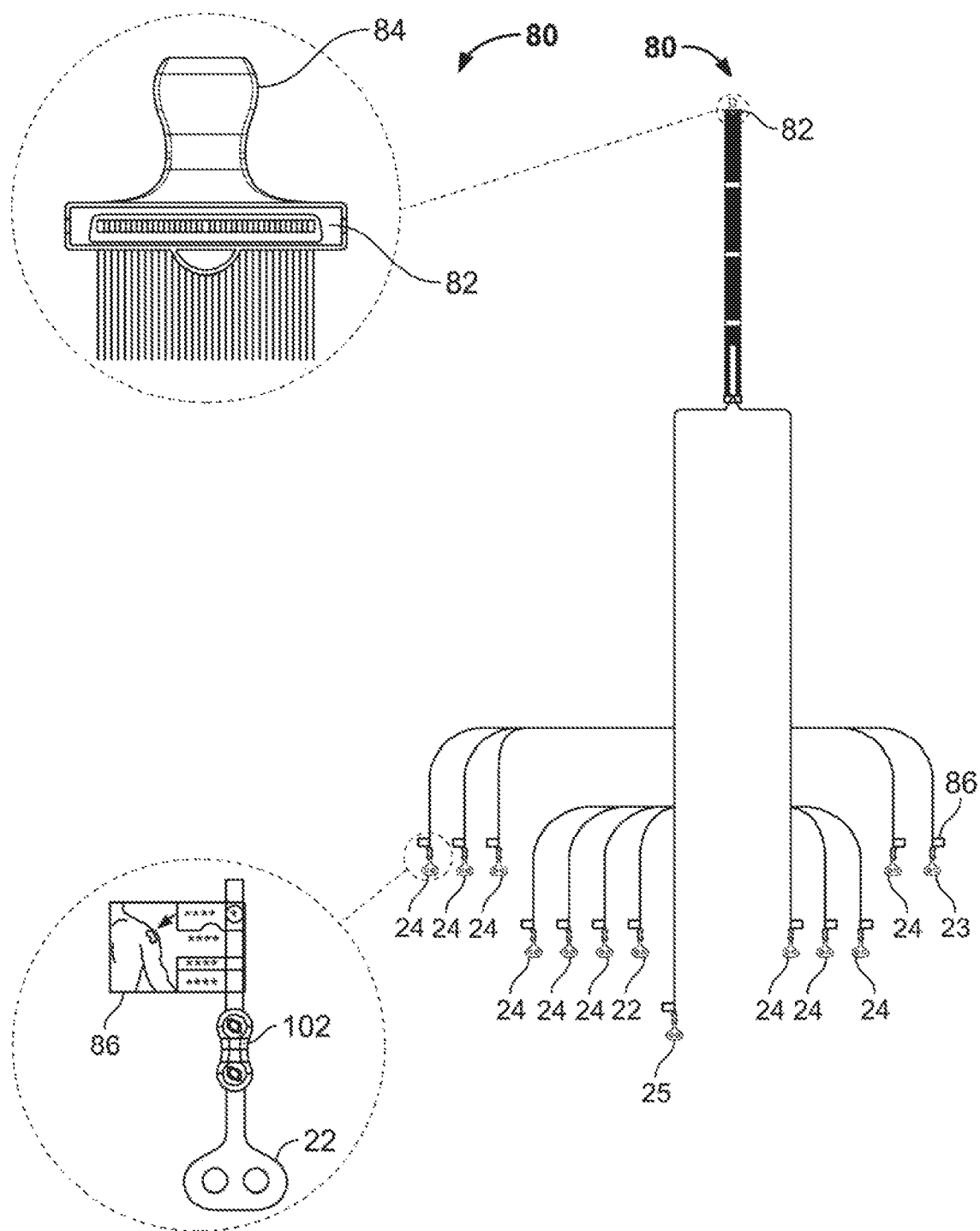
FIG. 10 is a top view of an electrode harness forming part of the system of FIG. 1.

As mentioned above, to simplify setup of the system 10, all of the recording electrodes 24 and stimulation electrodes 22 that are required to perform one of the various functional modes (including a common electrode 23 providing a ground reference to pre-amplifiers in the patient module 14, and an anode electrode 25 providing a return path for the stimulation current) are bundled together and provided in single electrode harness 80, as illustrated, by way of example only, in FIG. 10. Depending on the desired function or functions to be used during a particular procedure, different groupings of recoding electrodes 24 and stimulation electrodes 22 may be required. By way of example, the SSEP function requires more stimulating electrodes 22 than either the EMG or MEP functions, but also requires fewer recording electrodes than either of the EMG and MEP functions. To account for the differing electrode needs of the various functional modes, the system 10 may employ different harnesses 80 tailored for the desired modes. According to one embodiment, three different electrode harnesses 80 may be provided for use with the system 10, an EMG harness, an EMG/MEP harness, and an SSEP harness.

Figure 11A:
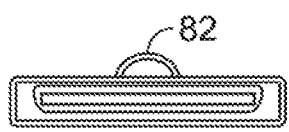
FIGS. 11A-11C are side views of various examples of harness ports forming part of the system of FIG. 1.
Figure 11B:
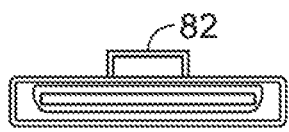
Figure 11C:

At one end of the harness 80 is the shaped connector 82. As described above, the shaped connector 82 interfaces with the shaped socket 72, 74, or 76 (depending on the functions harness 80 is provided for). Each harness 80 utilizes a shaped connector 82 that corresponds to the appropriate shaped socket 72, 74, 76 on the patient module 14. If the shapes of the socket and connector do not match the harness 80, connection to the patient module 14 cannot be established. According to one embodiment, the EMG and the EMG/MEP harnesses both plug into the EMG/MEP harness port 72 and thus they both utilize the same shaped connector 82. By way of example only, FIGS. 11A-11C illustrate the various shape profiles used by the different harness ports 72, 74, 76 and connectors 82. FIG. 11A illustrates the half circular shape associated with the EMG and EMG/MEP harness and port 72. FIG. 11B illustrates the rectangular shape utilized by the SSEP harness and port 74. Finally, FIG. 11C illustrates the triangular shape utilized by the Auxiliary harness and port 76. Each harness connector 82 includes a digital identification signal that identifies the type of harness 80 to the patient module 14. At the opposite end of the electrode harness 80 are a plurality of electrode connectors 102 linked to the harness connector 82 via a wire lead. Using the electrode connector 102, any of a variety of known electrodes may be used, such as by way of example only, surface dry gel electrodes, surface wet gel electrodes, and needle electrodes.

Figure 13A:
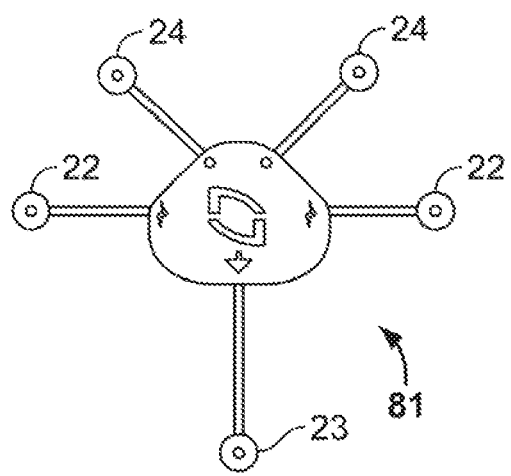
FIGS. 13A-13B are top views of examples of electrode caps forming part of the system of FIG. 1.
Figure 13B:
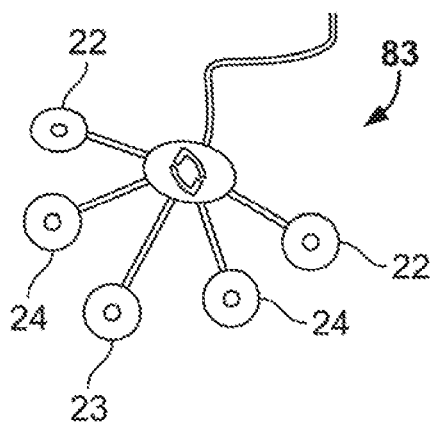

To facilitate easy placement of scalp electrodes used during MEP and SSEP modes, an electrode cap 81, depicted by way of example only in FIG. 13A may be used. The electrode cap 81 includes two recording electrodes 23 for SSEP monitoring, two stimulation electrodes 22 for MEP stimulation delivery, and an anode 23. Graphic indicators may be used on the electrode cap 81 to delineate the different electrodes. By way of example, lightning bolts may be used to indicate a stimulation electrode, a circle within a circle may be used to indicate recording electrodes, and a stepped arrow may be used to indicate the anode electrode. The anode electrode wire is colored white to further distinguish it from the other electrodes and is significantly longer that the other electrode wires to allow placement of the anode electrode on the patient's shoulder. The shape of the electrode cap 81 may also be designed to simplify placement. By way of example only, the cap 81 has a pointed end that may point directly toward the patient's nose when the cap 81 is centered on the head in the right orientation. A single wire may connect the electrode cap 81 to the patient module 14 or electrode harness 80, thereby decreasing the wire population around the upper regions of the patient. Alternatively, the cap 81 may be equipped with a power supply and a wireless antenna for communicating with the system 10. FIG. 13B illustrates another example embodiment of an electrode cap 83 similar to cap 81. Rather than using graphic indicators to differentiate the electrodes, colored wires may be employed. By way of example, the stimulation electrodes 22 are colored yellow, the recording electrodes 24 are gray, and the anode electrode 23 is white. The anode electrode is seen here configured for placement on the patient's forehead. According to an alternate embodiment, the electrode cap (not shown) may comprise a strap or set of straps configured to be worn on the head of the patient. The appropriate scalp recording and stimulation sites may be indicated on the straps. By way of example, the electrode cap may be imbued with holes overlying each of the scalp recording sites (for SSEP) and scalp stimulation sites (for MEP). According to a further example embodiment, the border around each hole may be color coded to match the color of an electrode lead wire designated for that site. In this instance, the recording and stimulation electrodes designated for the scalp are preferably one of a needle electrode and a corkscrew electrode that can be placed in the scalp through the holes in the cap.

Figure 12:
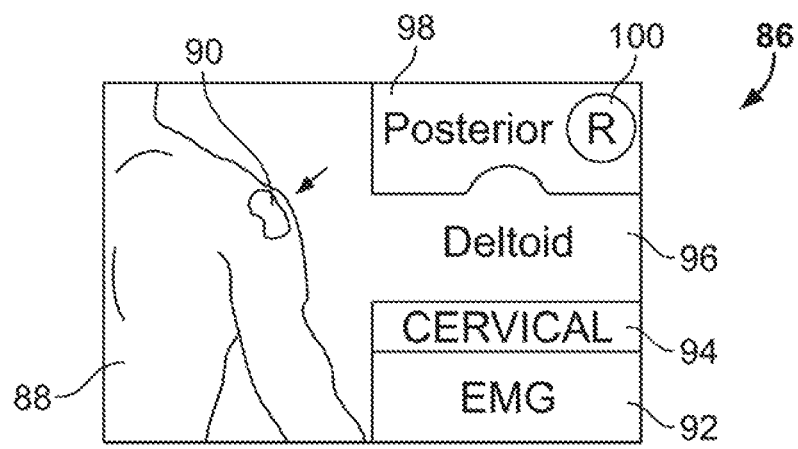
FIG. 12 is a plan view of an example of a label affixed to an electrode connector forming part of the system of FIG. 1.

In addition to or instead of color coding the electrode lead wires to designated intended placement, the end of each wire lead next to the electrode connector 102 may be tagged with a label 86 that shows or describes the proper positioning of the electrode on the patient. The label 86 preferably demonstrates proper electrode placement graphically and textually. As shown in FIG. 12, the label may include a graphic image showing the relevant body portion 88 and the precise electrode position 90. Textually, the label 86 may indicate the side 100 and muscle (or anatomic location) 96 for placement, the function of the electrode (e.g. stimulation, recording channel, anode, and reference—not shown), the patient surface (e.g. anterior or posterior), the spinal region 94, and the type of monitoring 92 (e.g. EMG, MEP, SSEP, by way of example, only). According to one embodiment (set forth by way of example only), the electrode harnesses 80 are designed such that the various electrodes may be positioned about the patient (and preferably labeled accordingly) as described in Table 1 for Lumbar EMG, Table 2 for Cervical EMG, Table 3 for Lumbar/Thoracolumbar EMG and MEP, Table 4 for Cervical EMG and MEP, Table 5 for TCNR, and Table 6 for SSEP:

TABLE 1

| Lumbar EMG | | |
|---|---|---|
| Electrode Type | Electrode Placement | Spinal Level |
| Ground | Upper Outer Thigh | — |
| Anode | Latissimus Dorsi | — |
| Stimulation | Knee | — |

TABLE 1-continued

Lumbar EMG

| Electrode Type | Electrode Placement | Spinal Level |
|---|---|---|
| Recording | Left Tibialis Anterior | L4, L5 |
| Recording | Left Gastroc. Medialis | S1, S2 |
| Recording | Left Vastus Medialis | L2, L3, L4 |
| Recording | Left Biceps Femoris | L5, S1, S2 |
| Recording | Right Biceps Femoris | L5, S1, S2 |
| Recording | Right Vastus Medialis | L2, L3, L4 |
| Recording | Right Gastroc. Medialis | S1, S2 |
| Recording | Right Tibialis Anterior | L4, L5 |

TABLE 2

Cervical EMG

| Electrode Type | Electrode Placement | Spinal Level |
|---|---|---|
| Ground | Shoulder | — |
| Anode | Mastoid | — |
| Stimulation | Inside Elbow | — |
| Recording | Left Triceps | C7, C8 |
| Recording | Left Flexor Carpi Radialis | C6, C7, C8 |
| Recording | Left Deltoid | C5, C6 |
| Recording | Left Trapezius | C3, C4 |
| Recording | Left Vocal Cord | RLN |
| Recording | Right Vocal Cord | RLN |
| Recording | Right Trapezius | C3, C4 |
| Recording | Right Deltoid | C5, C6 |
| Recording | Right Flexor Carpi Radialis | C6, C7, C8 |
| Recording | Right Triceps | C7, C8 |

TABLE 3

Lumbar/Thoracolumbar EMG + MEP

| Electrode Type | Electrode Placement | Spinal Level |
|---|---|---|
| Ground | Upper Outer Thigh | — |
| Anode | Latissimus Dorsi | — |
| Stimulation | Knee | — |
| Recording | Left Tibialis Anterior | L4, L5 |
| Recording | Left Gastroc. Medialis | S1, S2 |
| Recording | Left Vastus Medialis | L2, L3, L4 |
| Recording | Left Biceps Femoris | L5, S1, S2 |
| Recording | Left APB-ADM | C6, C7, C8, T1 |
| Recording | Right APB-ADM | C6, C7, C8, T1 |
| Recording | Right Biceps Femoris | L5, S1, S2 |
| Recording | Right Vastus Medialis | L2, L3, L4 |
| Recording | Right Gastroc. Medialis | S1, S2 |
| Recording | Right Tibialis Anterior | L4, L5 |

TABLE 4

Cervical EMG + MEP

| Electrode Type | Electrode Placement | Spinal Level |
|---|---|---|
| Ground | Shoulder | — |
| Anode | Mastoid | — |
| Stimulation | Inside Elbow | — |
| Recording | Left Tibialis Anterior | L4, L5 |
| Recording | Left Flexor Carpi Radialis | C6, C7, C8 |
| Recording | Left Deltoid | C5, C6 |
| Recording | Left Trapezius | C3, C4 |
| Recording | Left APB-ADM | C6, C7, C8, T1 |
| Recording | Left Vocal Cord | RLN |
| Recording | Right Vocal Cord | RLN |
| Recording | Right APB-ADM | C6, C7, C8, T1 |
| Recording | Right Trapezius | C3, C4 |
| Recording | Right Deltoid | C5, C6 |
| Recording | Right Flexor Carpi Radialis | C6, C7, C8 |
| Recording | Right Tibialis Anterior | L4, L5 |

TABLE 5

Transcutaneous Nerve Root Stimulation

| Electrode Type | Electrode Placement | Spinal Level |
|---|---|---|
| Ground | Hip | — |
| Anode | Mid-back | — |
| Stimulation | L1-L2 cathode | — |
| Stimulation | Umbilicus anode | — |
| Recording | Left Adductor Magnus | L2, L3, L4 |
| Recording | Left Vastus Lateralis | L3, L4 |
| Recording | Left Tibialis Anterior | L4, L5 |
| Recording | Left Biceps Femoris | L5, S1, S2 |
| Recording | Right Adductor Magnus | L2, L3, L4 |
| Recording | Right Vastus Lateralis | L3, L4 |
| Recording | Right Vastus Medialis | L2, L3, L4 |
| Recording | Right Tibialis Anterior | L4, L5 |
| Recording | Right Biceps Femoris | L5, S1, S2 |

TABLE 6

SSEP

| Electrode Type | Electrode Placement | Spinal Level |
|---|---|---|
| Ground | Shoulder | — |
| Stimulation | Left Post Tibial Nerve | — |
| Stimulation | Left Ulnar Nerve | — |
| Stimulation | Right Post Tibial Nerve | — |
| Stimulation | Right Ulnar Nerve | — |
| Recording | Left Popliteal Fossa | — |
| Recording | Left Erb's Point | — |
| Recording | Left Scalp Cp3 | — |
| Recording | Right Popliteal Fossa | — |
| Recording | Right Erb's Point | — |
| Recording | Right Scalp Cp4 | — |
| Recording | Center Scalp Fpz | — |
| Recording | Center Scalp Cz | — |
| Recording | Center Cervical Spine | — |

Figure 14A:
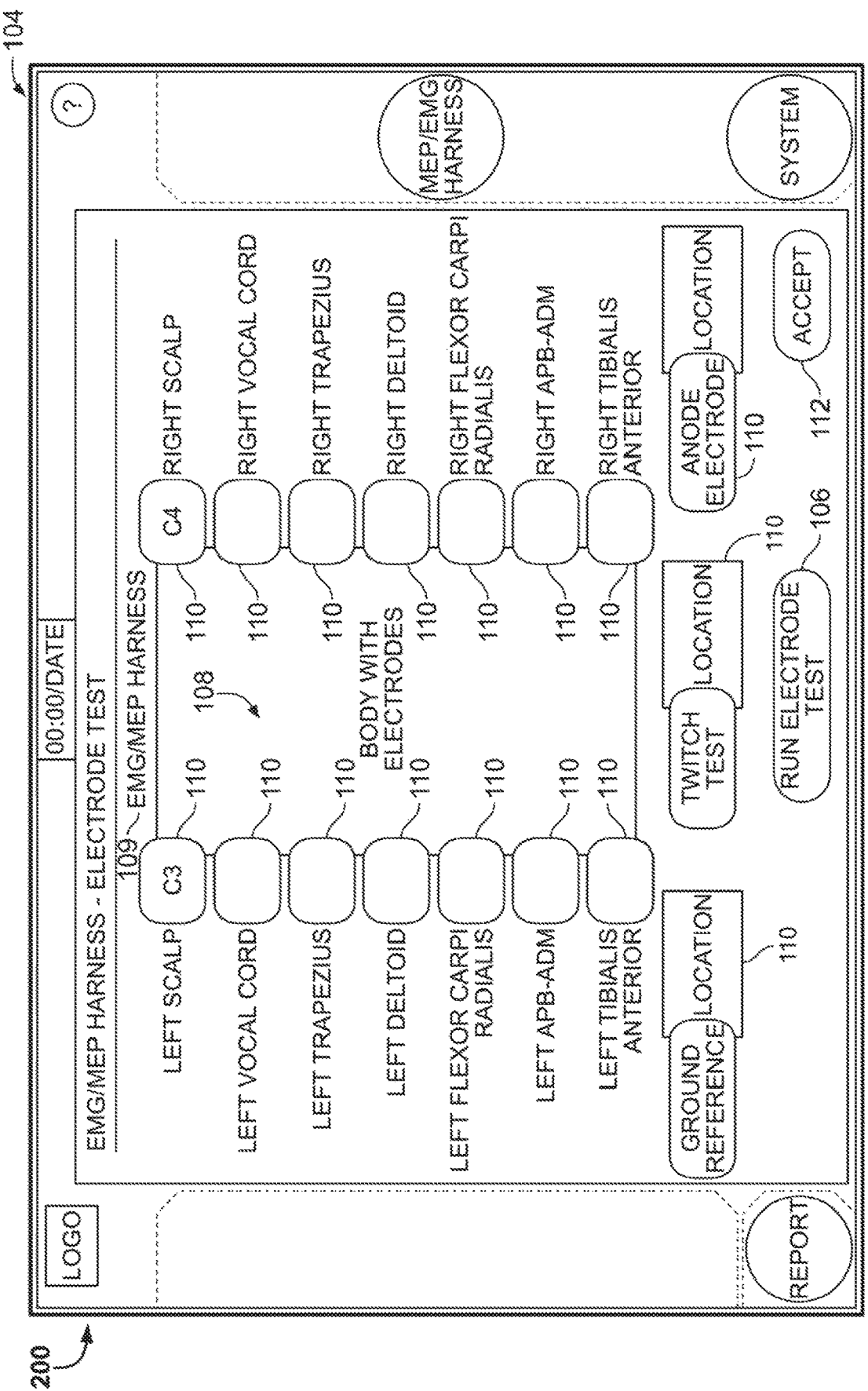
FIGS. 14A-14B are screenshots of an example embodiment of an electrode test screen forming part of the system of FIG. 1.
Figure 14B:
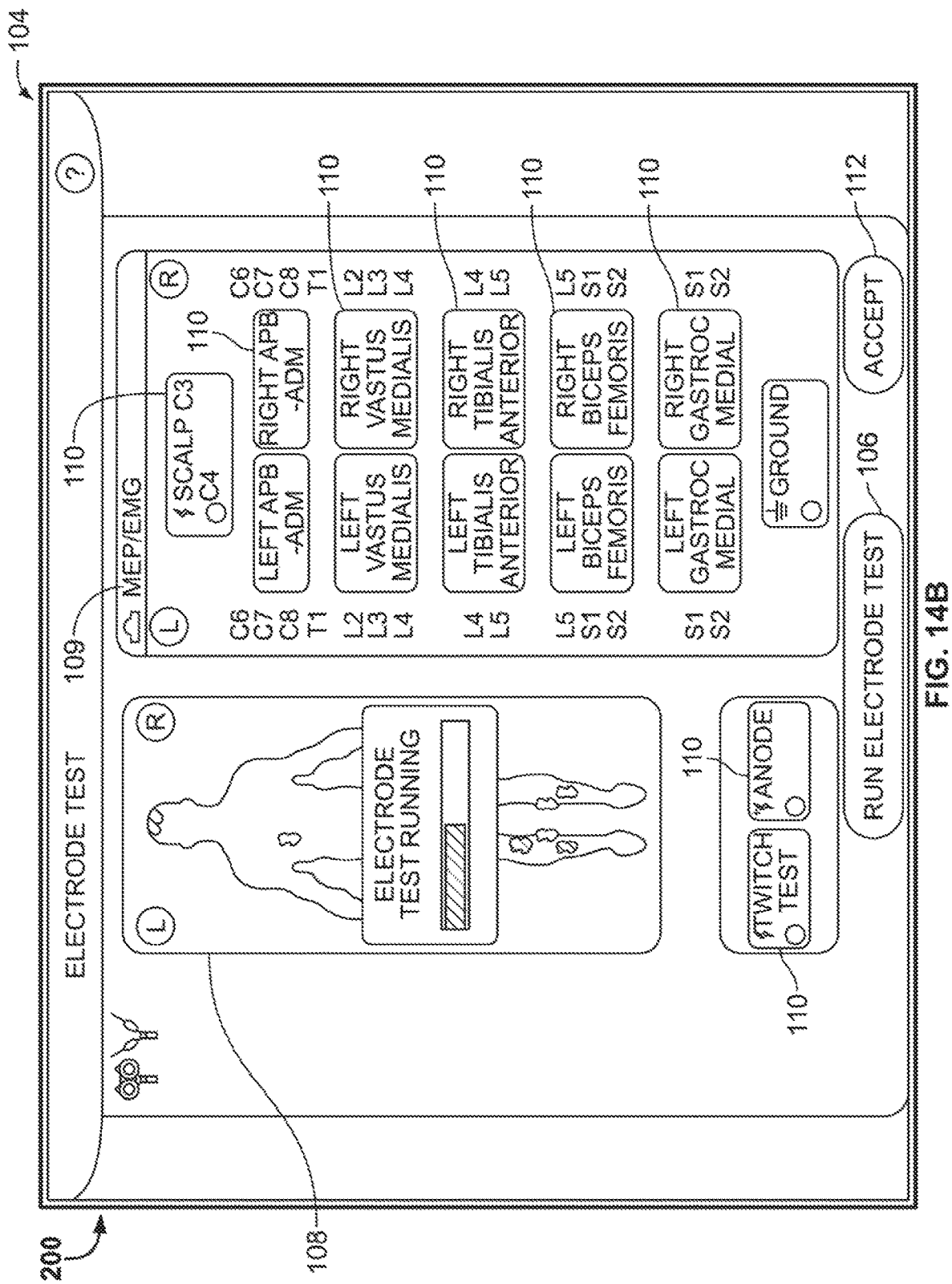

The patient module 14 is configured such that the system 10 may conduct an impedance test under the direction of the control unit 12 of all electrodes once the system is set up and the electrode harness is connected and applied to the patient. After choosing the appropriate spinal site upon program startup (described below), the user is directed to an electrode test. FIGS. 14A-14B illustrate, by way of example only, a graphical implementation capturing the features of an electrode test[s] as implemented on an electrode test screen 104. The electrode test screen 104 includes a human figure depiction with positioned electrodes 108. A harness indicator 109 displays which harness is in use. For each electrode on the harness 80 in use there is a channel button 110. This includes the common 25 and anode 23 electrodes which are both independently checked for impedance. To accomplish this, the anode 23 and common 25 are both provided as dual electrodes. At least one of the anode leads on the anode electrode is reversible. During the impedance check, the reversible anode lead switches to a cathode such that the impedance between the leads can be measured. When the impedance test is complete, the reversible lead switches back to an anode. The channel button 110 may be labeled with the muscle or coverage area of the corresponding electrode. Selecting the channel button 110 will disable the channel. Disabled channels will not be tested for impedance and they will not be monitored for responses or errors unless reactivated. Upon selection of a start button 106 ("Run Electrode Test"), the system tests each electrode individually to determine the impedance value. If the impedance is determined to be within acceptable limits, the channel button 110 and electrode depiction on the human FIG. 108 turn green. If the impedance value for any electrode is not determined to be acceptable, the associated channel button 110 and electrode depiction turn red, alerting the user. Once the test is complete, selecting the "Accept" button 112 will open the main monitoring screen 200 of the system 10.

Figure 15:
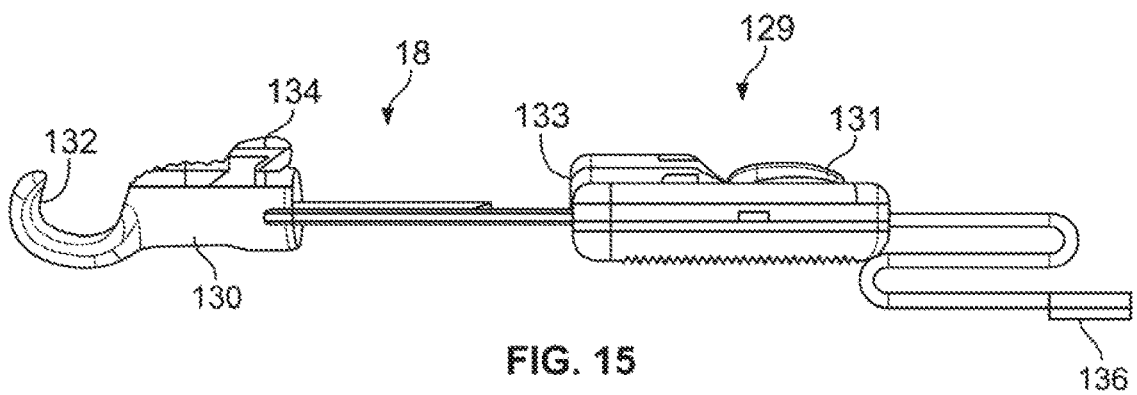
FIG. 15 is a perspective view of one embodiment of a stimulator forming part of the system of FIG. 1.
Figure 16:
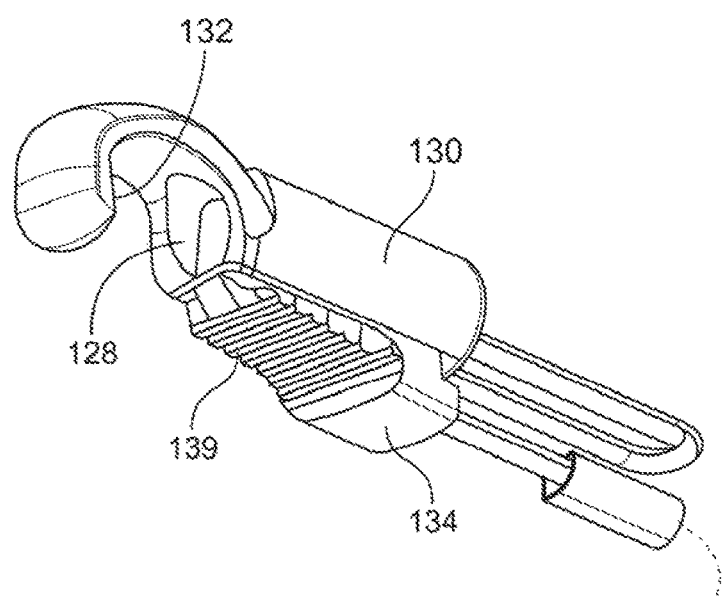
FIG. 16 is a perspective view of a second embodiment of a stimulator forming part of the system of FIG. 1.
Figure 17:
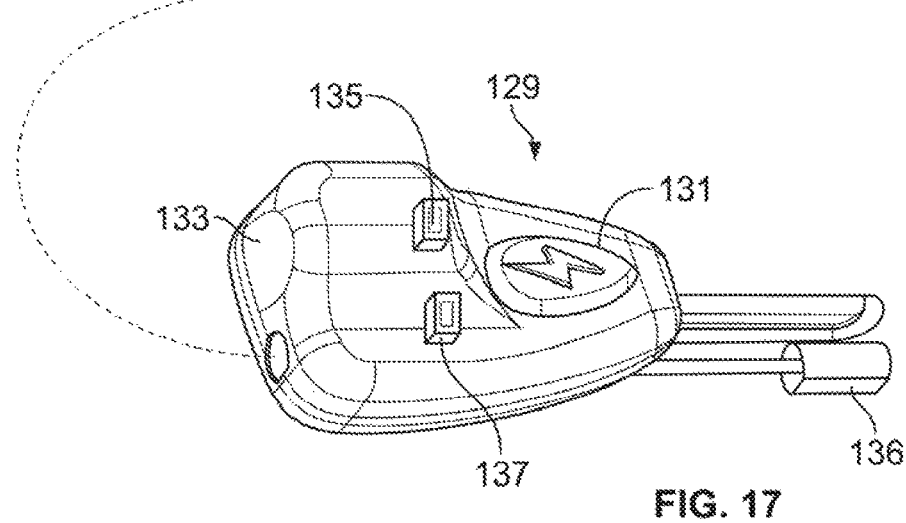
FIG. 17 is a perspective view of the stimulators of FIGS. 15 and 16 coupled together for use.

The system 10 may utilize various stimulation accessories to deliver stimulation signals to a stimulation target site such as over the patient's conus medullaris, a hole formed or being formed in a pedicle, and/or tissue surrounding an access corridor. FIGS. 15-17 illustrate an example embodiment of a stimulation accessory in the form of a stimulation clip 18 that permits the system 10 to deliver stimulation signals through various surgical instruments already used during the surgical procedure. By way of example only, the coupling device 18 may connect the system 10 with instruments including, but not necessarily limited to, a pedicle access needle 26, a tap 28, dilator 30, tissue retractor 32, and k-wire 27. The stimulation clip 18 utilizes a spring-loaded plunger 128 to hold the surgical tool and transmit the stimulation signal thereto. The plunger 128 is composed of a conductive material such as metal. A nonconductive housing 130 partially encases the plunger 128 about its center. Extending from the housing 130 is an endplate 132 that hooks the surgical instrument. A spring (not shown) is disposed within the housing 130 such that in a natural or "closed" state, the plunger 128 is situated in close proximity to the endplate 132. Exerting a compressive force on the spring (such as by pulling on the thumb grip 134) causes a gap between the end plate 132 and the plunger 128 to widen to an "open" position (shown in FIGS. 15-17 thereby allowing insertion of a surgical tool between the endplate 132 and plunger 128. Releasing the thumb grip 134 allows the spring to return to a "closed" position, causing the plunger 132 to move laterally back towards the endplate such that a force is exerted upon the surgical instrument and thereby holding it in place between the endplate 132 and the plunger 128. The clip 18 further includes a button module 129 containing an activation button 131 for initiating stimulation. The button module 129 is set apart from the body of the clip 18 and they are linked by an integrated wire. An accessory port 133 is located next to the button 131 on the button module 129, thus minimizing the number of wires connecting back to the patient module 14 and outside the sterile field. Clip 18 is equipped with three LEDs 135, 137, and 139. LED 135 is associated with the accessory port 133 and LED 137 is associated with the clip 18 to indicate which of the two is stimulating. The LEDs 137 and 137 may appear purple when stimulation is active. When a stimulation result is determined, the associated LED 135 or 137 may appear either red (if the result meets a predetermined potentially unsafe value), green (if the result meets a predetermined safe value), or yellow (if the result is in between the safe and potentially unsafe values). A third LED 139 is contained within the thumb grip 134, which will appear red, yellow, or green depending on the threshold result. The clip 18 connects to one of the accessory ports 62 on the patient module 14 via a connector 136. The connector 136 includes an identification signal that identifies it to the patient module.

Figure 18:
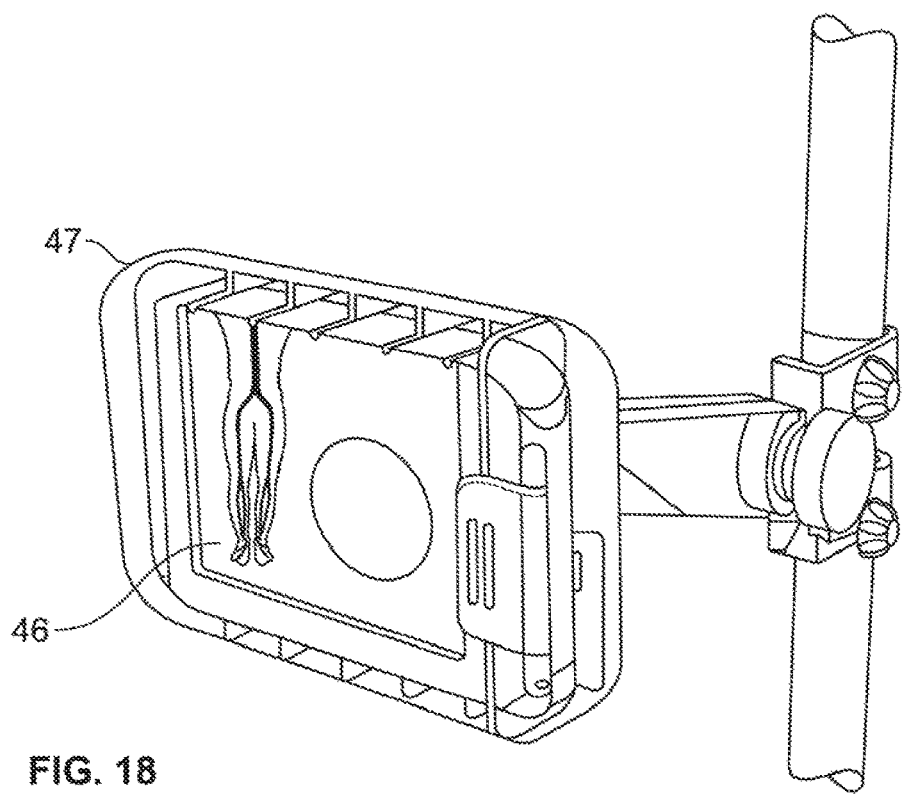
FIGS. 18-19 are perspective views of an example of a secondary display forming part of the system of FIG. 1.
Figure 19:
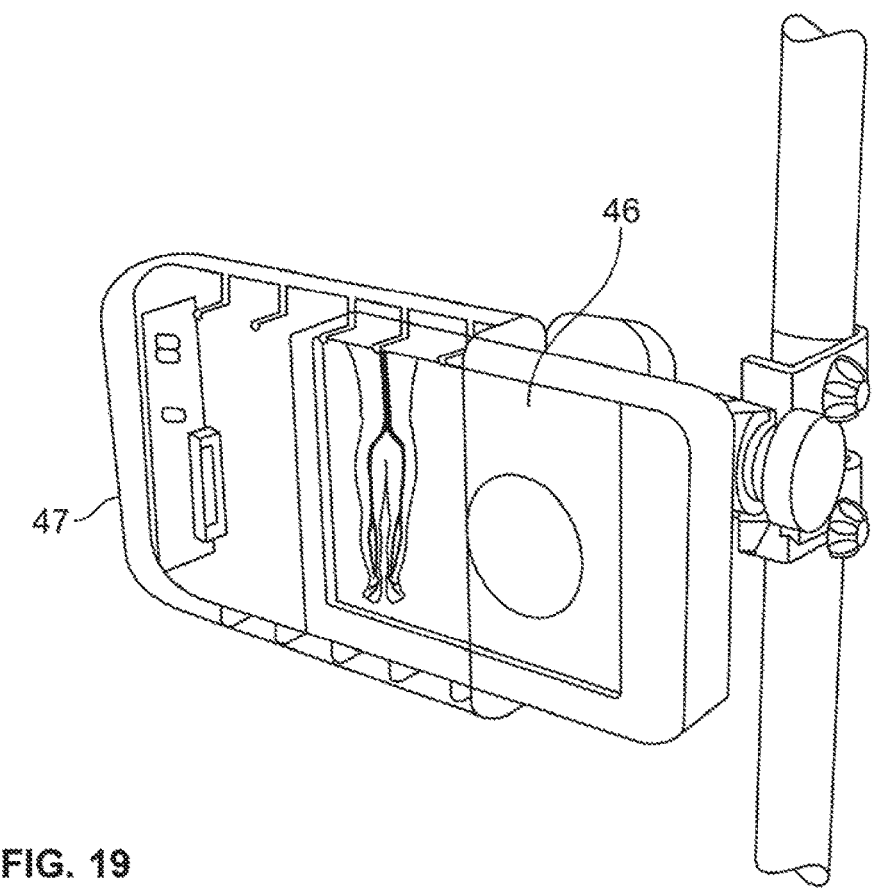

As mentioned above, the system 10 may include a secondary display, such as for example only, the secondary display 46 illustrated in FIGS. 18-19. The secondary display 46 may be configured to display some or all of the information provided on main display 34. The information displayed to the user on the secondary display 34 may include, but is not necessarily limited to, alpha-numeric and/or graphical information regarding any of the selected function modes (e.g. Twitch Test, Free-Run EMG, Basic Stimulated EMG, Dynamic Stimulated EMG, XLIF, MEP Manual, MEP Automatic, TCNR Alert, TCNR Threshold, SSEP Manual, SSEP Automatic, and surgical correction planning and assessment), attached accessories (e.g. stimulation probe 16, stimulation clip 18, tilt sensor 54), electrode harness or harnesses attached, impedance test results, myotome/EMG levels, stimulation levels, history reports, selected parameters, test results, etc . . . In one embodiment, secondary display 46 may be configured to receive user input in addition to its display function. The secondary display 46 can thus be used as an alternate control point for the system 10. The control unit 12 and secondary display 46 may be linked such that input may be received on from one display without changing the output shown on the other display. This would allow the surgeon to maintain focus on the patient and test results while still allowing other members of the OR staff to manipulate the system 10 for various purposes (e.g. inputting annotations, viewing history, etc. . . . ). The secondary display 46 may be battery powered. Advantageously, the secondary display 46 may be positioned inside the sterile field as well as outside the sterile field. For positioning within the sterile field a disposable sterile case 47 may be provided to house the display. Alternatively, the display 46 may be sterile bagged. Both the sterile case 47 and the secondary display 46 may be mounted to a pole, bed frame, light fixture, or other apparatus found near and/or in the surgical field. It is further contemplated that multiple secondary displays 46 may be linked to the control unit 12. This may effectively distribute neurophysiology information and control throughout the operating room. By way of example, a secondary display 46 may also be provided for the anesthesiologist. This may be particularly useful in providing the anesthesiologist with results from the Twitch Test and providing reminders about the use of paralytics, which may adversely affect the accuracy of the system 10. Wired or wireless technology may be utilized to link the secondary display 46 to the control unit 12.

Having described an example embodiment of the system 10 and the hardware components that comprise it, the neurophysiological functionality and methodology of the system 10 will now be described in further detail. Various parameters and configurations of the system 10 may depend upon the target location (i.e. spinal region) of the surgical procedure and/or user preference. In one embodiment, upon starting the system 10 the software will open to a startup screen, illustrated by way of example only, in FIG. 20. The startup screen includes a profile selection window 160 from which the user may select from one of the standard profiles (e.g. "Standard Cervical," "Standard Thoracolumbar," and "Standard Lumbar") or any custom profiles that have been previously saved to the system. Profiles may be arranged for selection, alphabetically, by spinal region, or by other suitable criteria. Profiles may be saved to the control unit hard drive or to a portable memory device, such as for example, a USB memory drive, or on a web server.

Selecting a profile configures the system 10 to the parameters assigned for the selected profile (standard or custom). The availability of different function modes may depend upon the profile selected. By way of example only, selecting the cervical and thoracolumbar spinal regions may automatically configure the options to allow selection of the Twitch Test, SSEP Manual, SSEP Automatic, Basic Stimulated EMG, Dynamic Stimulated EMG, XLIF, MEP Manual, MEP Automatic, Free-Run EMG modes, while selecting the lumbar region may automatically configure the options to allow selection of the Twitch Test, Basic, Difference, and Dynamic Stimulated EMG Tests, XLIF®, and Nerve Retractor modes. Default parameters associated with the various function modes may also depend on the profile selected, for example, the characteristics of the stimulation signal delivered by the system 10 may vary depending on the profile. By way of example, the stimulation signal utilized for the Stimulated EMG modes may be configured differently when a lumbar profile is selected versus when one of a thoracolumbar profile and a cervical profile.

As previously described above, each of the hardware components includes an identification tag that allows the control unit 12 to determine which devices are hooked up and ready for operation. In one embodiment, profiles may only be available for selection if the appropriate devices (e.g. proper electrode harness 80 and stimulation accessories) are connected and/or ready for operation. Alternatively, the software could bypass the startup screen and jump straight to one of the functional modes based on the accessories and/or harnesses it knows are plugged in. The ability to select a profile based on standard parameters, and especially on customized preferences, may save significant time at the beginning of a procedure and provides for monitoring availability right from the start. Moving on from the startup screen, the software advances directly to an electrode test screen and impedance tests, which are performed on every electrode as discussed above. When an acceptable impedance test has been completed, the system 10 is ready to begin monitoring and the software advances to a monitoring screen from which the neurophysiological monitoring functions of the system 10 are performed.

The information displayed on the monitoring screen may include, but is not necessarily limited to, alpha-numeric and/or graphical information regarding any of the functional modes (e.g. Twitch Test, Free-Run EMG, Basic Stimulated EMG, Dynamic Stimulated EMG, XLIF, MEP Manual, MEP Automatic, TCNR Alert, TCNR Threshold, SSEP Manual, SSEP Automatic, and surgical correction planning and assessment), attached accessories (e.g. stimulation probe 16, stimulation clip 18, tilt sensor 54), electrode harness or harnesses attached, impedance test results, myotome/EMG levels, stimulation levels, history reports, selected parameters, test results, etc. . . . In one embodiment, set forth by way of example only, this information displayed on a main monitoring screen may include, but is not necessarily limited to, the following components as set forth in Table 8:

TABLE 8

| Screen Component | Description |
| --- | --- |
| Patient Image/ Electrode layout | An image of the human body or relevant portion thereof showing the electrode placement on the body, with labeled channel number tabs on each side (1-4 on the left and right). Left and right labels will show the patient orientation. The channel number tabs may be highlighted or colored depending on the specific function being performed. |
| Myotome & Level Names | A label to indicate the Myotome name and corresponding Spinal Level(s) associated with the channel of interest. |
| Test Menu | A hideable menu bar for selecting between the available functional modes. |
| Device Bar | A hideable bar displaying icons and/or names of devices connected to the patient module. |
| Display Area | Shows procedure-specific information including stimulation results. |
| Color Indication | Enhances stimulation results with a color display of green, yellow, or red corresponding to the relative safety level determined by the system. |
| Stimulation Bar | A graphical stimulation indicator depicting the present stimulation status (i.e. on or off and stimulation current level), as well as providing for starting and stopping stimulation |
| Event Bar | A hideable bar that shows the last up to a selected number of previous stimulation results, provides for annotation of results, and a chat dialogue box for communicating with remote participants. |
| EMG waveforms | EMG waveforms may be optionally displayed on screen along with the stimulation results. |

From a profile setting window 160, custom profiles can be created and saved. Beginning with one of the standard profiles, parameters may be altered by selecting one of the various buttons and making the changes until the desired parameters are set. By way of example only, profiles may be generated and saved for particular procedures (e.g. ACDF, XLIF, and decompression), particular individuals, and combinations thereof. Clicking on each button will display the parameter options specific to the selected button in a parameter window. The parameter options for the Test Selection Window are illustrated by way of example in FIG. 20. By way of example only, by selecting the Test Selection button, session tests may be added and viewing options may be changed. From within the test selection area, function specific parameters for all available test functions (based on site selection, available devices, etc . . . ) may be accessed and set according to need. One option (not shown) that is available for multiple functions under the test selection button is the ability to select from three different viewing options. The user may choose to see results displayed in numeric form, on a body panel, and on a label that reflects the labels associated with each electrode, or any combination of the three. FIGS. 21-32 illustrate examples of the test selection tab 204 for each of the test functions (e.g. Twitch Test, Basic Stimulated EMG, Dynamic Stimulated EMG, XLIF, TCNR Alert, TCNR Threshold, Free-Run, MEP Manual, MEP Automatic, SSEP Manual, SSEP Automatic). Profiles may be saved directly on the control unit 12, saved to a portable memory device, or uploaded onto a web-server.

The functions performed by the system 10 may include, but are not necessarily limited to, Twitch Test, Basic Stimulated EMG, Dynamic Stimulated EMG, XLIF®, Nerve Retractor, TCNR Alert, TCNR Threshold, Free-run EMG, MEP Manual, MEP Automatic, SSEP Manual, SSEP Automatic, and surgical correction planning and assessment modes, all of which will be described below. The Twitch Test mode is designed to assess the neuromuscular pathway via the so-called "train-of-four-test" to ensure the neuromuscular pathway is free from muscle relaxants prior to performing neurophysiology-based testing, such as bone integrity (e.g. pedicle) testing, nerve detection, and nerve retraction. This is described in greater detail within PCT Patent App. No. PCT/US2005/036089, entitled "System and Methods for Assessing the Neuromuscular Pathway Prior to Nerve Testing," filed Oct. 7, 2005, the entire contents of which is hereby incorporated by reference as if set forth fully herein. The Basic Stimulated EMG Dynamic Stimulated EMG tests are designed to assess the integrity of bone (e.g. pedicle) during all aspects of pilot hole formation (e.g., via an awl), pilot hole preparation (e.g. via a tap), and screw introduction (during and after). These modes are described in greater detail in PCT Patent App. No. PCT/US02/35047 entitled "System and Methods for Performing Percutaneous Pedicle Integrity Assessments," filed on Oct. 30, 2002, and PCT Patent App. No. PCT/US2004/025550, entitled "System and Methods for Performing Dynamic Pedicle Integrity Assessments," filed on Aug. 5, 2004 the entire contents of which are both hereby incorporated by reference as if set forth fully herein. The XLIF mode is designed to detect the presence of nerves during the use of the various surgical access instruments of the system 10, including the pedicle access needle 26, k-wire 42, dilator 44, and retractor assembly 70. This mode is described in greater detail within PCT Patent App. No. PCT/US2002/22247, entitled "System and Methods for Determining Nerve Proximity, Direction, and Pathology During Surgery," filed on Jul. 11, 2002, the entire contents of which is hereby incorporated by reference as if set forth fully herein. The Nerve Retractor mode is designed to assess the health or pathology of a nerve before, during, and after retraction of the nerve during a surgical procedure. This mode is described in greater detail within PCT Patent App. No. PCT/US2002/30617, entitled "System and Methods for Performing Surgical Procedures and Assessments," filed on Sep. 25, 2002, the entire contents of which are hereby incorporated by reference as if set forth fully herein. The MEP Manual and Automatic modes are designed to test the motor pathway to detect potential damage to the spinal cord by stimulating the motor cortex in the brain and recording the resulting EMG response of various muscles in the upper and lower extremities. The MEP Manual and Automatic modes are described in greater detail within PCT Patent App. No. PCT/US2006/003966, entitled "System and Methods for Performing Neurophysiologic Assessments During Spine Surgery," filed on Feb. 2, 2006, the entire contents of which is hereby incorporated by reference as if set forth fully herein. The TCNR Alert and TCNR Threshold Modes are designed to test potential damage to the lower motor pathway by stimulating trans-abdominally and recording the resulting EMG response of various muscles. The TCNR Alert and Threshold modes are described in greater detail within PCT Patent App. No. PCT/US2014/64449, entitled "Systems and Methods for Performing Neurophysiologic Monitoring During Spine Surgery," filed on Nov. 6, 2014, the entire contents of which is hereby incorporated by reference as if set forth fully herein. The SSEP Manual and SSEP Automatic modes are designed to test the sensory pathway to detect potential damage to the spinal cord by stimulating peripheral nerves inferior to the target spinal level and recording the action potentials superior to the spinal level. The SSEP Manual and SSEP Automatic modes are described in greater detail within PCT Patent App. No. PCT/US2009/05650, entitled "Neurophysiologic Monitoring System and Related Methods," filed on Oct. 15, 2009, the entire contents of which is hereby incorporated by reference as if set forth fully herein. The surgical correction planning and assessment modes are described in greater detail within PCT Patent Application No. PCT/US2014/059974, entitled "Systems for Planning, Performing, and Assessing Spinal Correction during Spine Surgery", the entire contents of which is hereby incorporated by reference as if set forth fully herein. These functions will be explained now in brief detail.

Figure 21:
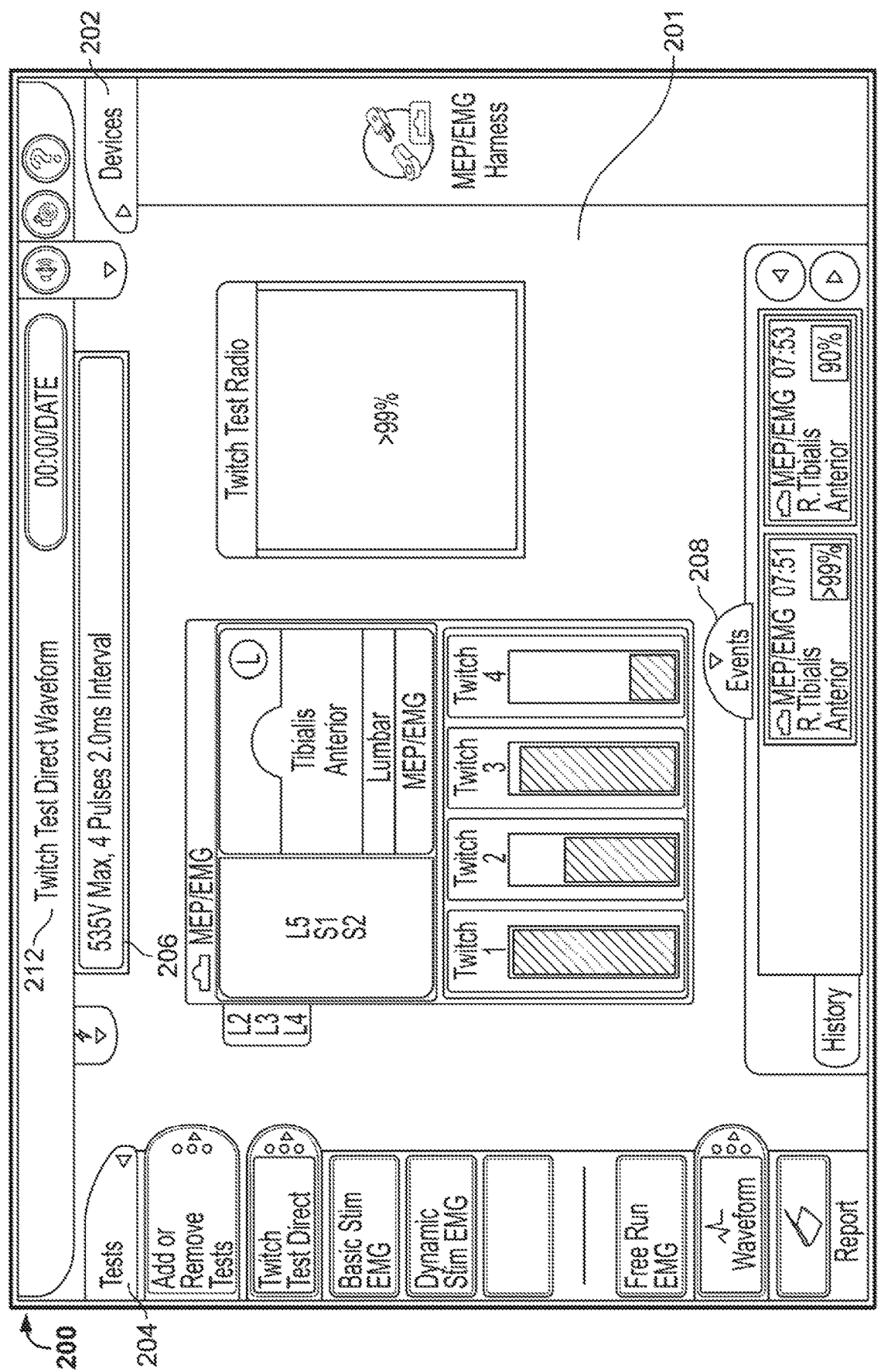
FIG. 21 is a screenshot of an example of a Twitch Test monitoring screen forming part of the system of FIG. 1.

The system 10 performs neuromuscular pathway (NMP) assessments, via Twitch Test mode, by electrically stimulating a peripheral nerve (preferably the Peroneal Nerve for lumbar and thoracolumbar applications and the Median Nerve for cervical applications) via stimulation electrodes 22 contained in the applicable electrode harness and placed on the skin over the nerve or by direct stimulation of a spinal nerve using a surgical accessory such as the probe 116. Evoked responses from the muscles innervated by the stimulated nerve are detected and recorded, the results of which are analyzed and a relationship between at least two responses or a stimulation signal and a response is identified. The identified relationship provides an indication of the current state of the NMP. The identified relationship may include, but is not necessarily limited to, one or more of magnitude ratios between multiple evoked responses and the presence or absence of an evoked response relative to a given stimulation signal or signals. With reference to FIG. 21, details of the test indicating the state of the NMP and the relative safety of continuing on with nerve testing are conveyed to the surgeon via GUI display 34. On the monitoring screen 200 utilized by the various functions performed by the system 10, function specific data is displayed in a center result area 201. The results may be shown as a numeric value 210, a highlighted label corresponding to the electrode labels 86, or (in the case of twitch test only) a bar graph of the stimulation results. On one side of center result area 201 is a collapsible device menu 202. The device menu displays a graphic representation of each device connected to the patient module 14. Opposite the device menu 202 there is a collapsible test menu 204. The test menu 204 highlights each test that is available under the operable setup profile and may be used to navigate between functions. A collapsible stimulation bar 206 indicates the current stimulation status and provides start and stop stimulation buttons (not shown) to activate and control stimulation. The collapsible event bar 208 stores all the stimulation test results obtained throughout a procedure. Clicking on a particular event will open a note box and annotations may be entered and saved with the response for later inclusion in a procedure report. The event bar 208 also houses a chat box feature when the system 10 is connected to a remote monitoring system as described above. Within the result area 202 the twitch test specific results may be displayed.

It should be appreciated that while FIG. 21 depicts the monitoring screen 200 while the selected function is the Twitch Test, the features of monitoring screen 200 apply equally to all the functions. Result-specific data is displayed in a center result area 201. A large color saturated numeric value (not shown) is used to show the threshold result. Three different options are provided for showing the stimulation response level. First, the user can view the waveform. Second, a likeness of the color coded electrode harness label 86 may be shown on the display. Third, the color coded label 212 may be integrated with a body image. On one side of center result area 201 there is a collapsible device menu 202. The device menu displays a graphic representation of each device connected to the patient module 14. If a device is selected from the device menu 202, an impedance test may be initiated. Opposite the device menu 202 there is a collapsible test menu 204. The test menu 204 highlights each test that is available under the operable setup profile and may be used to navigate between functions. A collapsible stimulation bar 206 indicates the current stimulation status and provides start and stop stimulation buttons (not shown) to activate and control stimulation. The collapsible event bar 208 stores all the stimulation test results obtained throughout a procedure so that the user may review the entire case history from the monitoring screen. Clicking on a particular event will open a note box and annotations may be entered and saved with the response for later inclusion in a procedure report chronicling all nerve monitoring functions conducted during the procedure as well as the results of nerve monitoring. In one embodiment the report may be printed immediately from one or more printers located in the operating room or copied to any of a variety of memory devices known in the prior art, such as, by way of example only, a floppy disk, and/or USB memory stick. The system 10 may generate either a full report or a summary report depending on the particular needs of the user. In one embodiment, the identifiers used to identify the surgical accessories to the patient module may also be encoded to identify their lot number or other identifying information. As soon as the accessory is identified, the lot number may be automatically added to the report. Alternatively, hand held scanners can be provided and linked to the control unit 12 or patient module 14. The accessory packaging may be scanned and again the information may go directly to the procedure report. The event bar 208 also houses a chat box feature when the system 10 is connected to a remote monitoring system to allow a user in the operating room to contemporaneously communicate with a person performing the associated neuromonitoring in a remote location.

The system 10 may also conduct free-run EMG monitoring while the system is in any of the modes described herein. Free-run EMG monitoring continuously listens for spontaneous muscle activity that might be indicative of potential danger. The system 10 may automatically cycle into free-run monitoring after 5 seconds of inactivity. Initiating a stimulation signal in the selected mode will interrupt the free-run monitoring until the system 10 has again been inactive for five seconds, at which time the free-run begins again.

The system 10 may test the integrity of pedicle holes (during and/or after formation) and/or screws (during and/or after introduction) via the Basic Stimulation EMG and Dynamic Stimulation EMG tests. To perform the Basic Stimulation EMG a test probe 116 is placed in the screw hole prior to screw insertion or placed on the installed screw head and a stimulation signal is applied. The insulating character of bone will prevent the stimulation current, up to a certain amplitude, from communicating with the nerve, thus resulting in a relatively high $I_{thresh}$, as determined via the basic threshold hunting algorithm described below. However, in the event the pedicle wall has been breached by the screw or tap, the current density in the breach area will increase to the point that the stimulation current will pass through to the adjacent nerve roots and they will depolarize at a lower stimulation current, thus $I_{thresh}$ will be relatively low. The system described herein may exploit this knowledge to inform the practitioner of the current $I_{thresh}$ of the tested screw to determine if the pilot hole or screw has breached the pedicle wall.

In Dynamic Stim EMG mode, test probe 116 may be replaced with a clip 18 which may be utilized to couple a surgical tool, such as for example, a tap member 28 or a pedicle access needle 26, to the system 10. In this manner, a stimulation signal may be passed through the surgical tool and pedicle integrity testing can be performed while the tool is in use. Thus, testing may be performed during pilot hole formation by coupling the access needle 26 to the system 10, and during pilot hole preparation by coupling the tap 28 to the system 10. Likewise, by coupling a pedicle screw to the system 10 (such as via pedicle screw instrumentation), integrity testing may be performed during screw introduction.

In both Basic Stimulation EMG mode and Dynamic Stimulation EMG mode, the signal characteristics used for testing in the lumbar testing may not be effective when monitoring in the thoracic and/or cervical levels because of the proximity of the spinal cord to thoracic and cervical pedicles. Whereas a breach formed in a pedicle of the lumbar spine results in stimulation being applied to a nerve root, a breach in a thoracic or cervical pedicle may result in stimulation of the spinal cord instead, but the spinal cord may not respond to a stimulation signal the same way the nerve root would. To account for this, the surgical system 10 is equipped to deliver stimulation signals having different characteristics based on the region selected. By way of example only, when the lumbar region is selected, stimulation signals for the stimulated EMG modes comprise single pulse signals. On the other hand, when the thoracic and cervical regions are selected the stimulation signals may be configured as multipulse signals.

Figure 22:
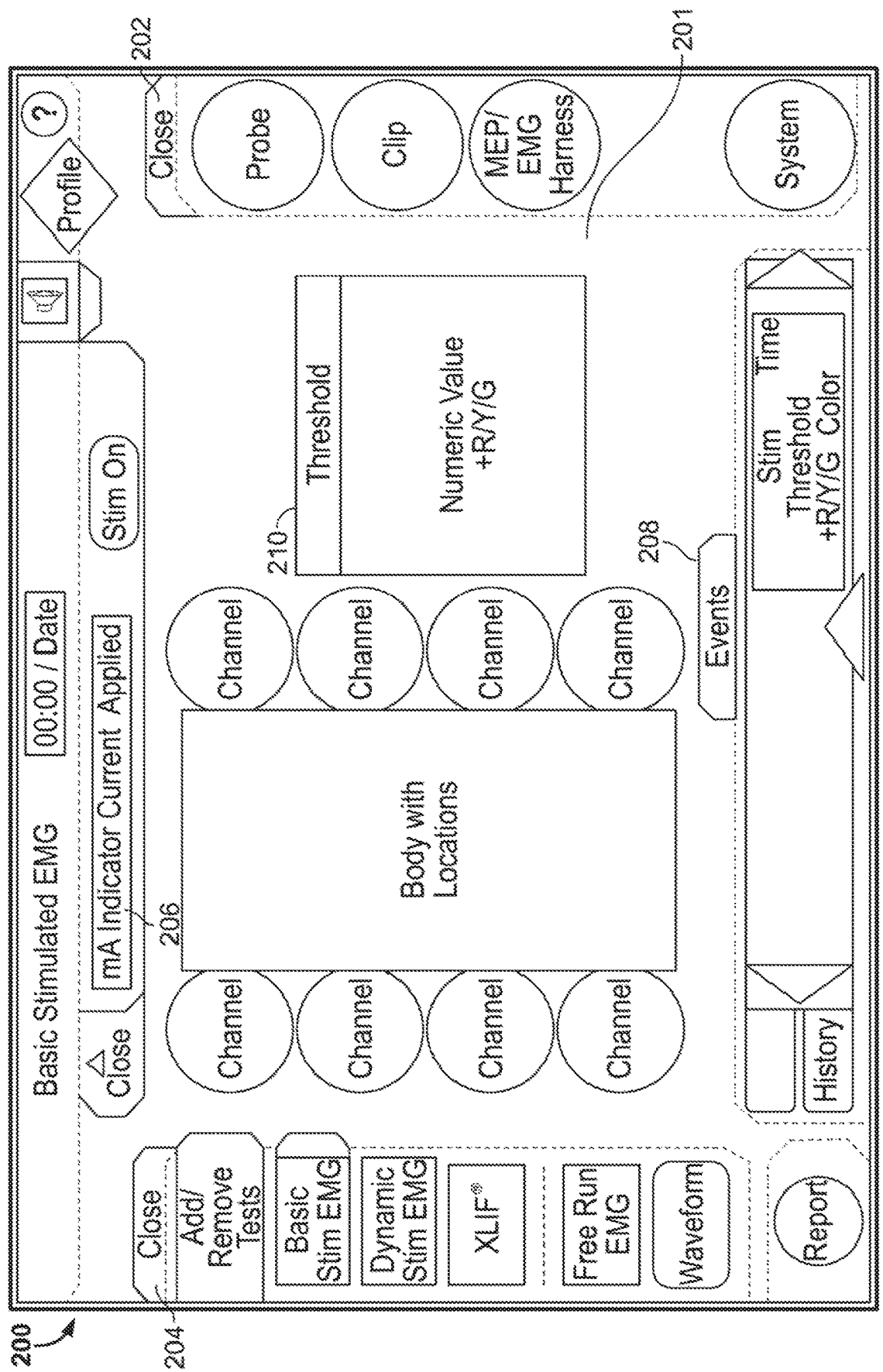
FIG. 22 is a screenshot of an example embodiment of a Basic Stimulation EMG monitoring screen forming part of the system of FIG. 1.
Figure 23:
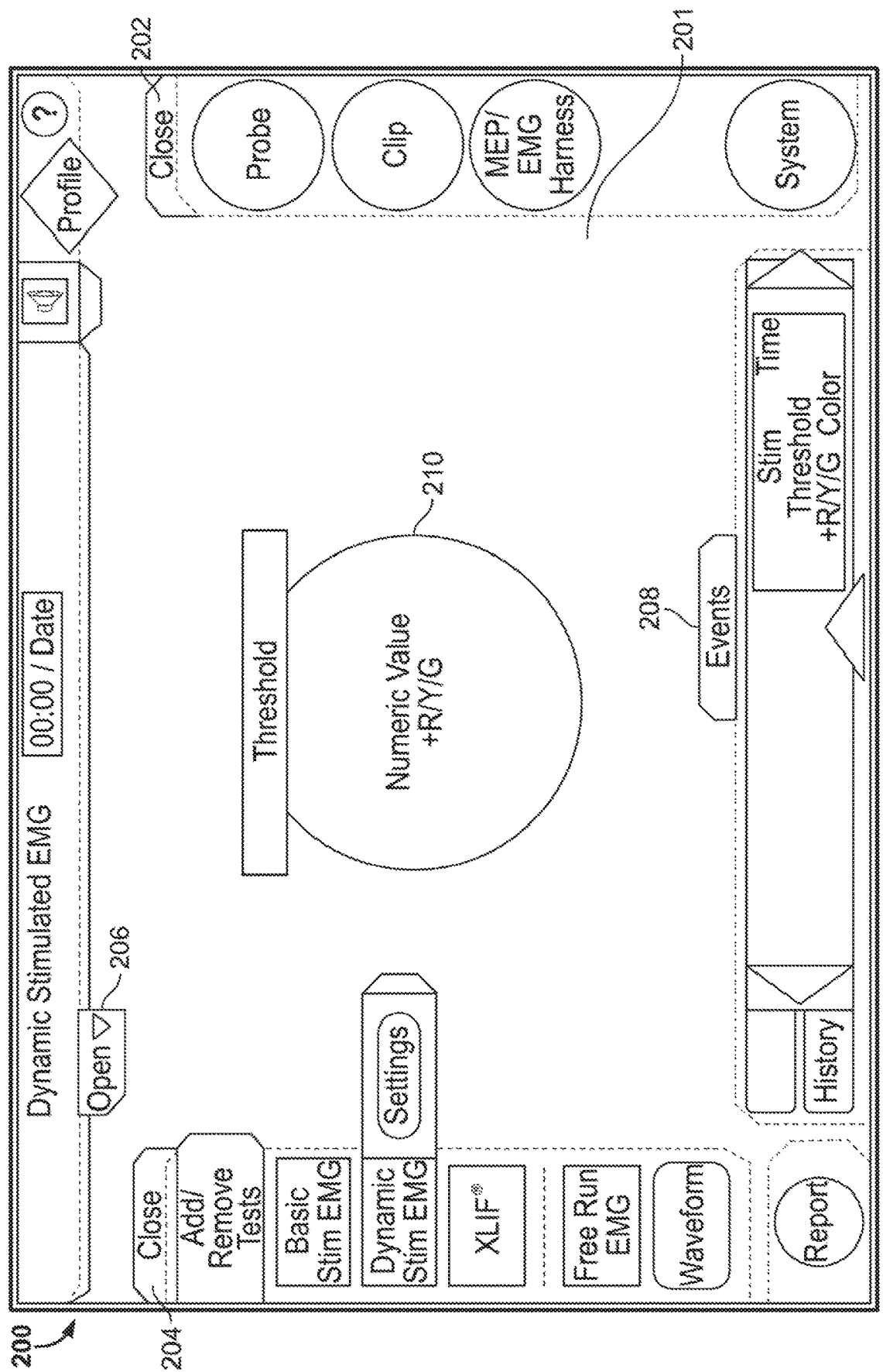
FIG. 23 is a screenshot of an example embodiment of a Dynamic Stimulation EMG monitoring screen forming part of the system of FIG. 1.

Stimulation results (including but not necessarily limited to at least one of the numerical $I_{thresh}$ value and color coded safety level indication) and other relevant data are conveyed to the user on at least main display 34, as illustrated in FIGS. 22 and 23. FIG. 22 illustrates the monitoring screen 200 with the Basic Stimulation EMG test selected. FIG. 23 illustrates the monitoring screen 200 with the Dynamic Stimulation EMG test selected. In one embodiment of the various screw test functions (e.g. Basic and Dynamic), green corresponds to a threshold range of greater than 10 milliamps (mA), a yellow corresponds to a stimulation threshold range of 7-10 mA, and a red corresponds to a stimulation threshold range of 6 mA or below. EMG channel tabs may be selected via the touch screen display 26 to show the $I_{thresh}$ of the corresponding nerves. Additionally, the EMG channel possessing the lowest $I_{thresh}$ may be automatically highlighted and/or colored to clearly indicate this fact to the user.

Figure 24:
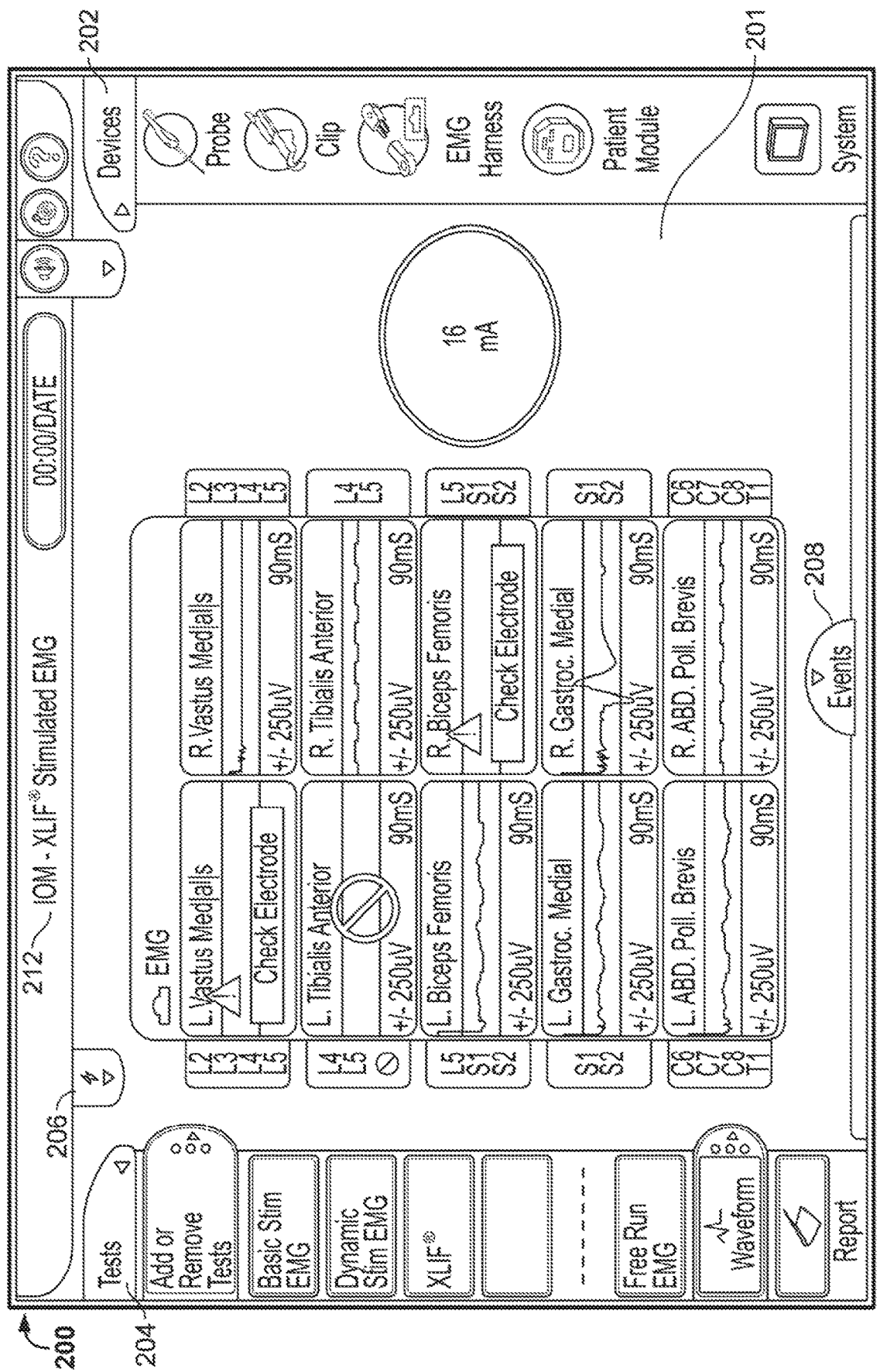
FIG. 24 is a screenshot of an example embodiment of a Nerve Surveillance EMG monitoring screen forming part of the system of FIG. 1.

The system 10 may perform nerve proximity testing, via the XLIF mode, to ensure safe and reproducible access to surgical target sites. Using the surgical access components 26-32, the system 10 detects the existence of neural structures before, during, and after the establishment of an operative corridor through (or near) any of a variety of tissues having such neural structures which, if contacted or impinged, may otherwise result in neural impairment for the patient. The surgical access components 26-32 are designed to bluntly dissect the tissue between the patient's skin and the surgical target site. Dilators of increasing diameter, which are equipped with one or more stimulating electrodes, are advanced towards the target site until a sufficient operating corridor is established to advance retractor 32 to the target site. As the dilators are advanced to the target site electrical stimulation signals are emitted via the stimulation electrodes. The stimulation signal will stimulate nerves in close proximity to the stimulation electrode and the corresponding EMG response is monitored. As a nerve gets closer to the stimulation electrode, the stimulation current required to evoke a muscle response decreases because the resistance caused by human tissue will decrease, and it will take less current to cause nervous tissue to depolarize. $I_{thresh}$ is calculated, using the basic threshold hunting algorithm described below, providing a measure of the communication between the stimulation signal and the nerve and thus giving a relative indication of the proximity between access components and nerves. An example of the monitoring screen 200 with XLIF mode active is depicted in FIG. 24. In a preferred embodiment, a green or safe level corresponds to a stimulation threshold range of 10 milliamps (mA) or greater, a yellow level denotes a stimulation threshold range of 5-9 mA, and a red level denotes a stimulation threshold range of 4 mA or below.

Figure 25:
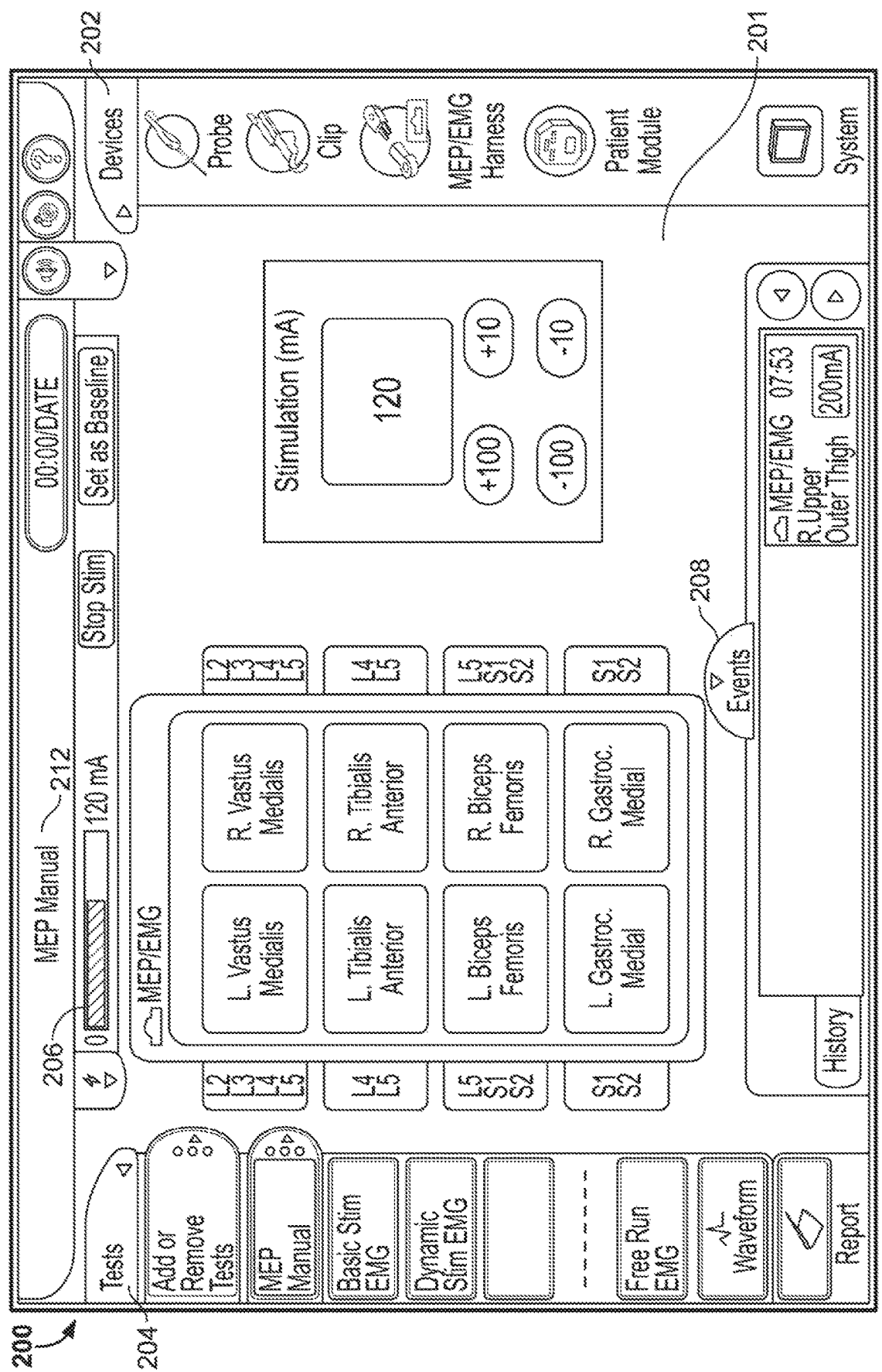
FIG. 25 is a screenshot of an example embodiment of a Manual MEP monitoring screen forming part of the system of FIG. 1.
Figure 26:
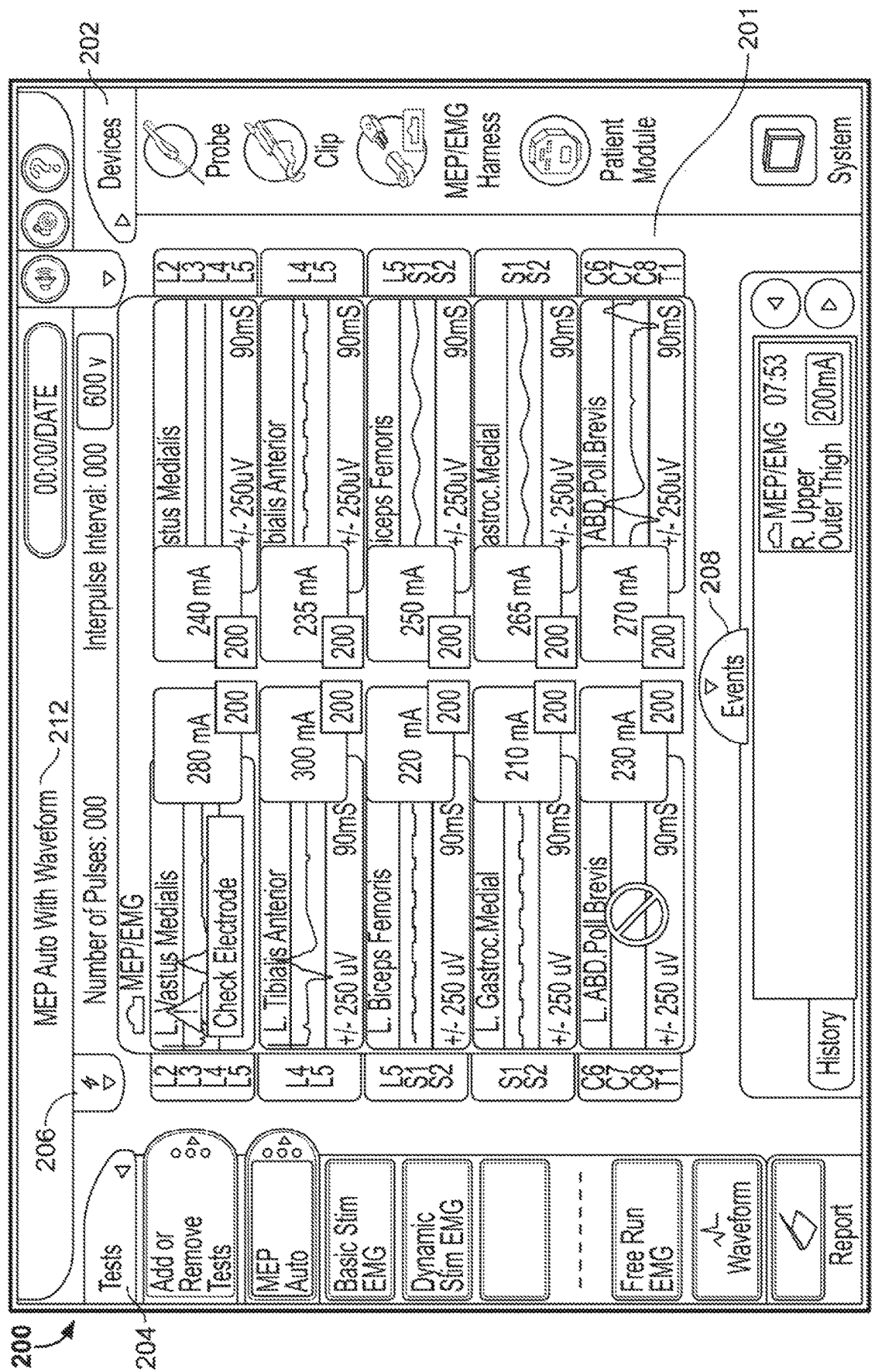
FIG. 26 is a screenshot of an example embodiment of an Automatic MEP monitoring screen forming part of the system of FIG. 1.

In MEP modes, stimulation signals are delivered to the motor cortex via patient module 14 and resulting responses are detected from various muscles in the upper and lower extremities. An increase in $I_{thresh}$ from an earlier test to a later test may indicate a degradation of spinal cord function. Likewise, the absence of a significant EMG response to a given $I_{stim}$ on a channel that had previously reported a significant response to the same or lesser $I_{stim}$ is also indicative of a degradation in spinal cord function. These indicators are detected by the system in the MEP modes and reported to the surgeon. In MEP Manual mode, the user selects the stimulation current level and the system reports whether or not the stimulation signal evokes a significant response on each channel. Stimulation results may be shown on the display 34 in the form of "YES" and "NO" responses, or other equivalent indicia, as depicted in FIG. 25. In MEP Automatic mode the system determines the $I_{thresh}$ baseline for each channel corresponding to the various monitored muscles, preferably early in the procedure, using the multichannel algorithm described. Throughout the procedure subsequent tests may be conducted to again determine $I_{thresh}$ for each channel. The difference between the resulting $I_{thresh}$ values and the corresponding baseline are computed by the system 10 and compared against predetermined "safe" and "unsafe" difference values. The $I_{thresh}$, baseline and difference values are displayed to the user, along with any other indicia of the safety level determined (such as a red, yellow, green color code), on the display 34, as illustrated in FIG. 26. Using either mode the surgeon may thus be alerted to potential complications with the spinal cord and any corrective actions deemed necessary may be undertaken at the discretion of the surgeon.

Figure 27:
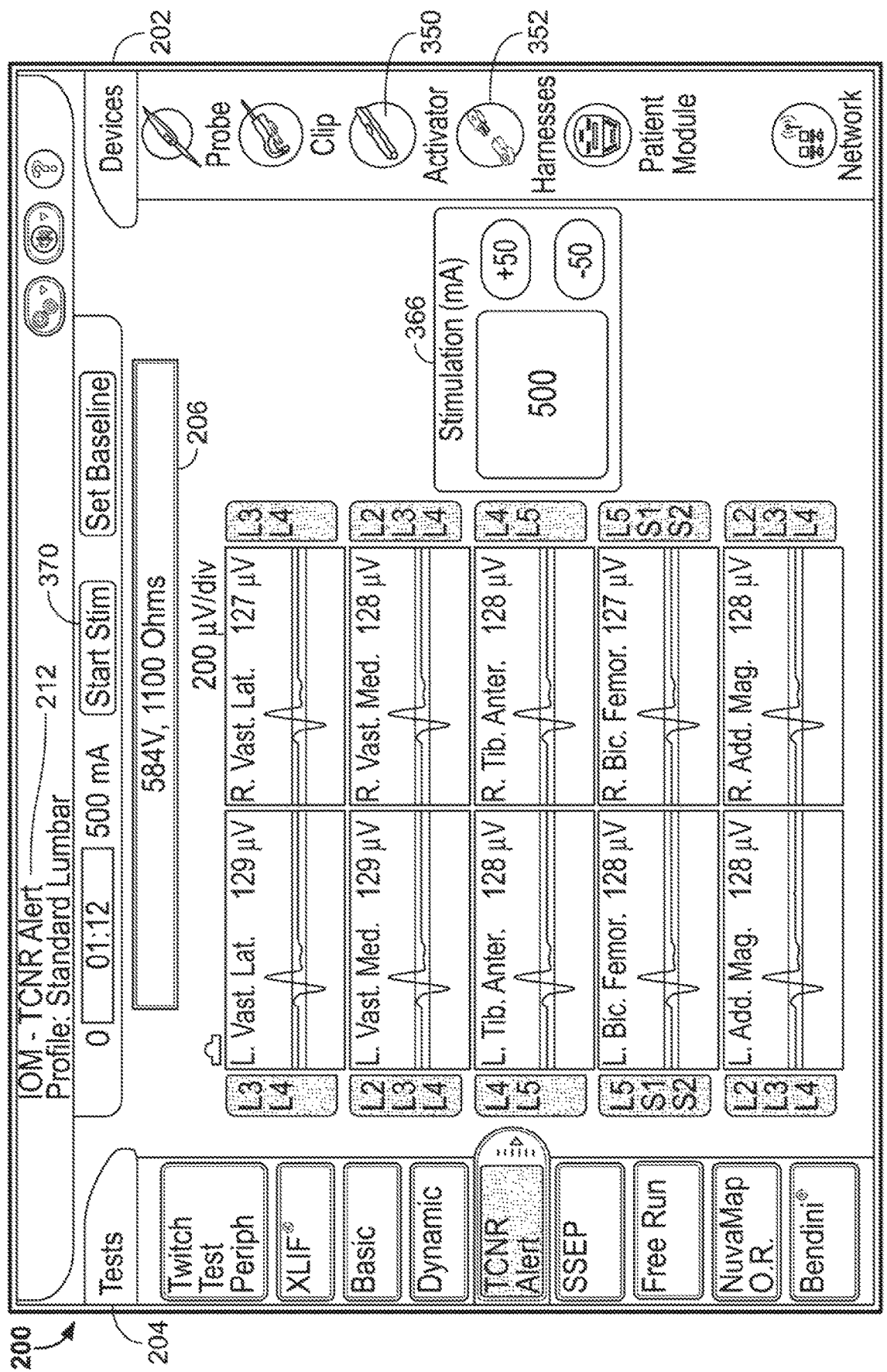
FIG. 27 is a screenshot of an example embodiment of a TCNR Alert monitoring screen forming part of the system of FIG. 1.
Figure 28:
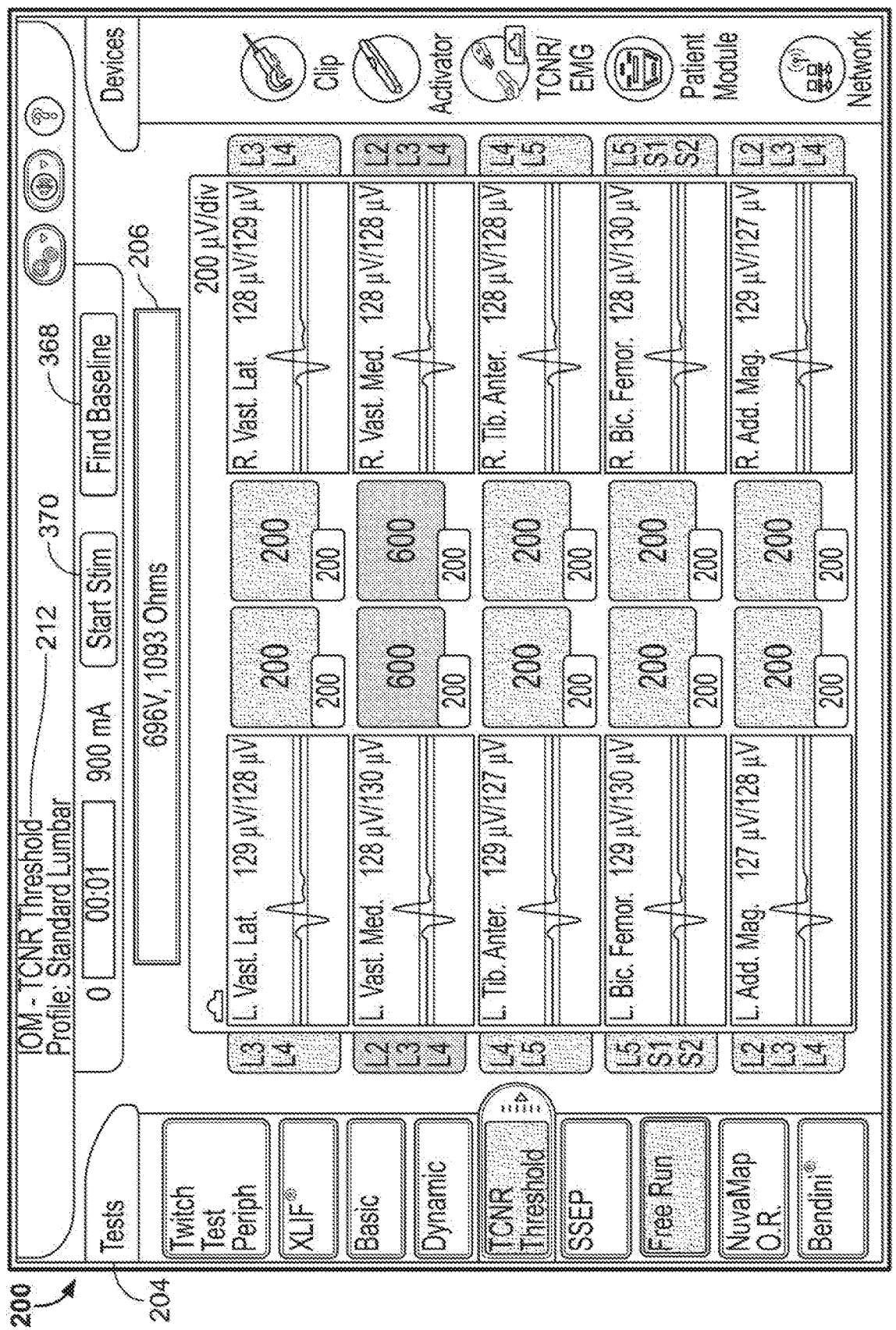
FIG. 28 is a screenshot of an example embodiment of a TCNR Threshold monitoring screen forming part of the system of FIG. 1.
Figure 29:
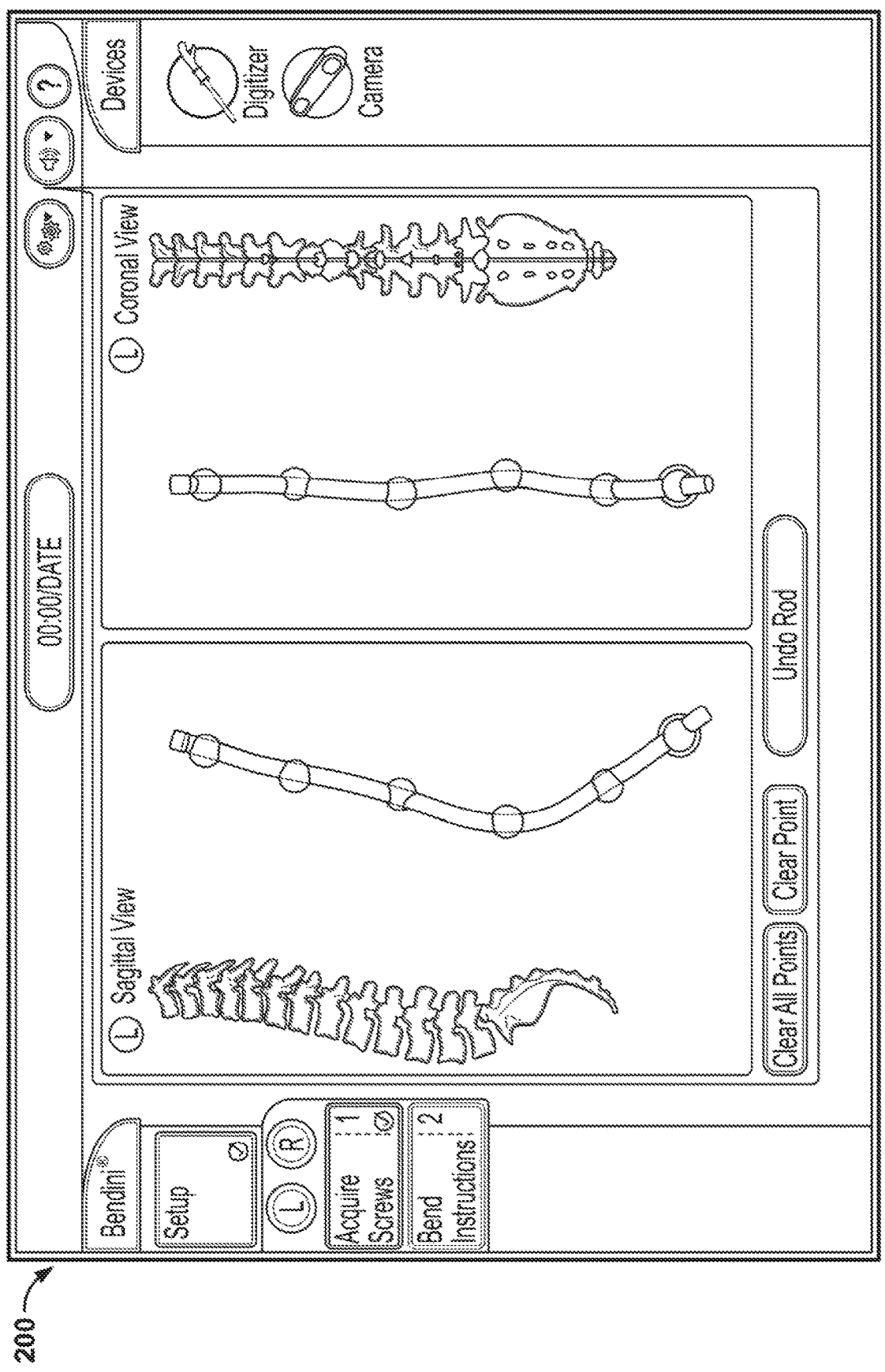
FIG. 29 is a screenshot of an example embodiment of a first surgical correction planning and assessment screen forming part of the system of FIG. 1.

In Transcutaneous Nerve Root Stimulation modes (TCNR), the system 10 is capable of ascertaining the health and/or status of at-risk nerves along the motor neural pathway superior and inferior to the surgical site before, during, and/or after the creation of the operative corridor to the surgical target site. To accomplish this, stimulation electrodes 22 may be placed on the skin over the desired spinal nerve roots (such as by way of example only, the L1 and L2 nerve roots and/or the location of the conus medullaris of the patient) and recording electrodes 24 are positioned on the recording sites (such as, by way of example only, the recording sites set forth above in Table 5). The control unit 12 and patient module 14 cooperate to transmit electrical stimulation signals to a stimulating cathode placed posteriorly on the patient's back. These stimulation signals cause nerves deep to the stimulating electrode to depolarize, evoking activity from muscles innervated by the nerves below. The system 10 detects and records the neuromuscular responses and optionally analyzes their relationship to the stimulation signal (discussed below). Resulting recording and/or assessment data is conveyed to the user, for example on screen 200. The TCNR testing provides the ability to verify that the patient is positioned in a neutral way and that no neural structures have been impinged upon after the operative corridor has been established. In TCNR Alert mode, the underlying neurophysiologic principle of operation is to assess the health and status of the lower motor neural pathway periodically during the surgical procedure via the presence/absence of evoked neuromuscular responses for each muscle monitored. FIG. 27 depicts an example screen display for the Alert mode of the TCNR monitoring function. In TCNR Threshold mode, the underlying neurophysiologic principle is that, in order to monitor the health of the lumbar motor neural pathway, the user must be able to determine if the evoked responses are changing with respect to the stimulation signal. To monitor for this change, baseline TCNR responses are established for all muscles of interest (preferably prior to surgical manipulation) and then compared to subsequent TCNR responses periodically throughout the procedure. FIG. 28 depicts an example screen display for the Threshold mode of the TCNR monitoring function.

Figure 30:
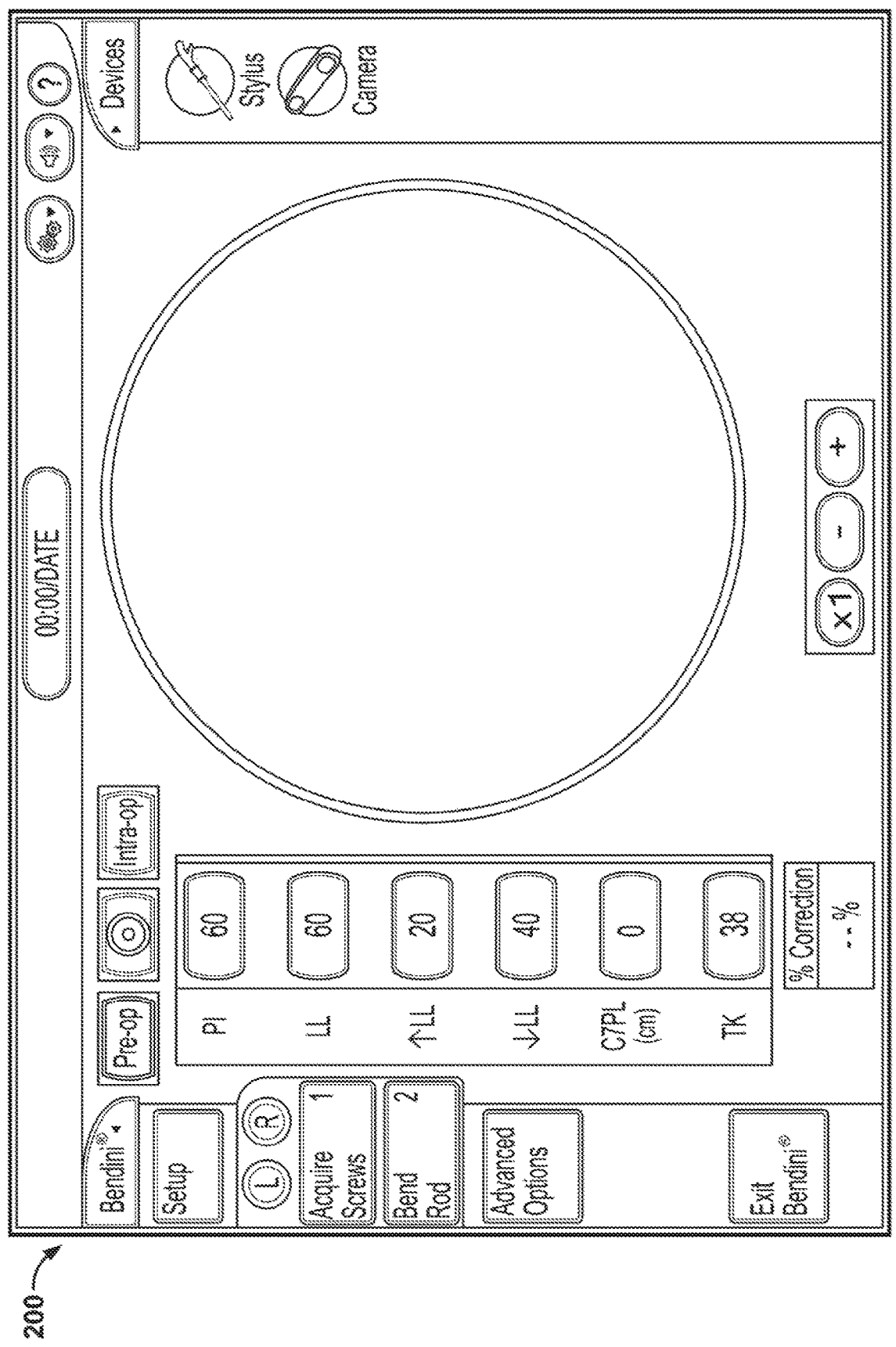
FIG. 30 is a screenshot of an example embodiment of second surgical correction planning and assessment screen forming part of the system of FIG. 1.

In the surgical correction planning and assessment mode, the system 10 aids the user in planning and assessing the degree to which he/she has achieved the surgical goals during a spinal procedure. As illustrated, by way of example only, in FIG. 29, there may be included a feature in which the system 10 is capable of digitizing implanted screw positions, outputting bend instructions for a rod, and previewing the shape of the rod on screen 200. In some implementations, the rod bending instructions are for a rod shaped to custom-fit within the implanted screw locations. In other implementations, the system 10 is further capable of accepting correction inputs via one or more advanced option features for viewing bend instructions for a rod shaped to fit at locations apart from those implanted screw locations. Installing a rod shaped in this manner could correct a curvature deformity in the patient's spine according to a user's prescribed surgical plan. In some spinal procedures, restoring a patient's spine to a balanced position may be a desired surgical outcome. As shown in FIG. 30, there may also be included a feature in which the system 10 is configured to receive and assess 1) preoperative spinal parameter inputs; 2) target spinal parameter inputs; 3) intraoperative spinal parameter inputs; and/or postoperative spine parameter inputs via screen 200. Spinal parameters may comprise the patient's Pelvic Incidence (PI), Pelvic Tilt (PT), Sacral Slope (SS), Lumbar Lordosis (LL), Superior Lumbar Lordosis (↑LL), Inferior Lumbar Lordosis (↓LL), C7 Plumb Line Offset (C7PL), Thoracic Kyphosis (TK), T1 Tilt, and Sagittal, Vertical Axis (SVA) measurements. One or more of these inputs may be tracked and/or compared against other inputs to assess how the surgical correction is progressing toward a surgical plan and utilized to develop/refine an operative plan to achieve the desired surgical correction.

In the SSEP modes, the system 10 stimulates peripheral sensory nerves that exit the spinal cord below the level of surgery and then measures the electrical action potential from electrodes located on the nervous system superior to the surgical target site. Recording sites below the applicable target site are also preferably monitored as a positive control measure to ensure variances from normal or expected results are not due to problems with the stimulation signal delivered (e.g. misplaced stimulation electrode, inadequate stimulation signal parameters, etc.). To accomplish this, stimulation electrodes 22 may be placed on the skin over the desired peripheral nerve (such as by way of example only, the left and right Posterior Tibial nerve and/or the left and right Ulnar nerve) and recording electrodes 24 are positioned on the recording sites (such as, by way of example only, at least two of the C2 vertebra, Cp3 scalp, Cp4 scalp, Erb's point, Popliteal Fossa) and stimulation signals are delivered from the patient module 14.

Damage in the spinal cord may disrupt the transmission of the signal up along the spinothalamic pathway through the spinal cord resulting in a weakened, delayed, or absent signal at the recording sites superior to the surgery location (e.g. cortical and subcortical sites). To check for these occurrences, the system 10 monitors the amplitude and latency of the evoked signal response. According to one embodiment, the system 10 may perform SSEP in either of two modes: Automatic mode and Manual mode. In SSEP Auto mode, the system 10 compares the difference between the amplitude and latency of the signal response vs. the amplitude and latency of a baseline signal response. The difference is compared against predetermined "safe" and "unsafe" levels and the results are displayed on display 34. According to one embodiment, the system may determine safe and unsafe levels based on each of the amplitude and latency values for each of the cortical and subcortical sites individually, for each stimulation channel. That is, if either of the subcortical and cortical amplitudes decrease by a predetermined level, or either of the subcortical and cortical latency values increase by a predetermined level, the system may issue a warning. By way of example, the alert may comprise a Red, Yellow, Green type warning associated with the applicable channel wherein Red indicates that at least one of the determined values falls within the unsafe level, the color green may indicate that all of the values fall within the safe level, and the color yellow may indicate that at least one of the values falls between the safe and unsafe levels. To generate more information, the system 10 may analyze the results in combination. With this information, in addition to the Red, Yellow, and Green alerts, the system 10 may indicate possible causes for the results achieved. In SSEP Manual mode, signal response waveforms and amplitude and latency values associated with those waveforms are displayed for the user. The user then makes the comparison between a baseline the signal response.

Figure 31:
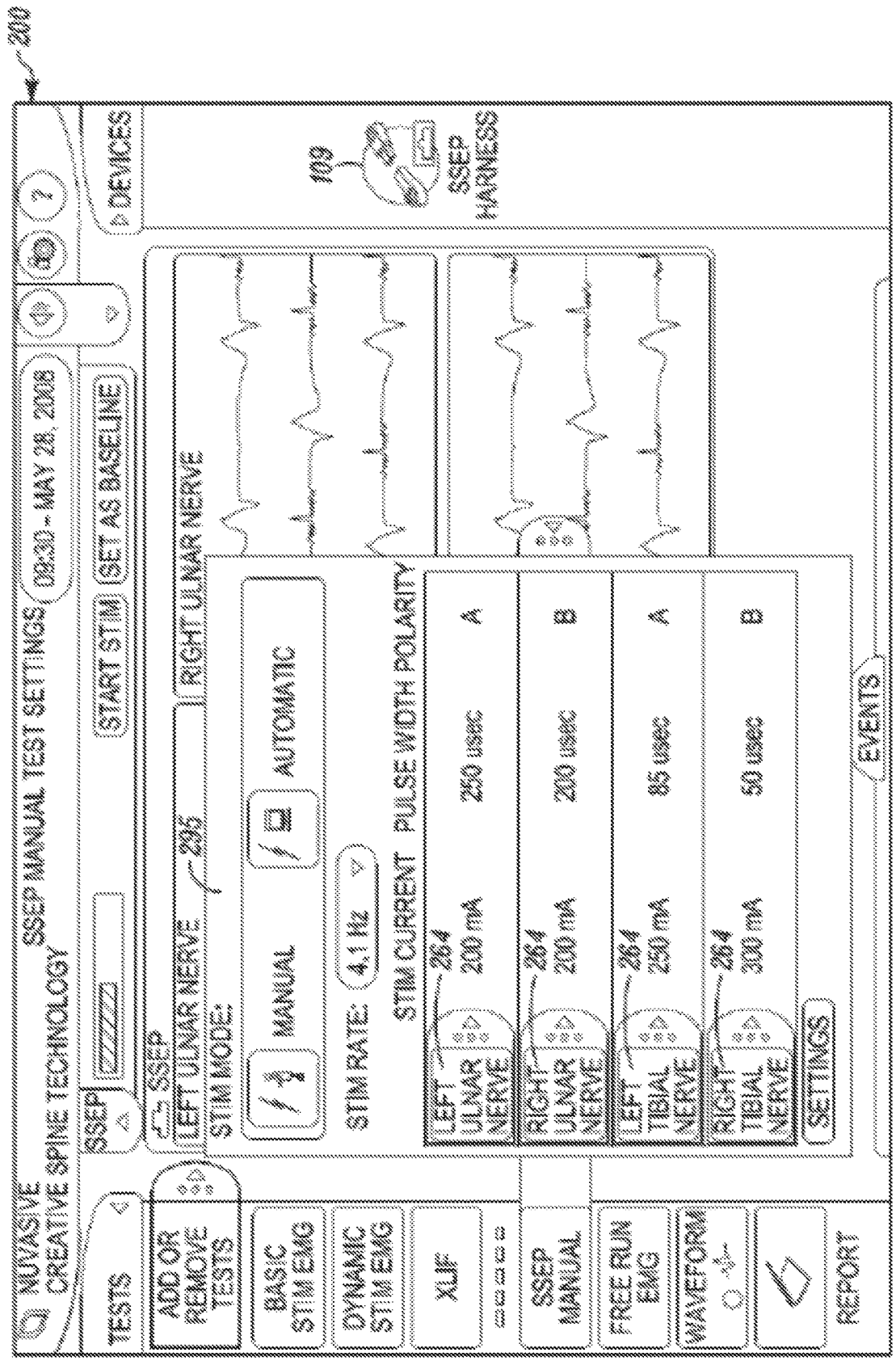
FIG. 31 is a screenshot of an example embodiment of an SSEP profile selection screen forming part of the system of FIG. 1.

FIGS. 31-36 are exemplary screen displays of the "SSEP Manual" mode according to one embodiment of the neuromonitoring system 10. FIG. 31 illustrates an setup screen from which various features and parameters of the SSEP Manual mode may be controlled and/or adjusted by the user as desired. Using this screen, the user has the opportunity to toggle between Manual mode and Automatic mode, select a stimulation rate, and change one or more stimulation settings (e.g. stimulation current, pulse width, and polarity) for each stimulation target site (e.g. left ulnar nerve, right ulnar nerve, left tibial nerve, and right tibial nerve). By way of example only, the user may change one or more stimulation settings of each peripheral nerve by first selecting one of the stimulation site tabs 264.

Figure 32:
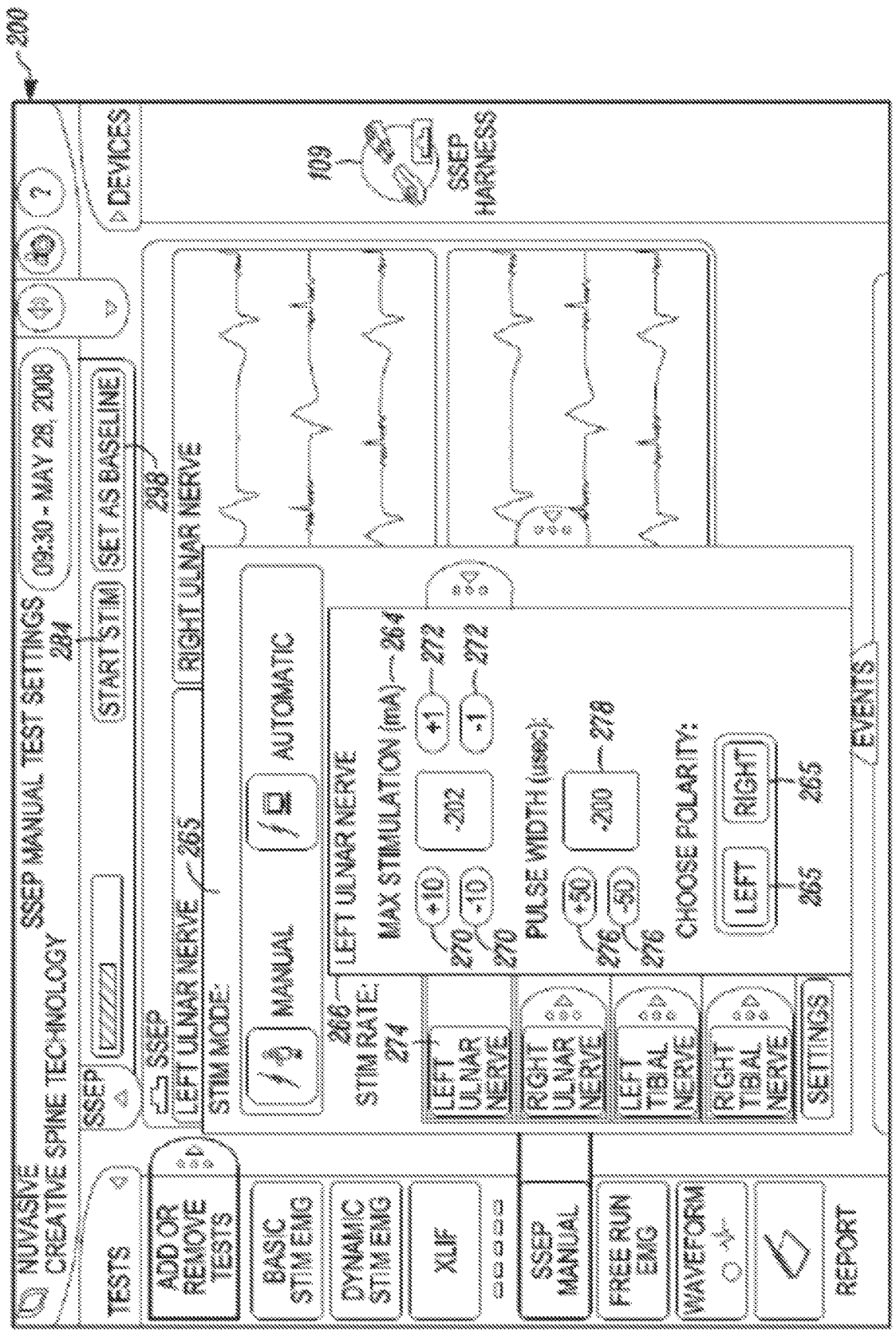
FIG. 32 is a screenshot of an example embodiment of an SSEP Manual Stimulus Mode setting with a Left Ulnar Nerve (LUN) breakout screen forming part of the system of FIG. 1.

Selecting one of the stimulation site tabs 264 will open a control window 265, seen in FIG. 32, from which various parameters of the SSEP manual test may be adjusted according to user preference. By way of example only, FIG. 32 is an illustration of an onscreen display for the SSEP manual test settings of the left ulnar nerve stimulation site. The highlighted "Left Ulnar Nerve" stimulation site tab 264 and the pop-up window title 266 indicate that adjusting any of the settings will alter the stimulation signal delivered to the left ulnar nerve. Multiple adjustment buttons are used to set the parameters of the stimulation signal. According to one example, the stimulation rate may be selected from a range between 2.2 and 6.2 Hz, with a default value of 4.7 Hz. The amplitude setting may be increased or decreased in increments of 10 mA using the amplitude selection buttons 270 labeled (by way of example only) "+10" and "−10". More precise amplitude selections may be made by increasing or decreasing the amplitude in increments of 1 mA using the amplitude selection buttons 272 labeled (by way of example only) "+1" and "−1". According to one example, the amplitude may be selected from a range of 1 to 100 mA with a default value of 10 mA. The selected amplitude setting is displayed in box 274. The pulse width setting may be increased or decreased in increments of 50 μsec using the width selection buttons 276 labeled "+50" and "−50". According to one example, the pulse width may be selected from a range of 50 to 300 μsec, with a default value of 200 μsec. The precise pulse width setting 278 is indicated in box 278. Polarity controls 280 may be used to set the desired polarity of the stimulation signal. SSEP stimulation may be initiated at the selected stimulation settings by pressing the SSEP stimulation start button 284 labeled (by way of example only) "Start Stim." Although stimulation settings adjustments are discussed with respect to the left ulnar nerve, it will be appreciated that stimulation adjustments may be applied to the other stimulation sites, including but not limited to the right ulnar nerve, and left and right tibial nerve. Alternatively, as described below, the system 10 may utilize an automated selection process to quickly determine the optimal stimulation parameters for each stimulation channel.

In order to monitor the health of the spinal cord with SSEP, the user must be able to determine if the responses to the stimulation signal are changing. To monitor for this change a baseline is determined, preferably during set-up. This can be accomplished simply by selecting the "set as baseline" button 298 next to the "start stim" button 284 on the setting screen illustrated in FIG. 32. Having determined a baseline recording for each stimulation site, subsequent monitoring may be performed as desired throughout the procedure and recovery period to obtain updated amplitude and latency measurements.

Figure 33:
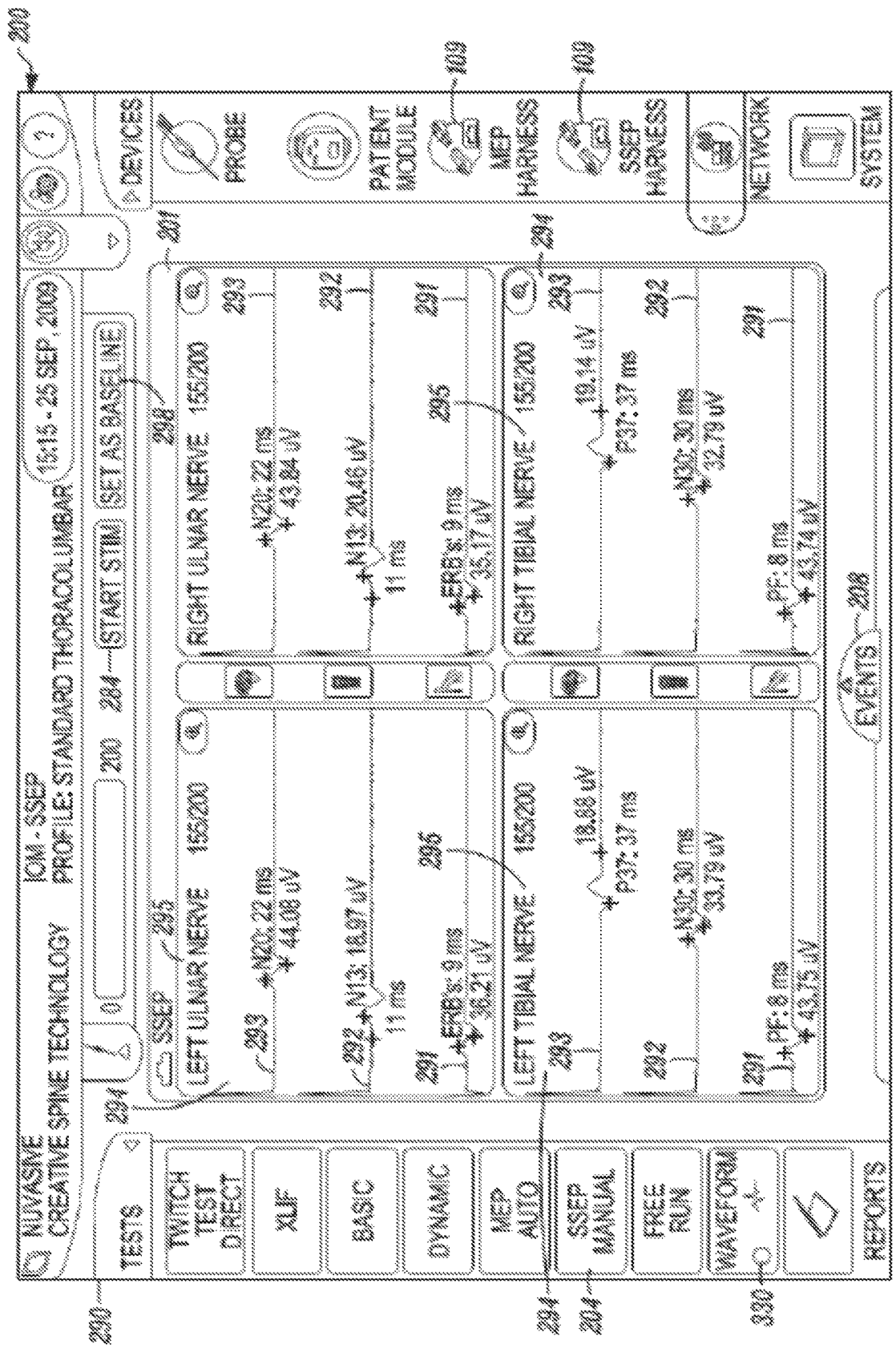
FIG. 33 is a screenshot of one embodiment of an SSEP Manual Run screen forming part of system of FIG. 1.

FIG. 33 depicts an exemplary screen display for Manual mode of the SSEP monitoring function. A mode indicator tab 290 on the test menu 204 indicates that "SSEP Manual" is the selected mode. The center result area 201 is divided into four sub areas or channel windows 294, each one dedicated to displaying the signal response waveforms for one of the stimulation nerve sites. The channel windows 294 depict information including the nerve stimulation site 295, and waveform waterfalls for each of the recording locations 291-293. For each stimulated nerve site, the system 10 displays three signal response waveforms, representing the measurements made at three different recording sites. By way of example only, the three recording sites are a peripheral 291 (from a peripheral nerve proximal to the stimulation nerve), subcortical 292 (spine), and cortical 293 (scalp), as indicated for example in Table 6 above. Each section may be associated with a pictorial icon, illustrating the neural/skeletal structure. Although SSEP stimulation and recording is discussed with respect to the nerve stimulation site and the recording sites discussed above, it will be appreciated that SSEP stimulation may be applied to any number of peripheral sensory nerves and the recording sites may be located anywhere along the nervous system superior to the spinal level at risk during the procedure.

During SSEP modes (auto and manual), a single waveform response is generated for each stimulation signal run (for each stimulation channel). The waveforms are arranged with stimulation on the extreme left and time increasing to the right. By way of example, the waveforms are captured in a 100 msec window following stimulation. The stimulation signal run is comprised of a predefined number of stimulation pulses firing at the selected stimulation frequency. By way of example only, the stimulation signal may include up to 300 pulses at a frequency of 4.7 Hz. A 100 ms window of data is acquired on each of three SSEP recording channels: cortical, subcortical, and peripheral. With each successive stimulation on the same channel during a stimulation run, the three acquired waveforms are summed and averaged with the prior waveforms during the same stimulation run for the purpose of filtering out asynchronous events such that only the synchronous evoked response remains after a sufficient number of pulses. Thus, the final waveform displayed by the system 10 represents an averaging of the entire set (e.g. 300) of responses detected.

Figure 34:
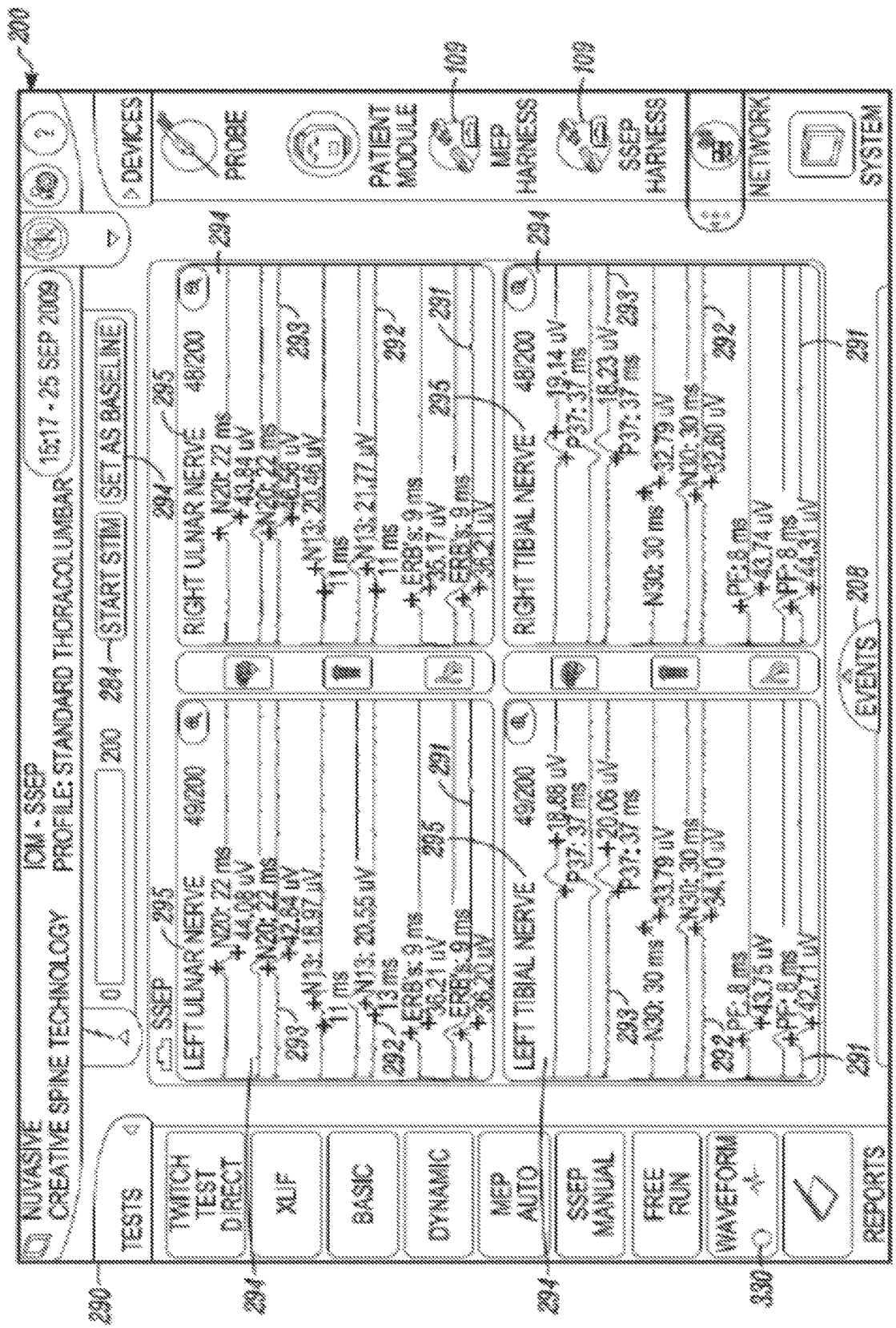
FIG. 34 is a screenshot of a second embodiment of an SSEP Manual Run screen forming part of the system of FIG. 1.
Figure 35:
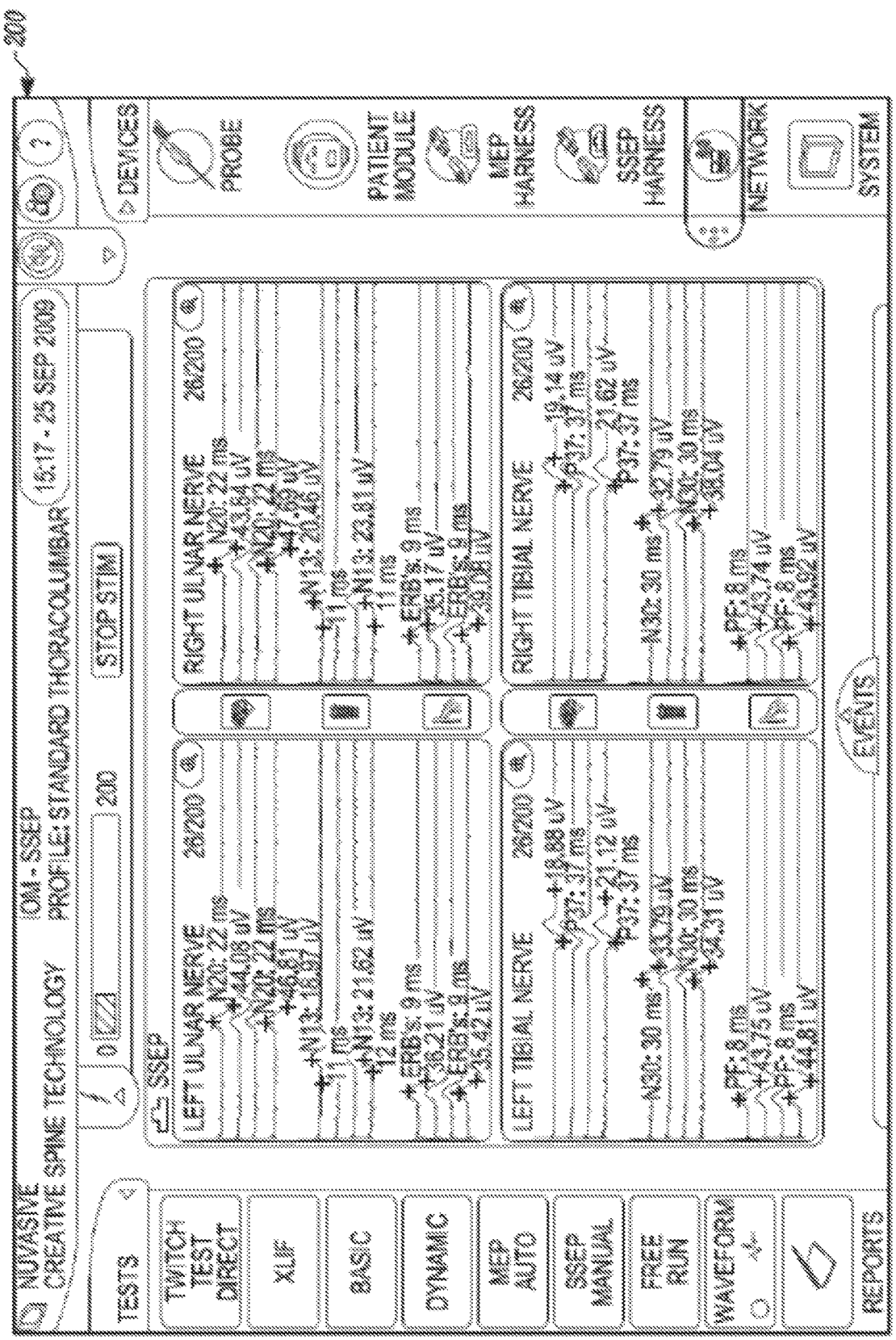
FIG. 35 is a screenshot of a third embodiment of an SSEP Manual Run screen forming part of the system of FIG. 1.

With each subsequent stimulation run, waveforms are drawn slightly lower each time, as depicted in FIGS. 33-35, until a total of four waveforms are showing. After more than four stimulation runs, the baseline waveform is retained, as well as the waveforms from the previous four stimulation runs. Older waveforms are removed from the waveform display. According to one embodiment, different colors may be used to represent the different waveforms. For example, the baseline waveforms may be colored purple, the last stimulation run may be colored white, the next-to-last stimulation run may be colored medium gray, and the earliest of the remaining stimulation runs may be colored dark gray.

According to one example, the baseline and the latest waveforms may have markers 314, 316 placed indicating latency and amplitude values associated with the waveform. The latency is defined as the time from stimulation to the first (earliest) marker. There is one "N" 314 and one "P" 316 marker for each waveform. The N marker is defined as the maximum average sample value within a window and the P value is defined as the minimum average sample value within the window. The markers may comprise cross consisting of a horizontal and a vertical line in the same color as the waveform. Associated with each marker is a text label 317 indicating the value at the marker. The earlier of the two markers is labeled with the latency (e.g. 22.3 ms). The latter of the two markers is labeled with the amplitude (e.g. 4.2 uV). The amplitude is defined as the difference in microvolts between average sample values at the markers. The latency is defined as the time from stimulation to the first (earliest) marker. Preferably, the markers are placed automatically by the system 10 (in both auto and manual modes). In manual mode, the user may select to place (and or move) markers manually.

Figure 36:
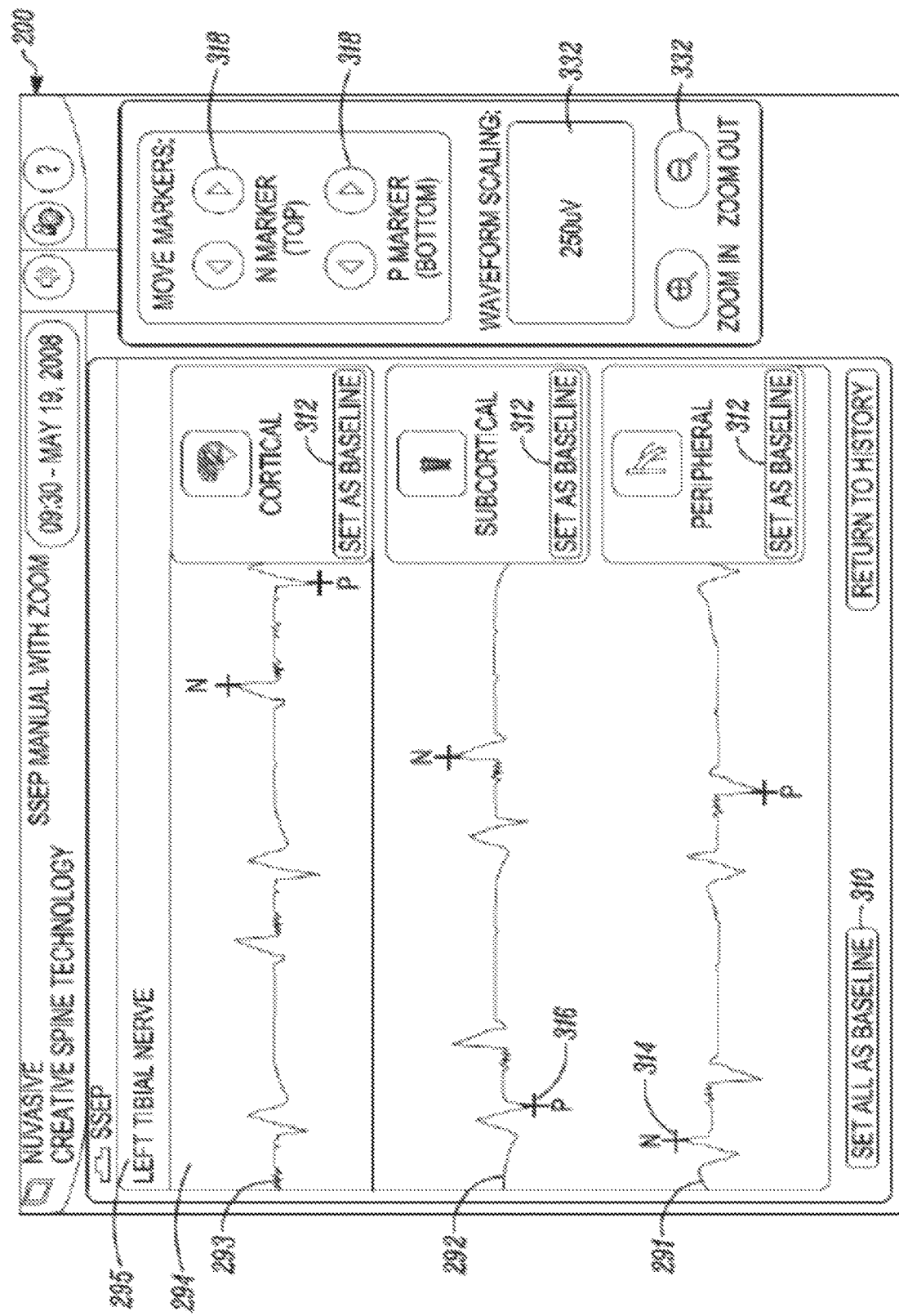
FIG. 36 is a screenshot of a fourth embodiment of an SSEP Manual Run screen forming part of the system of FIG. 1.

Further selecting one of the channel windows 294 will zoom in on the waveforms contained in that window 294. FIG. 36 is an example illustration of the zoom view achieved by selecting one of the channel windows 294. The zoom view includes waveforms 291-293, the baseline waveform, markers 314 and 316, and controls for moving markers 318 and waveform scaling 332. Only the latest waveform is shown. The "Set All as Baseline" button 310 will allow the user to set (or change) all three recorded waveforms as the baselines. Additionally, baselines may be set (or changed) individually by pressing the individual "Set as Baseline" buttons 312. Furthermore, the user may also move the N marker 314 and P markers 316 to establish new measurement points if desired. Direction control arrows 318 may be selected to move the N and P markers to the desired new locations. Alternatively, the user may touch and drag the marker 314, 316 to the new location. Utilizing the waveform controls 332 the user may zoom in and out on the recorded waveform.

Figure 37:
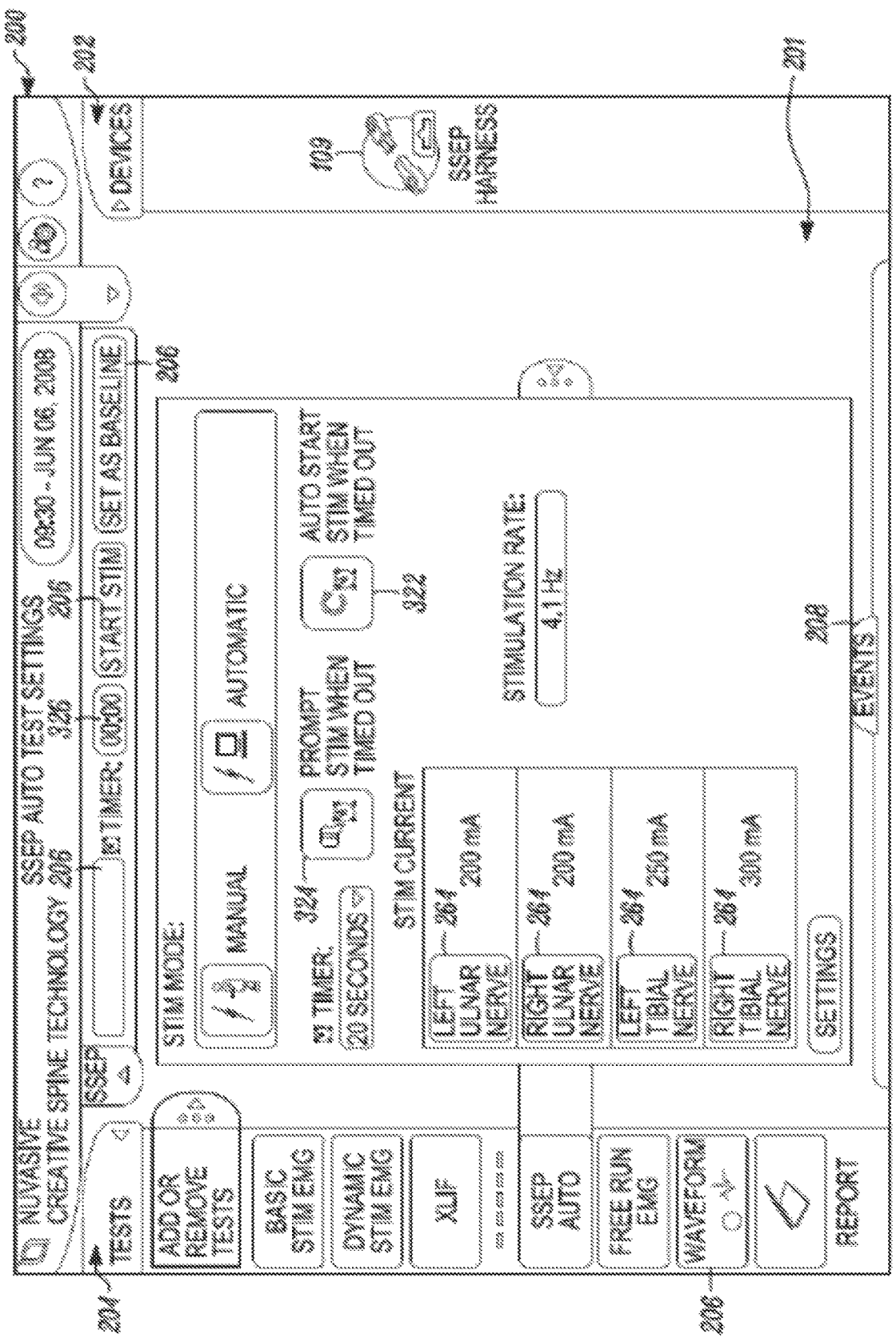
FIG. 37 is a screenshot of one embodiment of an SSEP Automatic Test screen forming part of the system of FIG. 1.

Referencing FIGS. 37-40, Automatic SSEP mode functions similar to Manual SSEP mode except that the system 10 determines the amplitude and latency values and alerts the user if the values deviate. FIG. 37 shows, by way of example only, an exemplary setup screen for the SSEP Automatic mode. In similar fashion to the setup screen previously described for the SSEP Manual mode, the user may toggle between Manual mode and Automatic mode, select a stimulation rate, and change one or more stimulation settings. By way of example only, the user may change one or more stimulation settings of each peripheral nerve by first selecting one of the stimulation site tabs 264, as described above with reference to Manual mode and FIG. 18. According to one example, the stimulation rate may be selected from a range between 2.2 and 6.2 Hz, with a default value of 4.7 Hz, the amplitude may be selected from a range of 1 to 100 mA, with a default value of 10 mA, the pulse width may be selected from a range of 50 to 300 μsec, with a default value of 200 μsec.

In Automatic mode, the system 10 also includes a timer function which can be controlled from the setup screen. Using the timer drop down menu 326, the user may set and/or change a time interval for the timer application. There are two separate options of the timer function: (1) an automatic stimulation on time out which can be selected by pressing the auto start button 322 labeled (by way of example only) "Auto Start Stim when timed out"; and (2) a prompted stimulation reminder on time out which can be selected by pressing the prompt stimulation button 324 labeled (by way of example only) "Prompt Stim when timed out". After each SSEP monitoring episode, the system 10 will initiate a timer corresponding to the selected time interval and, when the time has elapsed, the system will either automatically perform the SSEP stimulation or a stimulation reminder will be activated, depending on the selected option. The stimulation reminder may include, by way of example only, any one of, or combination of, an audible tone, voice recording, screen flash, pop up window, scrolling message, or any other such alert to remind the user to test SSEP again. It is also contemplated that the timer function described may be implemented in SSEP Manual mode.

Figure 38:
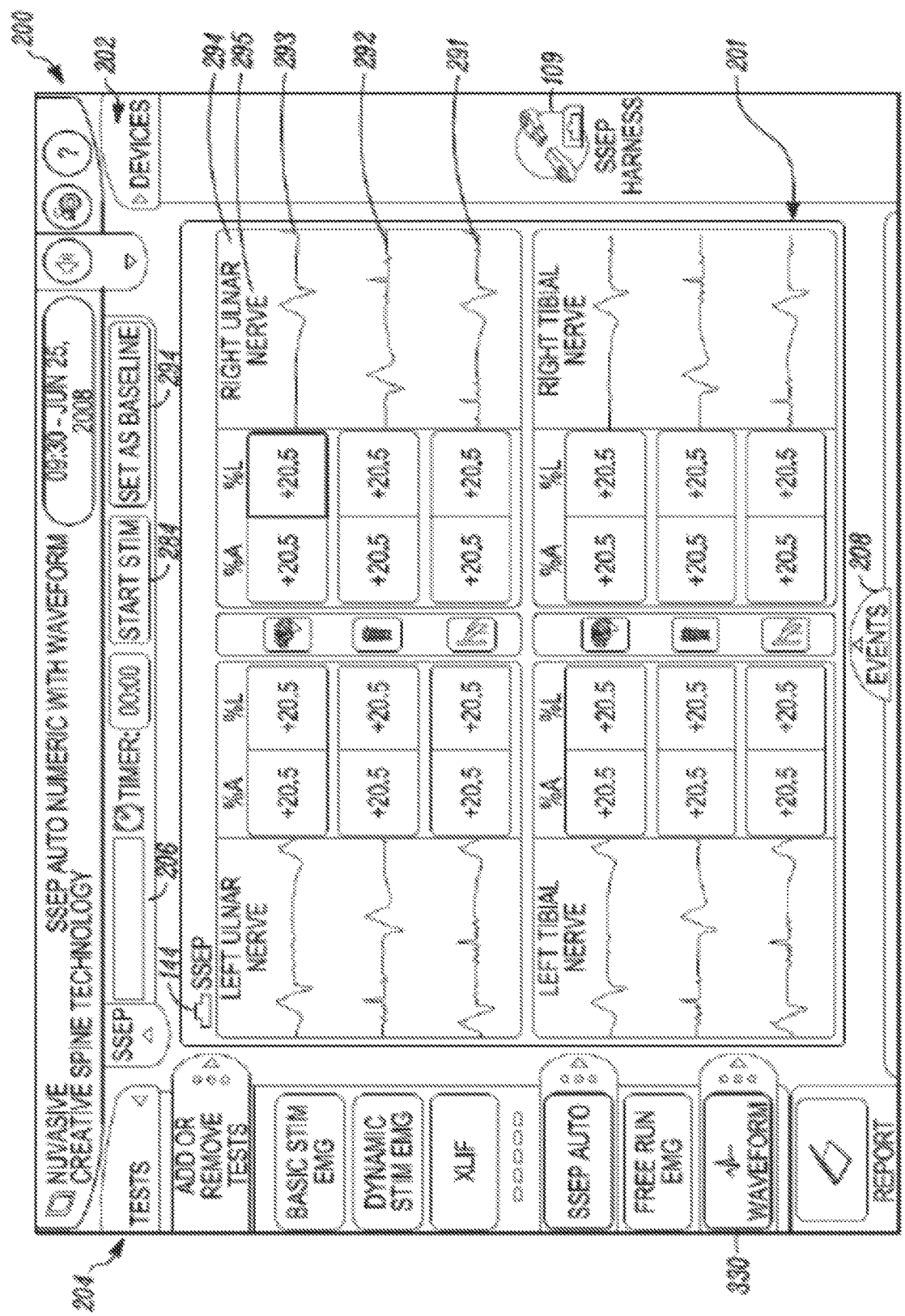
FIG. 38 is a screenshot of one embodiment of an SSEP Automatic Run screen forming part of the system of FIG. 1.
Figure 39:
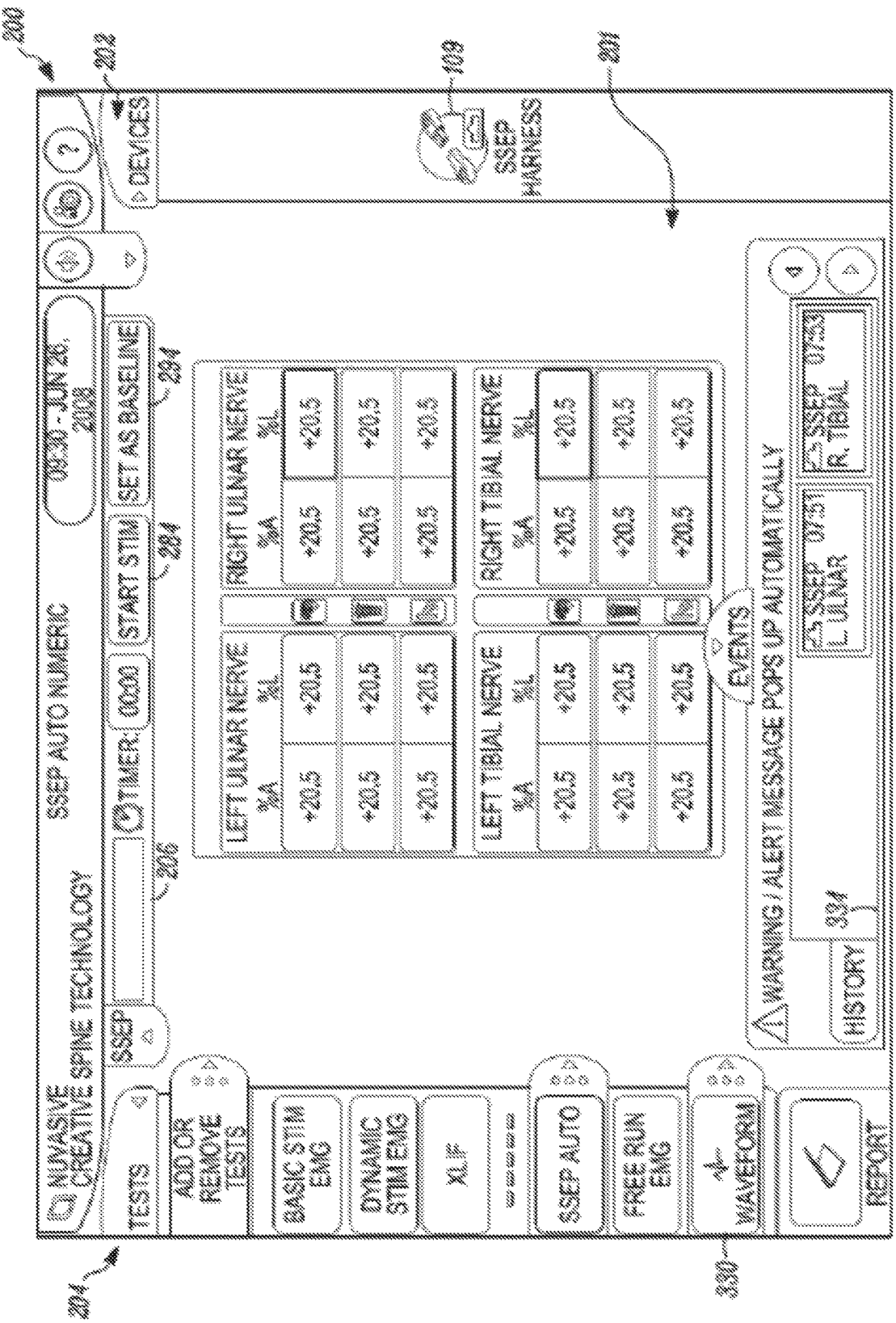
FIG. 39 is a screenshot of a second embodiment of an SSEP Automatic Run screen forming part of the system of FIG. 1.
Figure 40:
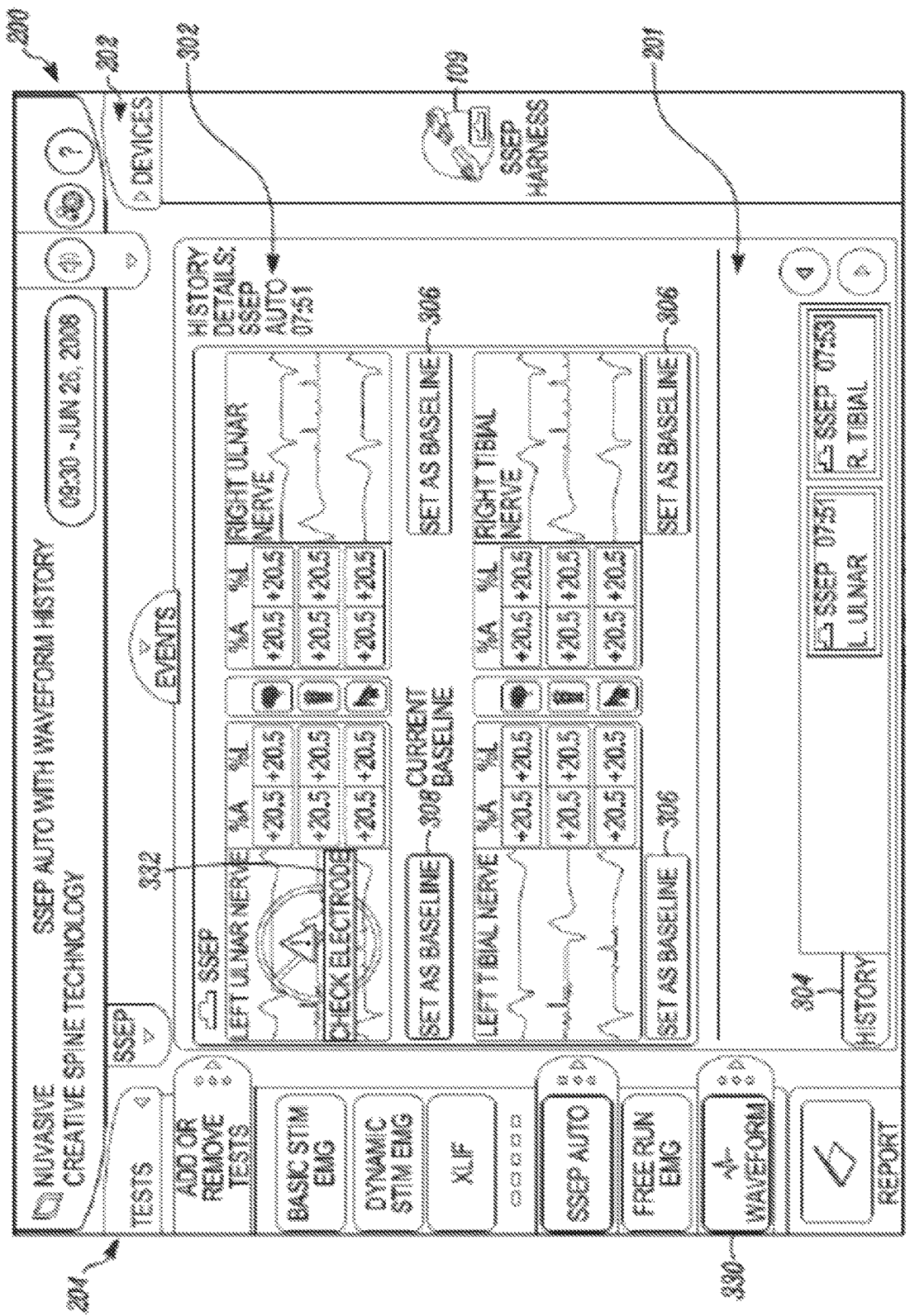
FIG. 40 is a screenshot of a third embodiment of an SSEP Automatic Run screen forming part of the system of FIG. 1.

FIGS. 38-40 depict exemplary onscreen displays for Automatic mode of the SSEP function. According to one embodiment, the user may select to view a screen with only alpha-numeric information (FIG. 39) and one with alpha-numeric information and recorded waveforms (FIG. 38). A mode indicator tab 290 indicates that "SSEP Auto" is the selected mode. A waveform selection tab 330 allows the user to select whether waveforms will be displayed with the alpha-numeric results. In similar fashion to the onscreen displays previously described for the SSEP Manual mode, the system 10 includes a channel window 294 for each nerve stimulation site. The channel window 294 may display information including the nerve stimulation site 295, waveform recordings, and associated recording locations 291-293

(peripheral, sub cortical, and cortical) and the percentage change between the baseline and amplitude measurements and the baseline and latency measurements. By way of example only, each channel window 294 may optionally also show the baseline waveform and latest waveform for each recording site. In the event the system 10 detects a significant decrease in amplitude or an increase in latency, the associated window may preferably be highlighted with a predetermined color (e.g. red) to indicate the potential danger to the surgeon. Preferably, the stimulation results are displayed to the surgeon along with a color code so that the user may easily comprehend the danger and corrective measures may be taken to avoid or mitigate such danger. This may for example, more readily permit SSEP monitoring results to be interpreted by the surgeon or assistant without requiring dedicated neuromonitoring personnel. By way of example only, red is used when the decrease in amplitude or increase in latency is within a predetermined unsafe level. Green indicates that the measured increase or decrease is within a predetermined safe level. Yellow is used for measurements that are between the predetermined unsafe and safe levels. By way of example only, the system 10 may also notify the user of potential danger through the use of a warning message 334. Although the warning message is in the form of a pop-up window, it will be appreciated that the warning may be communicated to the user by any one of, or combination of, an audible tone, voice recording, screen flash, scrolling message, or any other such alert to notify the user of potential danger.

With reference to FIG. 40, at any time during the procedure, a prior stimulation run may be selected for review. This may be accomplished by, for example, by opening the event bar 208 and selecting the desired event. Details from the event are shown with the historical details denoted on the right side of the menu screen 302 and waveforms shown in the center result screen. Again, the user may choose to reset baselines for one or more nerve stimulation sites by pressing the appropriate "Set As Baseline" button 306. In the example shown, the system 10 illustrates the waveform history at the 07:51 minute mark which is denoted on the right side of the menu screen 302. Prior waveform histories are saved by the surgical system 10 and stored in the waveform history toolbar 304. The describe only in relation to the SSEP Auto function it will be appreciated that the same features may be accessed from SSEP Manual mode, the user may choose to set a recorded stimulation measurement as the baseline for each nerve stimulation site by pressing the "Set As Baseline" button 306. By way of example only, the system 10 will inform the user if the applicable event is already the current baseline with a "Current Baseline" notification 308.

In addition to alerting the user to any changes in the amplitude and/or latency of the SSEP signal response, it is further contemplated that the neuromonitoring system 10 may assess the data from all the recording sites to interpret possible causes for changes in the SSEP response. Based on that information, the program may suggest potential reasons for the change. Furthermore, it may suggest potential actions to be taken to avoid danger. It is still further contemplated that the neurophysiology system 10 may be communicatively linked with other equipment in the operating room, such as for example, anesthesia monitoring equipment. Data from this other equipment may be considered by the program to generate more accuracy and or better suggestions.

By way of example only, Table 9 illustrates the SSEP illustrates various warnings that may be associated with particular SSEP results and result combinations from cortical, subcortical, and peripheral responses, and shown to the user. For example, if in response to stimulation of the left ulnar nerve, the peripheral response from Erb's Point showed no change in amplitude or latency, the subcortical response showed a decrease in amplitude, and the cortical response showed a decrease in amplitude, the event box 206 (shown in FIG. 39) would show either a yellow or a red indicator as well as the text "Possible mechanical insult. Possible spinal cord ischemia." By way of another example, if there is a decreased amplitude or absent response in all peripheral, subcortical, and cortical recording sites, the system may show a "Check Electrode" warning 332 (FIG. 40). With this date, and the particular circumstances leading to the result (e.g. what surgical maneuver resulted in the warning, etc.) the user may be better equipped to determine the most prudent course of action.

TABLE 9

| Neurophysiologic Event | Audio-visual Alert (Color) | SSEP Expert Text |
|---|---|---|
| Cortical amplitude decrease: 0-25% from baseline | Green | No Warning |
| Cortical amplitude decrease: 26-49% from baseline | Yellow | "Some anesthetic agents may reduce the cortical response amplitude." |
| Cortical amplitude decrease: 50%-99% from baseline | Red | "Some anesthetic agents may reduce the cortical response amplitude." |
| Cortical amplitude decrease: 100% from baseline | Red | "Possible cortical ischemia." |
| Cortical latency increase: 0-5% from baseline | Green | No Warning |
| Cortical latency increase: 6-9% from baseline | Yellow | "Some anesthetic agents may increase the cortical response latency. Possible cortical ischemia." |
| Cortical latency increase: 10% or greater from baseline | Red | "Some anesthetic agents may increase the cortical response latency. Possible cortical ischemia." |
| Cortical response absent: | Red | "Some anesthetic agents may cause the cortical response to be absent. Possible cortical ischemia." |
| Subcortical amplitude decrease: 0%-25% from baseline | Green | No Warning |
| Subcortical amplitude decrease: 25%-49% from baseline | Yellow | "Possible muscle activity artifact. Possible cervical recording electrode issue." |
| Subcortical amplitude decrease: 50-99% from baseline or absent | Red | "Possible muscle activity artifact. Possible cervical recording issue." |

TABLE 9-continued

| Neurophysiologic Event | Audio-visual Alert (Color) | SSEP Expert Text |
|---|---|---|
| 50% amplitude decrease, 10% latency increase in both cortical and subcortical responses, or absence in both cortical and subcortical responses: | Red | "Possible mechanical insult. Possible spinal cord ischemia." |
| Peripheral amplitude decrease: greater than 50% or absent | Red | "Possible peripheral recording electrode issue." |
| Peripheral (Erb's Point) amplitude decrease: 0-25% from baseline | Green | No Warning (left or right) |
| Peripheral (Erb's Point) amplitude decrease: 26-49% from baseline | Yellow | "Possible peripheral recording electrode issue (Left Erb's Point)." "Possible peripheral recording electrode issue (Right Erb's Point)." |
| Peripheral (Erb's Point) amplitude decrease: 50%-100% from baseline | Red | "Possible peripheral recording electrode issue (Left Erb's Point)." "Possible peripheral recording electrode issue (Right Erb's Point)." |
| Peripheral (Popliteal Fossa amplitude decrease: 0-25% from baseline | Green | No Warning (left or right) |
| Peripheral (Popliteal Fossa) amplitude decrease: 26-49% from baseline | Yellow | "Possible peripheral recording electrode issue (Left Popliteal Fossa)." "Possible peripheral recording electrode issue (Right Popliteal Fossa)." |
| Peripheral (Popliteal Fossa) amplitude decrease: 50%-100% from baseline | Red | "Possible peripheral recording electrode issue (Left Popliteal Fossa)." "Possible peripheral recording electrode issue (Right Popliteal Fossa)." |
| Peripheral (Erb's Point) latency increase: 0-5% from baseline | Green | No Warning (left or right) |
| Peripheral (Erb's Point) latency increase: 6-9% from baseline | Yellow | No Warning (left or right) |
| Peripheral (Erb's Point) latency increase: 10% or greater from baseline | Red | No Warning (left or right) |
| Peripheral (Popliteal Fossa) latency increase: 0-5% from baseline | Green | No Warning (left or right |
| Peripheral (Popliteal Fossa) latency increase: 6-9% from baseline | Yellow | No Warning (left or right) |
| Peripheral (Popliteal Fossa) latency increase: 10% or greater from baseline | Red | No Warning (left or right) |
| Peripheral (Popliteal Fossa) and subcortical amplitude decrease: 0-25% from baseline | Green | Possible muscle activity artifact. Possible cervical recording electrode issue. (left or right) |
| Peripheral (Popliteal Fossa) and subcortical amplitude decrease: 26%-100% from baseline | Yellow/Red | "Possible cervical muscle activity artifact. Possible cervical recording electrode issue. Possible muscle activity artifact (posterior tibial nerve)." (left or right) |
| Peripheral (Erb's Point) and subcortical amplitude decrease: 0-25% from baseline | Green | "Possible muscle activity artifact. Possible cervical recording electrode issue." (left or right) |
| Peripheral (Erb's Point) and subcortical amplitude decrease: 26-99% from baseline | Yellow/Red | "Possible cervical muscle activity artifact. Possible cervical recording electrode issue. Possible muscle activity artifact (median nerve)." (left or right) |
| Decreased amplitude or absent response in all, peripheral (left Erb's point), subcortical, and cortical: | Yellow/Red | "Possible stimulating electrode issue. (left wrist)." |
| Decreased amplitude or absent in all, peripheral (right Erb's point), subcortical, and cortical: | Yellow/Red | "Possible stimulating electrode issue (right wrist)." |
| Decreased amplitude or absent response in all peripheral (left Popliteal Fossa), subcortical, and cortical: | Yellow/Red | "Possible stimulating electrode issue (left ankle)." |
| Decreased amplitude or absent response in all peripheral (right Popliteal Fossa), subcortical, and cortical | Yellow/Red | Possible stimulating electrode issue (right ankle) |
| Increased latency or decreased amplitude in all, peripheral, subcortical, and cortical: | Yellow/Red | "Possible systemic change (hypotension, hypothermia, hyperthermia). Possible peripheral nerve ischemia." (left or right) (posterior tibial or ulnar nerve) |

Figure 41:
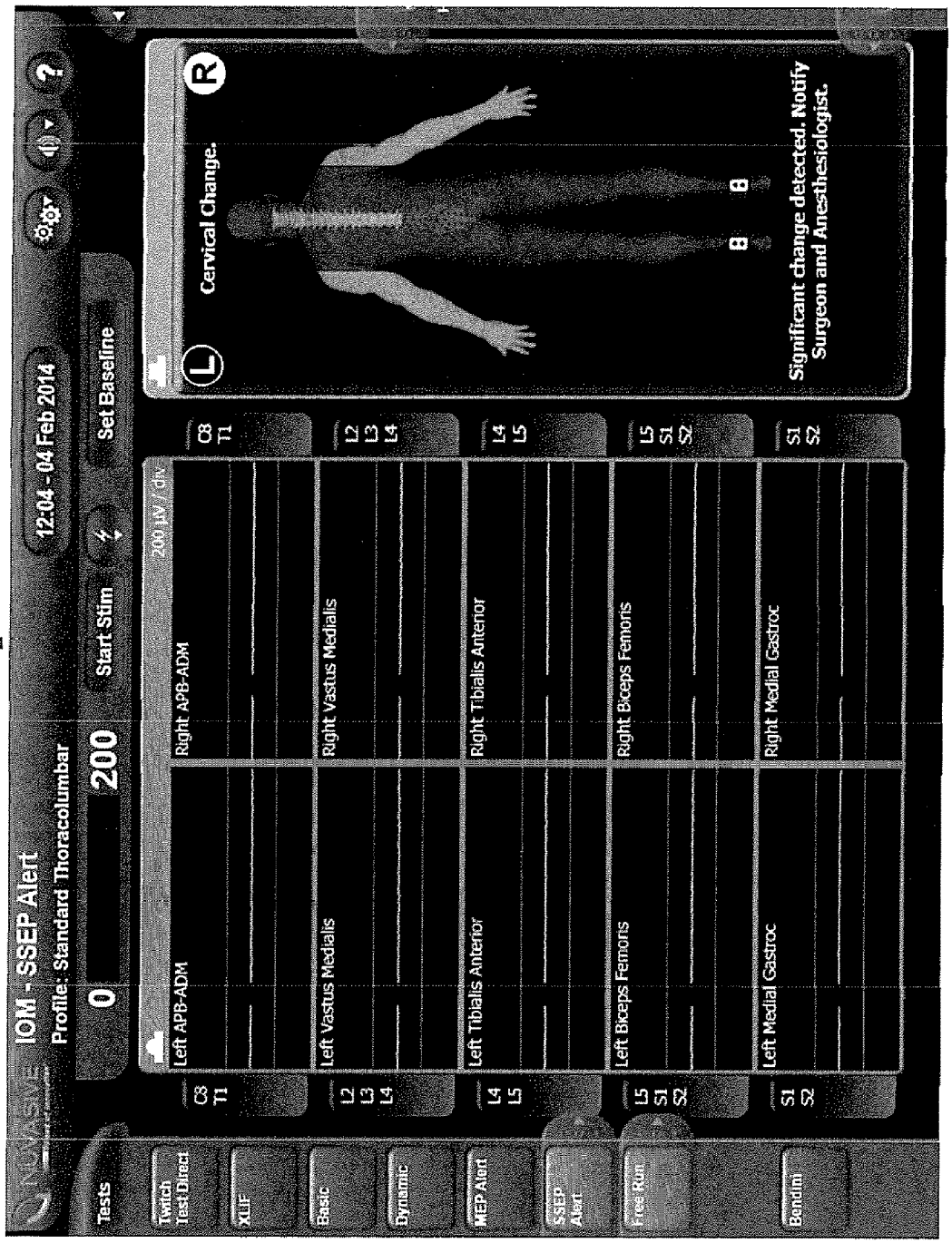
FIG. 41 is a screenshot of a fourth embodiment of an SSEP Automatic Run screen forming part of the system of FIG. 1.

According to some implementations, the various warnings that may be associated with particular SSEP results may be displayed on an anatomical diagram of the body as shown in FIG. 41. Alerts may be displayed on the diagram to represent the peripheral and spinal segment regions as set forth, by way of example only, in Table 10. According to one or more embodiments, it may be desirable to record from all four stimulation sites (e.g. Left Posterior Tibial Nerve, Right Posterior Tibial Nerve, Left Ulnar Nerve, and Right Ulnar nerve) from just two recording sites (by way of example, one subcortical recording location referenced to one cortical recording location). Such a configuration potentially alleviates the complexity associated with the different alert criteria required when managing peripheral, subcortical, and cortical responses simultaneously. By having all four stimulation sites use the same recording location, the user may be provided with information as to the health and status of the spinal cord without differentiating between electrodes. This facilitates the ability to troubleshoot technical issues. For example, noise caused by a dislodged recording electrode can be limited to one recording electrode to be examined. This also facilitates taking into account anesthetic effects on SSEP signals. For example, if there is a change to the anesthetic regime that affects the amplitude and/or latency of any responses, all four SSEP responses will change by the same amount because all responses are equally affected by anesthesia. This provides a direct method for determining the overall impact the anesthetic regime is having on the SSEP responses.

algorithm may include the following steps: (a) establish a rejection threshold to minimize the number of responses needed and the amount of noise allowed into the average; (b) use a noise floor window to isolate the white background noise level for comparison to the neurophysiological response; (c) analyze the stability of waveform markers to ensure they are reproducible amongst consecutive stimulations; and (d) store stimulation parameters for all stimulation sites when such stimulation parameters elicit clinically significant SSEP responses. Optionally, after the stimulation parameters are obtained for one stimulation site, the algorithm may optionally increase the stimulation frequency for the remaining stimulation sites to identify the proper stimulation parameters as quickly as possible. Once optimized baseline stimulation parameters are obtained, baseline SSEP recordings may be obtained and monitored during the procedure for significant changes to those baseline recordings.

Figure 42:
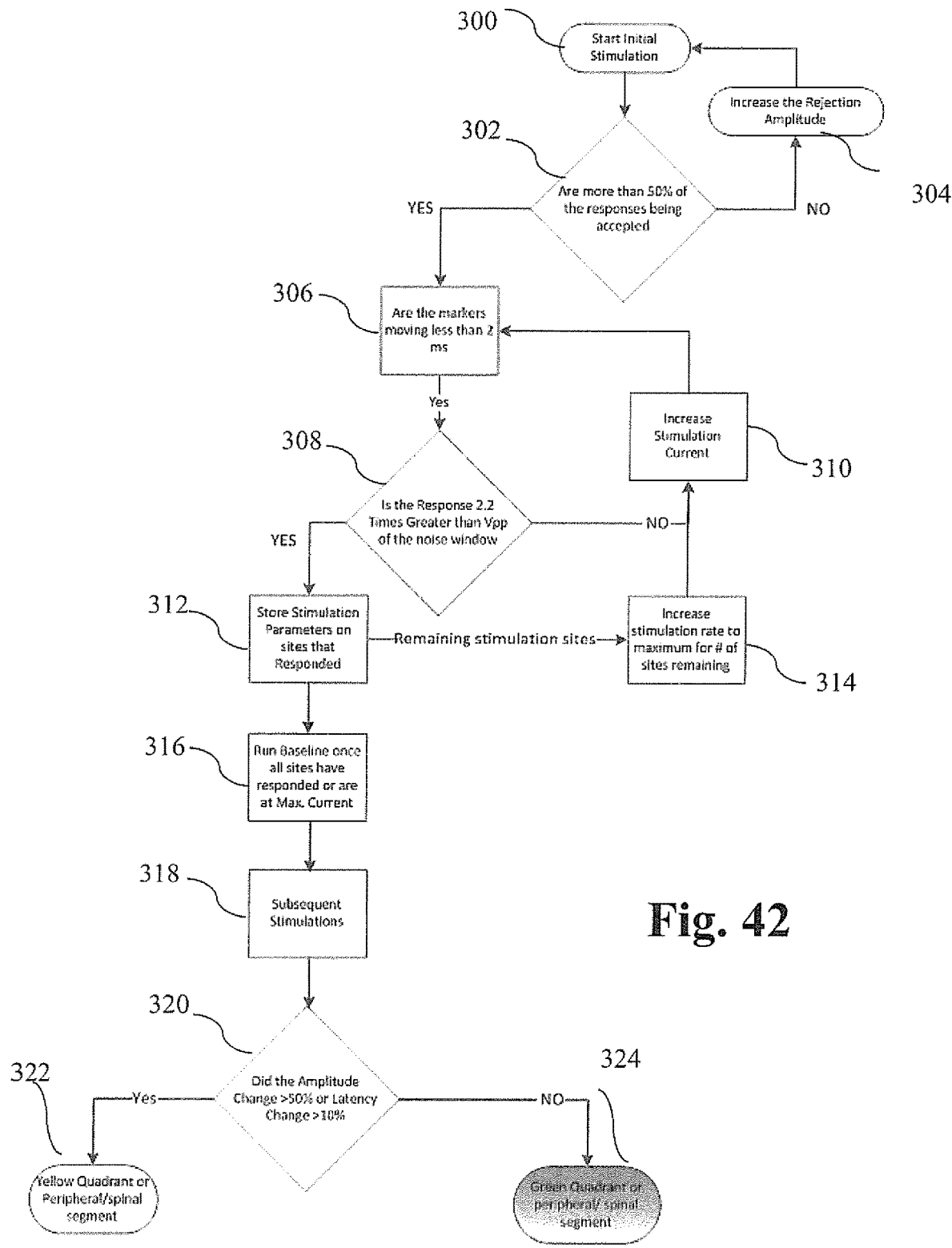
FIG. 42 is a flowchart illustrating a method by which a baseline hunting algorithm determines optimized SSEP acquisition conditions.

In general, minimizing the noise allowed into an SSEP average will reduce the number of responses required for a well-resolved response. In accordance with the present disclosure, a noise rejection threshold parameter is used to minimize the number of responses added to the average that have excessive interference. Referring now to FIG. 42, at step 300, the stimulating hunting algorithm process is started. The algorithm will first hunt for an optimal noise

TABLE 10

| Change from Baseline | Anatomy | Highlight | Visual Alert/Audio Alert |
| --- | --- | --- | --- |
| Amplitude >50% and Latency <10% | upper limb cervical spine thoracic spine | green limb green spine green spine | No message, tone associated with green |
|  | lower limb | green limb electrode | No message, no tone |
| Amplitude ≤50% or Latency ≥10% | upper limb cervical spine thoracic spine | yellow limb yellow spine yellow spine | "Significant change detected. Notify Surgeon and Anesthesiologist." Tone associated with yellow |
|  | lower limb | yellow limb electrode | "Significant change detected. Notify Surgeon and Anesthesiologist." Tone associated with yellow |

In accordance with the present disclosure, there are provided one or more algorithms executable on the control unit 14 of the system 10 that quickly enable the acquisition of a well-resolved SSEP waveform with a minimum number of stimulations, without the need for highly trained personal to be present to acquire or interpret the waveform. These algorithms may be used alone or in combination with one another to refine stimulation parameters until a combination resulting in the most desirable result is achieved. It is to be appreciated while the algorithms described below are described with respect to somatosensory evoked potentials (SSEP), it is equally applicable to all neurophysiologic modalities, including but not limited to motor evoked potential testing (MEP) and transcutaneous nerve root (TCNR) testing. It will also be appreciated that the algorithms described below are applicable to not just spine procedures but any procedure in which one or more aspects of the nervous system are at risk of permanent or transient injury or damage.

According to a broad aspect of the present invention, there is provided a baseline hunting algorithm that quickly ascertains a noise rejection threshold (NRT) and automatically optimizes baseline stimulation parameters for use in subsequent SSEP testing performed during the surgical procedure. According to one implementation, the baseline hunting rejection threshold to ensure that a significant number of stimulations are being allowed into the average (step 302). According to one embodiment, the system 10 analyzes how many stimulations are rejected as falling outside of the rejection threshold level. If the rejection rate is more than 50%, the system 10 increases the noise rejection threshold incrementally (e.g., +10 µV) shown as step 304 until the rejection rate is less than 50%. If the noise rejection threshold reaches a maximum (e.g., 250 µV) without reaching a less than 50% rejection rate, then the user is alerted to find the source of the interference before proceeding with SSEPs (e.g. a visual alert on the GUI screen "check electrode connection"). Once the rejection rate is less than 50%, the system 10 sets that rejection threshold level as the noise rejection level (i.e. noise floor) and the algorithm proceeds to refining the stimulation parameters as set forth below.

Once the noise rejection threshold has been identified, the stimulation continues and the algorithm proceeds to evaluate the stability of the SSEP waveforms. Stability of the SSEP waveforms may be evaluated as the degree to which an SSEP response moves or shifts each time it is refreshed on the graphical user interface. A stable response may be one that does not move/shift an appreciable amount between stimulations and an unstable response may be one that does move/shift an appreciable amount between stimulations. By way of example, the system 10 may measure stability by tracking latency over time. This may be accomplished, for example, via a pixel analysis to determine when the waveform is settled down into a consistent averaged response. At step 306, the system 10 continues to direct stimulation and measures the stability of the SSEP waveforms. According to one or more implementations, a waveform may be deemed "stable" when its latency markers does not vary more than 2 msec in between responses to successive stimulations.

Once the waveform is deemed stabilized such that N and P markers 314, 316 can be placed, the amplitude of the waveform is compared to the noise floor (defined as the noise rejection threshold obtained at step 302). At step 308, the system 10 compares the $V_{pp}$ of the response to the $V_{pp}$ of the noise floor to make sure that the response sufficiently greater than the noise floor to be deemed clinically significant. By way of example, a response may be deemed clinically significant when its amplitude is 2.2 times the amplitude of the noise floor. If the response is not sufficiently greater than the noise floor, the stimulation current is increased until a clinically significant response is evoked. By way of example, the stimulation intensity may be increased at step 310 incrementally (e.g. 10 mA) until a clinically significant response is found or until a maximum current is reached (e.g. 100 mA). The stimulation current level that produced that clinically significant response for that is recorded in memory at step 312. This stimulation current will be used for the baseline stimulation and all subsequent stimulations throughout the procedure. Stimulation hunting continues until the optimal parameters have been stored for each stimulation site. As shown in step 314, according to some implementations, the stimulation rate may be increased for remaining stimulation sites to make the hunting process as efficient as possible. By way example only, the stimulation rate may be increased to the maximum stimulation rate allowed for the remaining simulation sites that have not found a response.

After the stimulation intensity has been determined for all stimulation sites, the stored stimulation parameters are used to run the baseline (step 316). As shown in step 318, subsequent stimulations are run during the surgical procedure and compared to the baseline to determine if there is a significant change in the SSEP responses in one or more channels. As shown in step 320, SSEP changes are determined to be clinically significant if they exceed a predetermined criteria (e.g., an amplitude decrease of >50% and/or a latency increase of >10% from baseline). If the answer is yes, (step 322) there is a deemed significant change. If the answer is no (step 324), there is no significant change. These alerts are displayed to the user, by way of example, only, using one of the methods set forth above.

As set forth above, SSEP monitoring involves recording very low level signals in the presence of other biologic signals and noise. To overcome the noise, the evoked response is recorded anywhere from 50 to 500 times to average out any non-coherent, non-time locked response. The result is a clear waveform representing the desired nerve signal. In prior art systems, the user of the manually selects the number of times that the signal will be recorded for the entire procedure. If the noise level is high, a high number of samples to be taken. If the noise is low, then a low number of samples is taken. However, the ability to quickly obtain an SSEP result once the waveform is sufficiently well-resolved provides feedback to the user in a meaningful way. The present disclosure describes an algorithmic means of determining the number of evoked responses to include in the data set.

Figure 43:
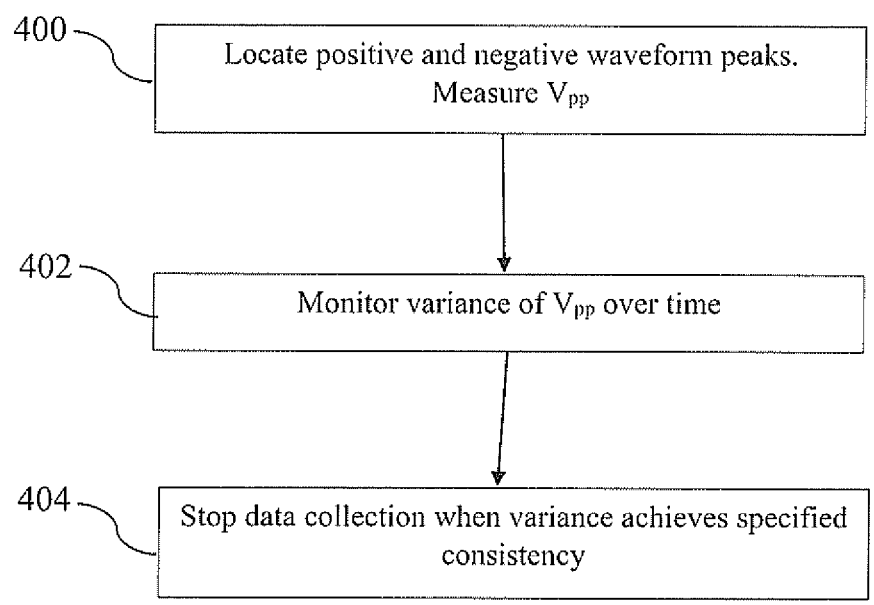
FIG. 43 is a flowchart illustrating a method by which a data set sizing algorithm determines the number of SSEP stimulations required to achieve a well-resolved SSEP waveform.

According to another broad aspect of the present invention, there is provided an algorithm for determining the number of evoked responses to include in a data set based on the variance of $V_{pp}$ amplitudes in the waveform. The algorithm will stop the averaging process once random biologic and noise information has been sufficiently averaged out. According to one implementation shown by way of example in FIG. 43, the positive and negative peaks of the waveform are located and their relative amplitude is measured (step 400). The variance of the $V_{pp}$ of the waveform is monitored over time as stimulations continue (step 402). When the variance achieves a specified consistency between data sets (for example <5%), the algorithm will automatically stop the SSEP data collection (step 404). For example, if the data collection is revealing a nerve signal peak-to-peak voltage of 1 µV and the next data set added to the average changes the amplitude by less than 5%, then the algorithm would command a stop to the data collection. It is to be appreciated that the tolerance for variations in the signal could be set parametrically (e.g. 0.5%, 1%, 5%) as well as the number of datasets that arrive within the established average (e.g. 1, 5, 10).

Low amplitude SSEP signals are often recorded in the presence of AC power line noise (typically 60 Hz or 50 Hz). The available SSEP stimulation rates are calculated to capture alternate positive and negative phases of the AC power line frequency, maximizing the rejection of power line noise through cancellation. Very often, when gathering sweeps to include in an average, a number of sweeps may be excluded from a given average due to amplitude rejection criteria, data communication interruption, or other causes. If an unequal number of positive or negative phase sweeps are included in the average, the final SSEP average may retain an undesirably high residual level of line frequency noise. The larger the discrepancy between the number of positive and negative phases included in the average, the larger that remaining residual level will be.

According to another broad aspect of the present invention, there is provided an algorithm to control the number of positive and negative phase sweeps included in the average. According to some implementations, the system 10 tracks the number of each phase included in the average, and adjust (by adding an appropriate number of positive or negative phase sweeps, whichever is lacking, or by removing an appropriate number of positive or negative phase sweeps, whichever is in excess) until the number of positive and negative phase sweeps in the average are equal. This could be done dynamically during, or at the end of an average.

According to one embodiment, sequential stimulations are tracked through the use of an identification tag, and a score of positive phase and negative phase line frequency components can be maintained. The firmware and/or the software application can then determine if an unmatched phase of line frequency noise is in the data set and thereby choose to collect additional data sets or subtract a data set until the score is matched for both phases.

While this invention has been described in terms of a best mode for achieving this invention's objectives, it will be appreciated by those skilled in the art that variations may be accomplished in view of these teachings without deviating from the spirit or scope of the present invention. For example, the present invention may be implemented using any combination of computer programming software, firmware or hardware. As a preparatory step to practicing the invention or constructing an apparatus according to the invention, the computer programming code (whether software or firmware) according to the invention will typically be stored in one or more machine readable storage mediums such as fixed (hard) drives, diskettes, optical disks, magnetic tape, semiconductor memories such as ROMs, PROMs, etc., thereby making an article of manufacture in accordance with the invention. The article of manufacture containing the computer programming code is used by either executing the code directly from the storage device, by copying the code from the storage device into another storage device such as a hard disk, RAM, etc. or by transmitting the code on a network for remote execution. As can be envisioned by one of skill in the art, many different combinations of the above may be used and accordingly the present invention is not limited by the specified scope.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

We claim:

1. An apparatus for performing somatosensory evoked potential monitoring during surgery, comprising:
    a control unit, said control unit being configured to:
        receive evoked somatosensory response data based on transmission of a plurality of electrical stimulation signals to a peripheral nerve of a patient;
        increase a number of allowed evoked somatosensory responses from the evoked somatosensory response data by modifying a noise rejection threshold until the evoked somatosensory response data have a rejection rate that is less than a predetermined rejection rate value;
        evaluate a plurality of latency values corresponding to the allowed evoked somatosensory responses from the evoked somatosensory response data;
        based on (i) the evaluation satisfying a stability threshold and (ii) a comparison of an amplitude value of the evoked somatosensory response data to an amplitude value of the modified noise rejection threshold, refining at least one stimulation signal parameter that corresponds to at least one of the plurality of electrical stimulation signals; and
        direct transmission of subsequent electrical stimulation signals using the at least one refined stimulation signal parameter.

2. The apparatus of claim 1, wherein the control unit is further configured to receive instructions from a user to modify the at least one stimulation signal parameter.

3. The apparatus of claim 1, wherein the at least one stimulation signal parameter is at least one of stimulation rate, current, pulse width, and polarity.

4. The apparatus of claim 3, wherein the control unit is further configured to refine the at least one stimulation signal parameter automatically.

5. The apparatus of claim 4, wherein the control unit is further configured to perform a threshold hunting algorithm to refine the subsequent electrical stimulation signals.

6. The apparatus of claim 1, wherein the control unit is further configured to perform at least one of stimulated electromyography and motor evoked potential assessments.

7. The apparatus of claim 1, wherein the control unit is further configured to generate an alert and provide instructions to display a cause for an alert condition to a user.

8. The apparatus of claim 7, wherein the cause for the alert condition relates to at least one of anesthetic, cortical ischemia, muscle activity artifact, mechanical insult, and an electrode issue.

9. The apparatus of claim 7, wherein the cause for the alert condition is at least partially attributable to ischemia of at least one of the spinal cord and brain of the patient.

10. The apparatus of claim 7, wherein the cause for the alert condition is at least partially attributable to an electrode issue, and the optimal noise rejection threshold is at least 100 µV.

11. The apparatus of claim 7, wherein the cause for the alert condition is at least partially attributable to a mechanical insult to the spinal cord of the patient.

12. The apparatus of claim 7, wherein the cause for the alert condition is at least partially attributable to a degradation of a somatosensory response along at least one limb of the patient.

13. A method for performing somatosensory evoked potential monitoring during surgery, the method comprising:
    receiving evoked somatosensory response data based on transmission of a plurality of electrical stimulation signals to a peripheral nerve of a patient;
    increasing a number of allowed evoked somatosensory responses from the evoked somatosensory response data by modifying a noise rejection threshold until the evoked somatosensory response data have a rejection rate that is less than a predetermined rejection rate value;
    evaluating a plurality of latency values corresponding to the allowed evoked somatosensory responses from the evoked somatosensory response data;
    based on (i) the evaluation satisfying a stability threshold and (ii) a comparison of an amplitude value of the evoked somatosensory response data to an amplitude value of the modified noise rejection threshold, refining at least one stimulation signal parameter that corresponds to at least one of the plurality of electrical stimulation signals; and
    directing transmission of subsequent electrical stimulation signals using the at least one refined stimulation signal parameter.

14. The method of claim 13, wherein the at least one stimulation signal parameter is at least one of stimulation rate, current, pulse width, and polarity.

15. The method of claim 14, wherein refining the at least one stimulation signal parameter comprises refining the at least one stimulation signal parameter automatically.

16. The method of claim 15, wherein refining the at least one stimulation signal parameter comprises performing a threshold hunting algorithm to refine the subsequent electrical stimulation signals.

17. A method for performing somatosensory evoked potential monitoring during surgery, the method comprising:
    receiving evoked somatosensory response data based on transmission of a plurality of electrical stimulation signals to a peripheral nerve of a patient;
    increasing a number of allowed evoked somatosensory responses from the evoked somatosensory response data by modifying a noise rejection threshold until the evoked somatosensory response data have a rejection rate that is less than 30%;
    evaluating a plurality of latency values corresponding to the allowed evoked somatosensory responses from the evoked somatosensory response data;
    based on (i) the evaluation satisfying a stability threshold and (ii) a comparison of an amplitude value of the evoked somatosensory response data to an amplitude value of the modified noise rejection threshold, refining at least one stimulation signal parameter that corresponds to at least one of the plurality of electrical stimulation signals; and directing transmission of subsequent electrical stimulation signals using the at least one refined stimulation signal parameter.

18. The method of claim 17, wherein the at least one stimulation signal parameter is at least one of stimulation rate, current, pulse width, and polarity.

19. The method of claim 18, wherein refining the at least one stimulation signal parameter comprises refining the at least one stimulation signal parameter automatically.

20. The method of claim 19, wherein refining the at least one stimulation signal parameter comprises performing a threshold hunting algorithm to refine the subsequent electrical stimulation signals.

* * * * *